US011655283B2

(12) United States Patent
Carosella et al.

(10) Patent No.: US 11,655,283 B2
(45) Date of Patent: May 23, 2023

(54) HLA-G TRANSCRIPTS AND ISOFORMS AND THEIR USES

(71) Applicants: COMMISSARIAT A L'ENERGIE ATOMIQUE ET AUX ENERGIES ALTERNATIVES, Paris (FR); ASSISTANCE PUBLIQUE—HOPITAUX DE PARIS, Paris (FR)

(72) Inventors: Edgardo D. Carosella, Paris (FR); Diana Tronik-Le Roux, Meudon (FR); Jean-Philippe Deslys, La Celle Saint-Cloud (FR); Jérôme Verine, Antony (FR); François Desgrandchamps, Paris (FR); Nathalie Rouas-Freiss, Paris (FR); Joël Le Maoult, Melun (FR)

(73) Assignees: COMMISSARIAT A L'ENERGIE ATOMIQUE ET AUX ENERGIES ALTERNATIVES, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 312 days.

(21) Appl. No.: 16/625,254

(22) PCT Filed: Jul. 24, 2018

(86) PCT No.: PCT/EP2018/070061
§ 371 (c)(1),
(2) Date: Dec. 20, 2019

(87) PCT Pub. No.: WO2019/020641
PCT Pub. Date: Jan. 31, 2019

(65) Prior Publication Data
US 2020/0148743 A1 May 14, 2020

(30) Foreign Application Priority Data
Jul. 24, 2017 (EP) .................................... 17305986

(51) Int. Cl.
A61K 38/17 (2006.01)
C07K 14/47 (2006.01)
C07K 14/74 (2006.01)
C07K 16/28 (2006.01)
C12N 15/79 (2006.01)

(52) U.S. Cl.
CPC .... C07K 14/70539 (2013.01); A61K 38/1709 (2013.01); A61K 38/1774 (2013.01); C07K 14/47 (2013.01); C07K 16/2833 (2013.01); C12N 15/79 (2013.01); C07K 2317/33 (2013.01)

(58) Field of Classification Search
CPC .................. C07K 14/70539; A61K 38/1774
See application file for complete search history.

(56) References Cited

U.S. PATENT DOCUMENTS 10,702,559 B2 * 7/2020 Lesser .................... C07K 14/33
2004/0166519 A1 8/2004 Cargill et al.
2007/0020703 A1 * 1/2007 Menier ............. A61K 38/1774
514/13.5

FOREIGN PATENT DOCUMENTS

WO 2007091078 A2 8/2007
WO WO-2007091078 A2 * 8/2007 ............. C07K 16/00
WO 2014072534 A1 5/2014

OTHER PUBLICATIONS

Carmeliet et al., Nature, 2000, vol. 407:249-257.*
International Search Report dated Dec. 4, 2018, issued in corresponding International Application No. PCT/EP2018/070061, filed Jul. 24, 2018, 5 pages.
Written Opinion of the International Searching Authority dated Dec. 4, 2018, issued in corresponding International Application No. PCT/EP2018/070061, filed Jul. 24, 2018, 9 pages.
Database EMBL [Online], "Synthetic construct DNA, clone: pF1KB6430, Homo sapiens HLA-G gene for major histocompatibility complex, class I, G, without stop codon, in Flexi system," XP002775419, retrieved from EBI accession No. AB528641, Oct. 2009, 1 page.
Database EMBL [Online], Homo sapiens MHC class I antigen HLA-G mRNA (HLA-G*01013 allele), XP002775420, retrieved from EBI accession No. EMBL:AF071017, Jul. 7, 1998, 1 page.
Database EMBL [Online], "Homo sapiens MHC class I antigen (HLA-G) gene, HLA-G*0103 allele, exons 2, 3 and partial cds," XP002775421, retrieved from EBI accession No. EMB L: AY672598, Jul. 26, 2004, 1 page.
Database Geneseq [Online], "Classical HLA capture oligonucleotide, SEQ ID: 16141," XP002775422, retrieved from EBI accession No. GSN:BAF49948, Dec. 20, 2012, 1 page.
Database Geneseq [Online], "Classical HLA capture oligonucleotide, SEQ ID:13276," XP002775423, retrieved from EBI accession No. GSN:BAF47083, Dec. 20, 2012, 1 page.

(Continued)

Primary Examiner — Xiaozhen Xie
(74) Attorney, Agent, or Firm — Christensen O'Connor Johnson Kindness PLLC

(57) ABSTRACT

Embodiments of the disclosure pertain to the field of HLA-G molecules and their therapeutic use. The disclosure pertains to new HLA-G isoforms, that is to say new RNA transcripts and proteins deriving from the HLA-G gene, pharmaceutical composition comprising thereof, as well as primers specific of these transcripts and antibodies specific of these proteins. The disclosure further pertains to the diagnostic or therapeutic use of these molecules.

Figure 1:
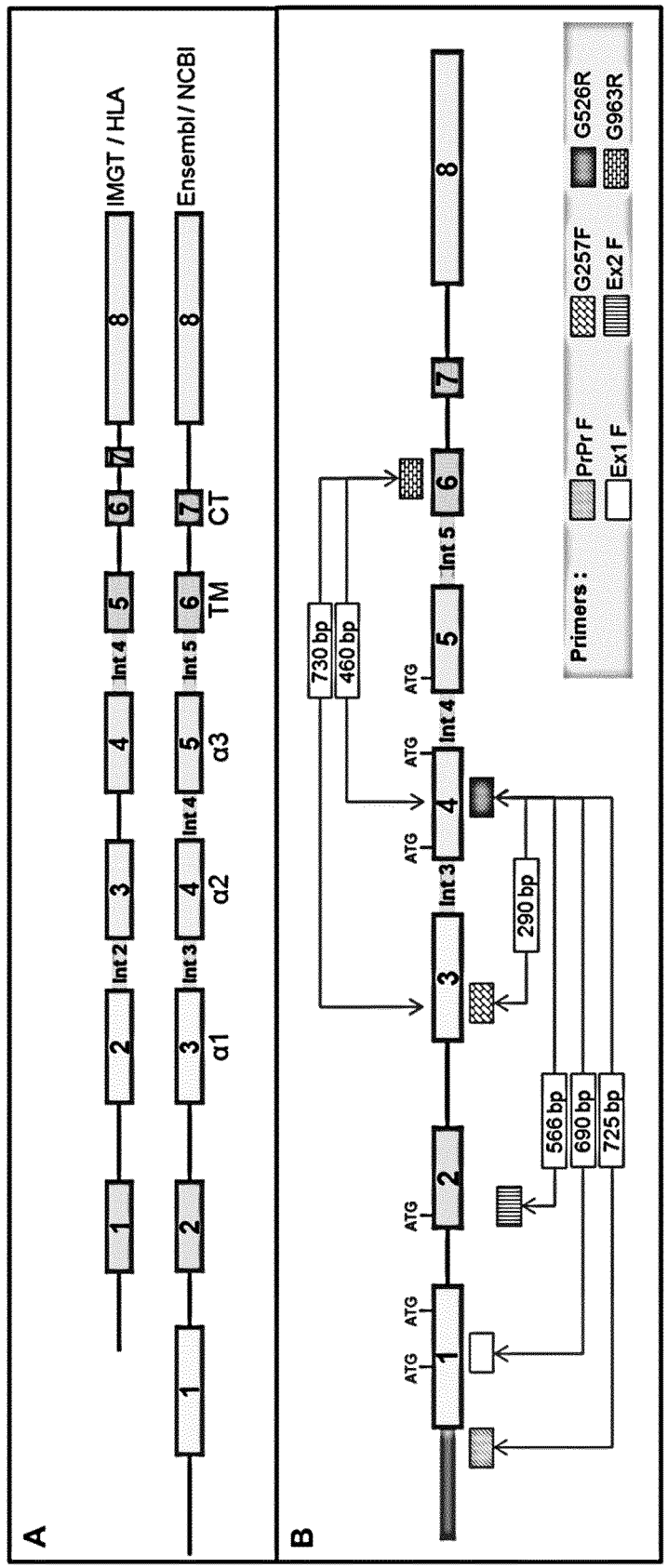

2 Claims, 10 Drawing Sheets
Specification includes a Sequence Listing.

(56) References Cited

OTHER PUBLICATIONS

Carosella, E.D., et al., "HLA-G: An Immune Checkpoint Molecule," Advances in Immunology, Academic Press, 127:33-144, Jan. 1, 2015.

Tronik-Le Roux, D, et al., "Novel landscape of HLA-G isoforms expressed in clear cell renal cell carcinoma patients," Molecular Oncology 11(11):1561-1578, Sep. 13, 2017.

* cited by examiner

A

RCC7 GFP  RCC7 HLA-G1  RCC7 HLA-G1L  RCC7 HLA-G1L

B

RCC7 HLA-G1L  RCC7 HLA-G1L  RCC7 HLA-G1  RCC7 GFP

HLA-G TRANSCRIPTS AND ISOFORMS AND THEIR USES

The invention pertains to the field of HLA-G molecules and their therapeutic use. The invention pertains to new HLA-G isoforms, that is to say new RNA transcripts and proteins deriving from the HLA-G gene, pharmaceutical composition comprising thereof, as well as primers specific of these transcripts and antibodies specific of these proteins. The invention further pertains to the diagnostic or therapeutic use of these molecules.

PRIOR ART

HLA-G is a HLA-class Ib molecule with potent immunomodulatory activities, which is expressed in physiological conditions, where modulation of the immune response is required to avoid allograft recognition (i.e., maternal-fetal interface or transplanted patients). HLA-G was first described to play a crucial role in the maintenance of pregnancy [1] and was found constitutively expressed at the fetal maternal interface in extravillous cytotrophoblasts.

HLA-G has a tolerogenic effect, modulating adaptive and innate immunity by interacting with T or B lymphocytes and NK cells or polymorphonuclear cells. This effect is mediated by the direct binding of both completely soluble and membrane-bound isoforms to inhibitory receptors via the α3 domain. Indeed, B and T lymphocytes, NK cells, and monocytes of the myeloid lineage express the immunoglobulin-like transcript ILT2 (CD85j, ILIRB1) [15]; monocytes, macrophages, and dendritic cells express ILT-4 (CD85d, LILRB2) [16]. The killer cell immunoglobulin-like receptor (KIR2DL4/p49) is specific for HLA-G and is expressed by decidual NK cells. Unlike other inhibitory receptors, it may also mediate activation [17, 18]. In addition, soluble HLA-G triggers the apoptosis of T and NK cells via CD8-like classical class I soluble molecules [19].

HLA-G expression is restricted to some tissues in normal conditions but increases strongly in pathological conditions. Indeed, HLA-G is expressed de novo at high levels in several pathological conditions, including solid and hematological tumors. Overexpression of membrane-bound and soluble HLA-G has been detected in different human solid and hematological tumors and might represent a mechanism performed by tumor cells to escape from the control of the immune system, by inhibiting NK and T cells mediated lysis. In particular, high incidence of HLA-G expression has been reported in clear cell renal cell carcinoma (ccRCC) [2, 3], which is among the most common human renal malignancy [4]. In addition, the role of HLA-G as an immune checkpoint allowing tumor escape has been demonstrated in murine models [5, 6].

On the other hand, the loss of HLA-G mediated control of the immune responses may lead to the onset of autoimmune/inflammatory diseases, caused by an uncontrolled activation of the immune effector cells. Several studies in the last years have demonstrated that HLA-G plays an important role in the control of autoimmune/inflammatory diseases, such as multiple sclerosis (MS), Crohn's disease (CD), psoriasis, pemphigus, celiac disease, systemic lupus erythematosus (SLE), asthma, juvenile idiopathic arthritis, and rheumatoid arthritis (RA) [23].

Seven isoforms of HLA-G have been identified, among which 4 are membrane-bound (HLA-G1, HLA-G2, HLA-G3 and HLA-G4) and 3 are soluble (HLA-G5, HLA-G6 and HLA-G7). All of these HLA-G comprise a peptide signal in their N terminus.

The HLA-G1 protein isoform comprises the three external domains ($\alpha 1$, $\alpha 2$ and $\alpha 3$), the transmembrane region and the cytoplasmic domain. The HLA-G2 protein isoform does not comprise the $\alpha 2$ domain, i.e., the $\alpha 1$ and $\alpha 3$ domains are directly linked, followed by the transmembrane domain and the cytoplasmic domain. The HLA-G3 protein isoform lacks both the $\alpha 2$ and $\alpha 3$ domains, i.e., it comprises the $\alpha 1$ domain directly linked to the transmembrane domain and the cytoplasmic domain. The HLA-G4 protein isoform lacks the $\alpha 3$ domain, i.e., it comprises the $\alpha 1$ domain, the $\alpha 2$ domain, the transmembrane domain and the cytoplasmic domain.

Soluble HLA-G isoforms all lack the transmembrane and cytoplasmic domains. Interestingly, all these soluble HLA-G proteins contain additional amino acids not present in any of the membrane-bound HLA-G, which result from the retention of one intron. More specifically:

The HLA-G5 protein isoform contains the $\alpha 1$, $\alpha 2$ and $\alpha 3$ domains, as well as an extra C-terminal peptide sequence of 21 amino acid residues encoded by intron 4 (as a result of intron 4 retention after transcript splicing and RNA maturation);

The HLA-G6 protein isoform corresponds to the HLA-G5 without $\alpha 2$, i.e., HLA-G6 contains $\alpha 1$ and $\alpha 3$ domains, as well as an extra C-terminal peptide sequence of 21 amino acid residues encoded by intron 4 (as a result of intron 4 retention after transcript splicing and RNA maturation);

The HLA-G7 protein isoform contains only the $\alpha 1$ domain, as well as 2 additional C-terminal amino acid residues encoded by intron 2 (as a result of intron 2 retention after transcript splicing and RNA maturation).

All seven reported HLA-G isoforms result from alternative splicing of one primary transcript, have a similar translation start site and no distinct functional roles have yet been proposed.

Thus far, the numbering of the exons of the HLA-G gene was based on the IMGT/HLA database (also herein called IMGT/HLA nomenclature), and was described as comprising 8 exons, 7 introns and a 3' untranslated end, corresponding respectively to the following domains: exon 1: signal sequence, exon 2: $\alpha 1$ extracellular domain, exon 3: $\alpha 2$, extracellular domain, exon 4: $\alpha 3$ extracellular domain, exon 5: transmembrane domain, exon 6: cytoplasmic domain I, exon 7: cytoplasmic domain II (untranslated), exon 8: cytoplasmic domain III (untranslated) and 3' untranslated region.

However, according to the Ensembl database, the HLA-G gene might possess a supplementary exon at the 5' end that is absent from the IMGT/HLA database. In addition, since the exon 7 corresponds to an untranslated domain, the question remains whether it is relevant to consider it as a exon per se.

The presence of this supplementary exon would thus modifies the size of the 5'-untranslated regions (UTR) and the location of the promoter. This may alter the regulation of the gene, by modifying the binding of regulatory proteins and/or miRNA.

Therapeutic approaches based on synthetic HLA-G-derived proteins or antibodies are emerging in mouse models, and these new therapeutic tools may prove useful for the treatment of cancer, infectious diseases, autoimmune/inflammatory diseases, and allogeneic graft rejection. Furthermore, it has been shown that the soluble form of HLA-G1 (also designated HLA-G5) inhibits angiogenesis, and its use as a therapeutic target for preventing pathologic neovascularization has been suggested [28].

In this context, there is thus a need for new therapeutic approaches based on HLA-G molecules.

DESCRIPTION

The inventors have discovered new transcripts of the HLA-G gene, most likely due to alternative splicing.

The inventors have demonstrated the presence of HLA-G transcripts harboring a supplementary sequence at the 5' extremity, corresponding to a region upstream of exon 1 (according to the IMGT/HLA nomenclature). Interestingly, these transcripts, herein called long HLA-G transcripts, also have a 106 bp deletion, compared to the previously known HLA-G transcripts, and possess an ATG that might be used as a translation initiation start point ([29]).

These results confirm the hypothesis that the use of a new nomenclature, based on the Ensembl database, is relevant. The Ensembl nomenclature is therefore used hereafter, unless specifically indicated. In this new nomenclature, illustrated in FIG. 1, a first exon is located within the supplementary sequence at the 5' extremity, and the previous exon 7 has been suppressed. The exon numbering is therefore modified in consequence: exon 1: corresponds to the newfound sequence; exon 2: signal sequence; exon 3: α1 extracellular domain; exon 4: α2 extracellular domain; exon 5: α3 extracellular domain; exon 6: transmembrane domain; exon 7: cytoplasmic domain I; exon 8: cytoplasmic domain III (untranslated) and 3' untranslated region (compared with IMGT/HLA nomenclature, exon 1 is renumbered exon 2, exon 2 is renumbered exon 3, etc).

The inventors have moreover discovered new HLA-G transcripts which retain either intron 1, 4, 6 or 7, as well as transcripts which retain two introns simultaneously, in particular introns 3 and 4 or introns 3 and 5, which had never been reported before.

The inventors have further shown that the alternative splicing results in the possibility of new translation initiation codons different form the translation initiation codon localized in exon 2, which had so far been considered as the only possible translation initiation codon of HLA-G proteins. In the new transcripts, possible translation initiation codons have been found in exon 1 and in exon 4.

In other terms, the new transcripts encode new HLA-G proteins, which respective structures differ from the HLA-G isoforms which had been disclosed so far.

Within these new transcripts, the inventors have identified several majors features that had not been disclosed in relation with HLA-G proteins before.

A first feature is the presence, in some of the new HLA-G proteins identified, of the five amino-acid residues MKTPR (SEQ ID NO: 1) at their N terminal extremity, that is to say upstream of exon 1 (according to the IMGT/HLA nomenclature). This feature results from the initiation of translation in exon 1. For convenience and clarity only, and independently of the actual length of their amino-acid sequence, the HLA-G proteins having this features are herein called "long HLA-G" to highlight the presence of said additional amino-acid residues.

A second feature is the absence of the α1 domain in some of the new HLA-G proteins identified.

A third feature is the absence of the transmembrane domain in some of the new HLA-G proteins identified, said proteins having a peptide sequence distinct from the known soluble HLA-G proteins HLA-G5, HLA-G6 and HLA-G7. For convenience and clarity only, the HLA-G proteins having these features are herein called "soluble HLA-G".

A forth feature is the retention, in some of the new HLA-G proteins identified, of at least part of an intron, different from introns 2 or 4, which retention is observed in HLA-G5, HLA-G6 and HLA-G7. It is anticipated that all of the newly identified HLA-G proteins have tolerogenic properties, consistently with the reported function of the already known HLA-G proteins. These proteins may thus be useful in the treatment of autoimmune/inflammatory diseases, such as multiple sclerosis (MS), Crohn's disease (CD), psoriasis, pemphigus, celiac disease, systemic lupus erythematosus (SLE), asthma, juvenile idiopathic arthritis, and rheumatoid arthritis (RA), as well as in the prevention of allogeneic graft rejection.

In addition, based on the knowledge in the field, the newly found HLA-G transcripts and corresponding proteins are expected to play a role in the ability of the cancer cells to evade immune checkpoints, and therefore constitute important therapeutic targets. In this context, the inventors have designed molecules targeting either the new RNA transcripts or the proteins they encode, as well as compositions comprising such molecules, which may be used in the treatment of cancer, in particular in clear cell renal cell carcinoma (ccRCC).

The inventors have demonstrated, as detailed in the experimental part, that the newly identified HLA-G proteins have a surprising angiogenic effect in vivo. This effect is in striking contrast with the effects of HLA-G5/soluble HLA-G1 reported in the literature. On the one hand, newly identified HLA-G proteins may thus be useful as therapeutic angiogenesis in the treatment of pathologies where such an angiogenic effect is desired, such as ischemia, which is a symptom found for instance in cardiovascular diseases, peripheral artery diseases and stroke.

Further, the inventors have designed primers and antibodies useful in the detection of these transcripts and of the proteins they encode, which may thus be used in diagnosing cancer.

A first aspect of the invention is thus an isolated HLA-G protein which sequence has at least one of the following features:
- it comprises the five amino-acid residues MKTPR, that is to say SEQ ID NO: 1, in its N terminal part, and/or;
- it is devoid of the α1 domain, that is to say it is devoid of the sequence SEQ ID NO: 3, and/or;
- it is devoid of the transmembrane/cytoplastic domain, that is to say it is devoid of SEQ ID NO: 6, and;
- it comprises amino-acids resulting from retention of at least part of one intron, proviso said intron is not intron 2 or intron 4.

The terms "HLA-G protein" encompass any protein or polypeptide resulting from the expression of the HLA-G gene, preferably the human HLA-G gene of gene ID 3135 (as referred to in the GeneBank database based on genome reference GRCh38.p10). Preferably, a "HLA-G protein" is a protein or polypeptide comprising at least a sequence corresponding to the translation of any of exons 1 to 8 of the human HLA-G gene according to the Ensembl nomenclature. In other terms, a "HLA-G protein" preferably comprises at least one of the following domains: the five amino-acid residues MKTPR (SEQ ID NO: 1) in its N terminal part, the peptide signal, the α1 domain, the α2 domain, the α3 domain, the transmembrane domain, and the cytoplasmic domain.

In the context of the invention, the "peptide signal" has the sequence SEQ ID NO: 2.

In the context of the invention, the "α1 domain" has the sequence SEQ ID NO: 3.

In the context of the invention, the "α2 domain" has the sequence SEQ ID NO: 4.

In the context of the invention, the "α3 domain" has the sequence SEQ ID NO: 5.

In the context of the invention, the "transmembrane/cytoplastic domain" has the sequence SEQ ID NO: 6.

The terms "amino-acids resulting from intron retention" should be construed as generally understood in the art. In the context of the invention, the person skilled in the art can easily identify such amino-acids by comparing the sequence of the protein with a reference sequence devoid of any amino-acid resulting from intron retention, such as for instance a reference sequence consisting in the translation of all the exons of the HLA-G gene. A reference sequence appropriate for such comparison is the sequence SEQ ID NO: 7, which corresponds to the peptide sequence of a HLA-G protein having all of the exons and none of the introns of the HLA-G gene, that is to say having the five amino-acid residues MKTPR (SEQ ID NO: 1) in their N terminal part, the peptide signal, the α1, α2 and the α3 domain, the transmembrane/cytoplasmic domain. According to the invention, any amino-acid residue which would constitute an addition in comparison with SEQ ID NO: 7 would result from intron retention.

Preferably, in the context of the invention, a "HLA-G protein which sequence is devoid of transmembrane/cytoplastic domain, that is to say which sequence is devoid of the sequence SEQ ID NO: 6", is a protein which sequence consists of:

At least part of SEQ ID NO: 1; and/or;
At least part of SEQ ID NO: 2; and/or;
At least part of SEQ ID NO: 3; and/or;
At least part of SEQ ID NO: 4; and/or;
At least part of SEQ ID NO: 5 and
  proviso said protein does not have the sequence of HLA-G5, HLA-G6 or HLA-G7, that is to say, respectively which does consist of any of the sequences SEQ ID NO: 90, 91 and 92.

The inventors have in particular identified several new HLA-G proteins according to the invention. The isolated HLA-G protein according to the invention is preferably a protein which sequence comprises or consists of a sequence chosen from the group consisting of SEQ ID NO: 7 to SEQ ID NO: 31.

Preferably, the HLA-G protein according to the invention, which sequence comprises the five amino-acid residues MKTPR (SEQ ID NO: 1) in their N terminal part is a protein which sequence comprises or consists of a sequence chosen from the group consisting of SEQ ID NO: 7, 8, 9, 10, 11, 12, 13, 14, 15, 16.

Preferably, the HLA-G protein according to the invention which sequence is devoid of α1 domain is a protein which sequence comprises or consists of a sequence chosen from the group consisting of SEQ ID NO: 9, 10, 11, 12, 13, 14, 17, 18, 19, 20, 22, 23, 24, 25, 26, 27, 29, 30, 31.

Preferably, the HLA-G protein according to the invention which sequence is devoid of transmembrane/cytoplasmic domain is a protein which sequence comprises or consists of a sequence chosen from the group consisting of SEQ ID NO: 8, 10, 12, 14, 16, 18, 20, 21, 23, 25, 27, 28, 30.

The HLA-G protein according to the invention may be a purified protein or a synthetic protein, which may be obtained by conventional techniques known from the person skilled in the art.

Preferably, the invention also encompasses variants of the above proteins, that is to say proteins which sequence has at least 80, 85, 90 or 95% identity with at least one of the above proteins.

In the sense of the present invention, the "percentage identity" or "% identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981), by means of the similarity search method of Pearson and Lipman (1988) or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid, nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST program, "BLAST 2 sequences" [27] available on the site http://www.ncbi.nlm.nih.gov/gorf/b12.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

Preferably, the invention further encompasses functional variants of the HLA-G proteins according to the invention, where amino acids residues are substituted for other amino acid residues with similar chemical properties (e.g., charge or hydrophobicity) and therefore do not change the functional properties of the molecule.

Preferably, the invention also encompasses modified proteins derived from the above proteins by introduction of any chemical modification into one or more amino acid residues, peptide bonds, N- and/or C-terminal ends of the protein, aimed at increasing the stability, bioavailability or bioactivity of the protein, as long as the modified protein remains functional.

As well known in the art, an alternative to the in vivo use of an isolated protein may be the use of a polynucleotide encoding said protein in expressible form or a recombinant vector comprising said polynucleotide. Such vectors are useful for the production of the protein, or for therapeutic use in vivo.

Another aspect of the invention relates to an isolated polynucleotide encoding a protein of the invention. The synthetic or recombinant polynucleotide may be DNA, RNA or combination thereof, either single- and/or double-stranded. Preferably the polynucleotide comprises a coding sequence which is optimized for the host in which the protein is expressed.

Another aspect of the invention relates to a recombinant vector comprising said polynucleotide. Preferably, said recombinant vector is an expression vector capable of expressing said polynucleotide when transfected or transformed into a host cell. The polynucleotide is inserted into the expression vector in proper orientation and correct reading frame for expression. Preferably, the polynucleotide is operably linked to at least one transcriptional regulatory sequence and, optionally to at least one translational regulatory sequence. Recombinant vectors include usual vectors used in genetic engineering and gene therapy including for example plasmids and viral vectors.

A further aspect of the invention provides a host cell transformed with said polynucleotide or recombinant vector.

The polynucleotide, vector, and/or cell of the invention may be prepared using well-known recombinant DNA techniques.

It is expected that the proteins of the invention have tolerogenic properties similar to the HLA-G proteins which are already known in the art, in particular since all of the newly found HLA-G proteins herein disclosed harbor a α3 domain.

Another aspect of the invention relates to a pharmaceutical composition, comprising at least one protein, polynucleotide and/or vector of the invention, and, preferably, a pharmaceutically acceptable carrier.

Suitable vehicles or carriers include any pharmaceutically acceptable vehicle such as buffering agents, stabilizing agents, diluents, salts, preservatives, emulsifying agents, sweeteners, etc. The vehicle typically comprises an isotonic aqueous or non-aqueous solution, which may be prepared according to known techniques. Suitable solutions include buffered solutes, such as phosphate buffered solution, chloride solutions, Ringer's solution, and the like.

A further aspect of the invention relates to a protein, polynucleotide, and/or vector of the invention for use as a medicament.

Preferably, the above proteins, polynucleotides and/or vector of the invention are for use in the treatment of autoimmune and/or inflammatory diseases, or in the prevention and/or treatment of allogeneic graft rejection, for use in the prevention and/or treatment of ischemia, preferably ischemia associated with cardiovascular diseases, peripheral artery diseases or stroke, or for use in the prevention and/or treatment of vascular retinopathies.

In the context of the invention, the term vascular retinopathies encompasses angiomatosis of Von Hippel, cavernous retinal hemangioma, coats disease, idiopathic macular telangiectasia (Reese's disease), occlusion of the central artery of the retina, occlusions of arterial branches, occlusion of the cilioretinal artery, occlusion of the ophthalmic artery, retinal vein occlusions.

In the context of medical use, the person skilled in the art may preferably select, among the HLA-G proteins of the invention, those which have the α-3 domain, such as for instance any of the proteins of sequence SEQ ID NO: 7, 8, 9, 10, 13, 14, 17, 18, 19, 20, 21, 22, 23, 26, 27, 31.

Advantageously, the HLA-G protein for use as a medicament, preferably for use in the above treatments, is a protein which sequence comprises or consists of a sequence chosen in the list consisting of SEQ ID NO: 7, 8, 9, 10, 13, 14, 17, 18, 19, 20, 21, 22, 23, 26, 27 and 31.

In the context of the invention, autoimmune/inflammatory diseases preferably refer to multiple sclerosis (MS), Crohn's disease (CD), psoriasis, pemphigus, celiac disease, systemic lupus erythematosus (SLE), asthma, juvenile idiopathic arthritis, and rheumatoid arthritis (RA), yet preferably psoriasis.

The invention also provides a method for the treatment of autoimmune/inflammatory diseases, or for the prevention and treatment of allogeneic graft rejection, for use in the prevention and/or treatment of ischemia, preferably ischemia associated with cardiovascular diseases, peripheral artery diseases or stroke, or for use in the prevention and/or treatment of vascular retinopathies, comprising: administering to an individual a therapeutically effective amount of at least one protein, polynucleotide and/or vector of the invention, or of the composition as described above.

By "therapeutically effective amounts" it is hereby referred to amounts which are, over time, sufficient to at least reduce or prevent disease progression. Typically, said amount can be adjusted by the skilled artisan, depending on the pathological condition, the subject, the duration of treatment, the presence of other active ingredients, etc.

As already said, the newly found HLA-G transcripts and corresponding proteins are important therapeutic targets, in particular for the treatment of cancer. Typically, for therapeutic purposes, RNA transcripts may be targeted by antisens oligonucleotides, while proteins may be targeted by specific antibodies.

For instance, RNA transcripts, which sequence is devoid of the sequence encoding the α1 domain but contains the sequence encoding the signal peptide and the α2 and α3 domains, have a junction between the sequence encoding the signal peptide and the sequence encoding the α2 domain, corresponding to the sequence SEQ ID NO: 32, which is not found in other HLA-G proteins. Similarly RNA transcripts which consist of the sequence encoding the α3 domain and the signal peptide, but are devoid of the α1 and α2 domains, comprise the sequence SEQ ID NO: 33, corresponding to a junction between the sequences encoding the α3 domain and the signal peptide. The RNA transcripts which encode soluble HLA-G comprise the sequence SEQ ID NO: 34.

Another object of the invention is an antisens oligonucleotide having a sequence complementary to at least part of
SEQ ID NO: 32;
SEQ ID NO: 33, or;
SEQ ID NO: 34.

The invention further pertains to a recombinant vector comprising a polynucleotide encoding at least one antisens oligonucleotide of the invention.

The new HLA-G proteins of the invention harbor the specific peptide sequence SEQ ID NO: 35, 36 and 37 encoded by the junction sequences SEQ ID NO: 32, 33 and 34 respectively, which may be used as antigen to produce antibodies specific for such proteins, that is to say anti-HLA-G antibodies specific of certain HLA-G proteins.

Another object of the invention is an antibody specific of at least one of the peptide of sequence SEQ ID NO: 35, 36 or 37.

For the purpose of the present invention, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')2, or Fab'). In addition, aggregates, polymers, and conjugates of immunoglobulins or their fragments may be used where appropriate so long as binding affinity for a particular molecule is substantially maintained.

The terms "antibody specific of at least one peptide", should be construed as generally understood in the field, that is to say as indicating that said antibody exhibits a substantial affinity for said at least one peptide, preferably an affinity of about $10^{-5}$ M (KD) or stronger. The affinity can be determined by various methods well known from the one skilled in the art, which include, but are not limited to, Biacore Analysis, Blitz analysis and Scatchard plot.

Another object of the invention is a pharmaceutical composition comprising an antibody, an antisens oligonucleotide, and/or a vector encoding thereof, according to the invention, and, preferably, a pharmaceutically acceptable carrier.

A further aspect of the invention relates to an antibody, an antisens oligonucleotide, and/or a vector encoding thereof, of the invention for use as a medicament.

Preferably, the above antibody, antisens oligonucleotide and/or vector encoding thereof, of the invention is used in the treatment of cancer.

Non-limitative examples of cancer include esophagus, stomach, colon, pancreas, melanoma, thyroid, lung, breast, kidney, bladder, uterus, ovary and prostate cancer; hepatocellular carcinomas, osteosarcomas, cylindromatose, neuroblastomas, glioblastomas, astrocytomas, colitis associated cancer, multiple myeloma and various types of leukemia and lymphomas such as diffuse large B-cell lymphoma, primary mediastinal B-cell lymphoma (PMBL), Hodgkin's lymphoma and MALT lymphoma. In a preferred embodiment said cancer is clear cell renal cell carcinoma (ccRCC).

The invention provides also a method for the treatment of a cancer, comprising: administering to an individual a therapeutically effective amount of the antibody, antisens oligonucleotide and/or vector encoding thereof, of the invention, or of the composition as described above.

As already indicated, the inventors have identified that samples of cancer cells comprise specific HLA-G transcripts, that is to say RNA molecules corresponding to the expression of the human HLA-G gene, These RNA transcripts corresponds to the sequences SEQ ID NO: 38 to 74. The inventors have thus developed an in vitro method for the diagnosis of cancer, based on the presence of such RNA transcripts in a biological sample.

The invention further pertains to an in vitro method for the diagnosis of a cancer, comprising the detection of at least at least a RNA transcript having a sequence chosen in the list consisting of the sequences SEQ ID NO: 38 to 74 and/or of at least one of the proteins of the invention as disclosed above, in a biological sample of a subject.

The term "biological sample" refers to a sample obtained from the subject, including sample of biological tissue or fluid origin. Such samples can be, but are not limited to, body fluid (e.g., blood, blood plasma, serum, or urine), organs, tissues, fractions, and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine). Preferably the subject is a mammal, yet preferably a human.

In the context of the invention, the detection of at least a RNA transcript having a sequence chosen in the list consisting of the sequences SEQ ID NO: 38 to 74, and/or of at least one of the proteins of the invention indicates that the subject has a cancer.

Non-limitative examples of cancer include esophagus, stomach, colon, pancreas, melanoma, thyroid, lung, breast, kidney, bladder, uterus, ovary and prostate cancer; hepatocellular carcinomas, osteosarcomas, cylindromatose, neuroblastomas, glioblastomas, astrocytomas, colitis associated cancer, multiple myeloma and various types of leukemia and lymphomas such as diffuse large B-cell lymphoma, primary mediastinal B-cell lymphoma (PMBL), Hodgkin's lymphoma and MALT lymphoma. In a preferred embodiment said cancer is clear cell renal cell carcinoma (ccRCC).

The detection of at least one of the proteins of the invention can be carried out by implementing a suitable immunological method (e.g. ELISA, RIA, immunofluorescence, immunohistochemistry) by means of at least one antibody specific of said protein, as disclosed above.

The detection of the RNA transcripts can be carried out by hybridization, by means of nucleotide probes specific for said RNAs (attached, for example, to a biochip), or by amplification (for example by RT-PCR), by means of nucleotide primers specific for said RNA transcripts.

The inventors have developed nucleotide primers particularly suitable for detecting at least one of the RNA transcripts of the invention:

the primer int4R, of sequence SEQ ID NO: 75, designed to hybridize with the beginning of intron 4, and which can therefore be used to detect the HLA-G transcripts that have retained this intron;

the primer Ex1F, of sequence SEQ ID NO: 76, designed to hybridize with a region complementary to exon1, and which can therefore be used to detect the transcripts encoding the long HLA-G proteins;

the primer PrPrF, of sequence SEQ ID NO: 77, designed to hybridize with a region located further upstream of the region annotated as the 5'-transcript end of the gene, reported as the promoter region, and which can therefore be used to detect the transcripts encoding the long HLA-G proteins;

the primer Int3F, of sequence SEQ ID NO: 78, designed to hybridize with a region located in intron 3 and which can be used to detect the HLA-G transcripts that have retained this intron;

the primer Int5R, of sequence SEQ ID NO: 79, designed to hybridize with a region located in intron 5 and which can be used to detect the HLA-G transcripts that have retained this intron.

Those primers are particularly useful for implementing the diagnosis method of the invention. Thus, in an embodiment, in the method of the invention, the detection of at least a RNA transcript of the invention is performed using at least a primer having a sequence chosen in the list consisting of SEQ ID NO: 75 to 79.

These specific primers may be used in combination with each other or other known primers specific of HLA-G transcripts, such as the primer G526R of sequence SEQ ID NO: 80, which has been disclosed in the art. Further any of the combinations of the primer Int3F and either the primer Int5R or the primer int4R may be used to detect the transcripts having retained two introns (introns 3 and 4, or introns 3 and 5).

In an preferred embodiment, in the method of diagnosis of the invention, the detection of at least a RNA transcript of the invention is performed using at least one of the combinations of:

the primer Ex1F of sequence SEQ ID NO: 76 or the primer PrPrF of sequence SEQ ID NO: 77, and the primer G526R of sequence SEQ ID NO: 80;
the primer int4R of sequence SEQ ID NO: 75, and the primer Int3F of sequence SEQ ID NO: 78;
the primer the primer Int3F of sequence SEQ ID NO: 78 and the primer Int5R of sequence SEQ ID NO: 79;

Another object of the invention is therefore a primer having a sequence chosen in the list consisting of SEQ ID NO: 75 to 79.

The invention further pertains to a kit comprising at least two primers having a sequence chosen in the list consisting of SEQ ID NO: 75 to 80.

Preferably, the kit comprises at least a combination of primers chosen in the list consisting of:

the primer Ex1F of sequence SEQ ID NO: 76 or the primer PrPrF of sequence SEQ ID NO: 77, and the primer G526R of sequence SEQ ID NO: 80;
the primer int4R of sequence SEQ ID NO: 75, and the primer Int3F of sequence SEQ ID NO: 78;
the primer Int3F of sequence SEQ ID NO: 78 and the primer Int5R of sequence SEQ ID NO: 79;

The invention also comprises other provisions that will emerge from the following examples of implementation, which may not be construed as limiting the scope of the invention.

LEGEND OF THE FIGURES

FIG. 1—Schematic representation of the structure of the HLA-G gene. A. IMGT/HLA nomenclature (top) and Ensembl database (bottom). Numbers represent exons and the domains of the HLA-G protein are shown underneath. TM: transmembrane; CT: cytoplasmic tail. B Localization of primers used for the different RT-PCR strategies. Sizes, in bp, for specific amplicons and the translation initiation codons are indicated.

Figure 2:
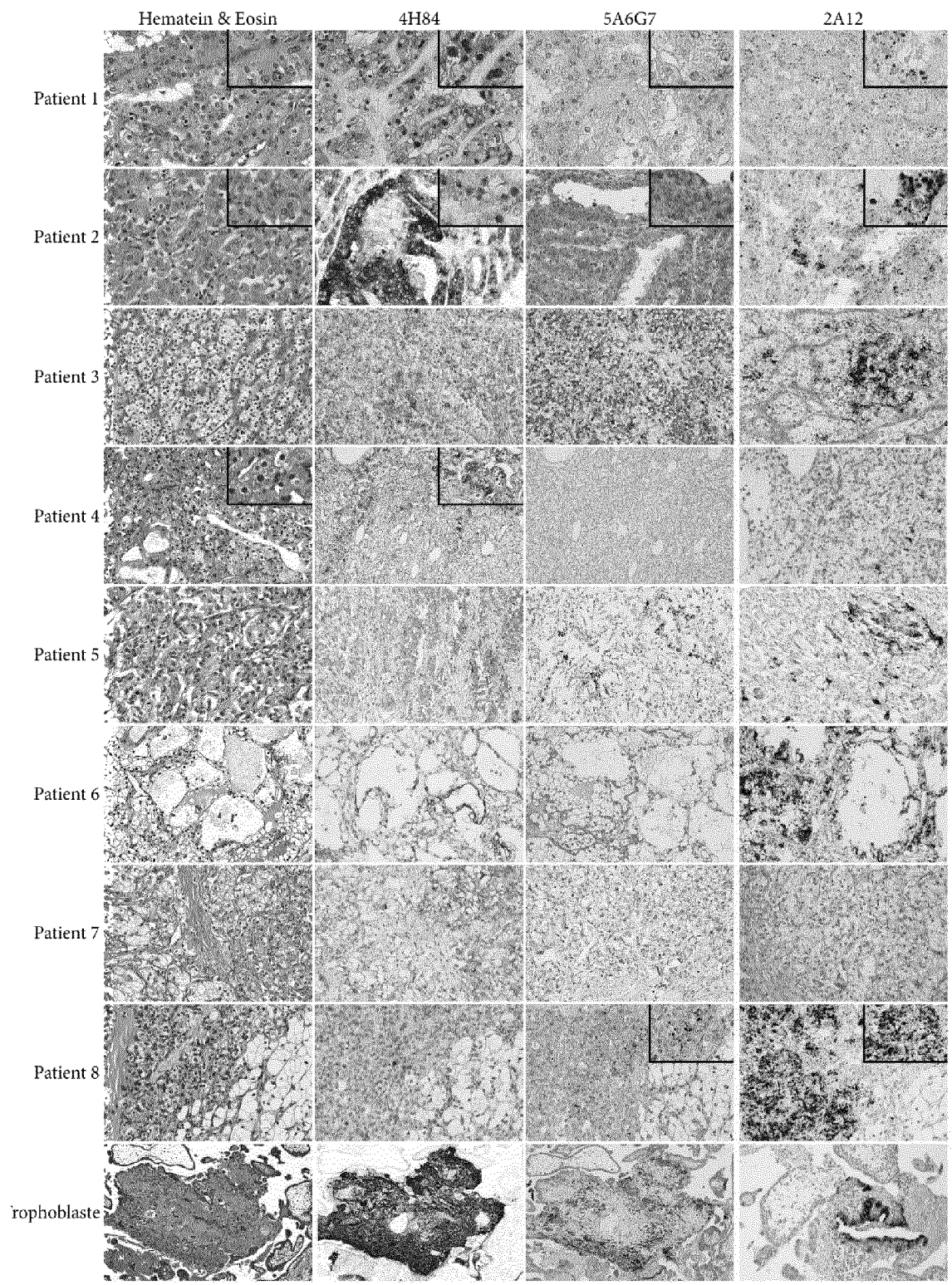

FIG. 2—Differential morphologic and HLA-G staining patterns of eight ccRCC included in this study. A trophoblastic tissue was used as positive control for immunohistochemical study (H&E and immunoperoxidase stains).

Figure 3:
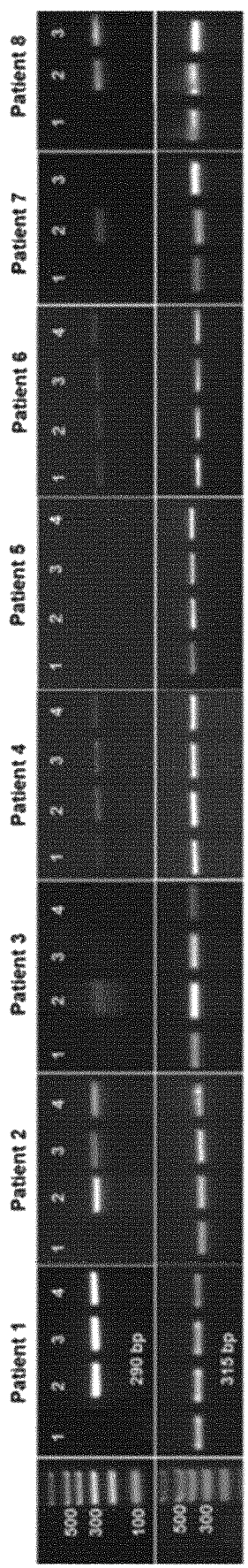

FIG. 3—Expression of HLA-G1 in ccRCC patients. RNA were subjected to RT-PCR using the HLA-G1 specific primers G257F and G526R (upper panels) and ACTB primers as controls (lower panels). Lanes 1: adjacent non-tumor region except for tumors of patients 6 and 8. Lanes 2, 3 and 4: different tumor areas. For patients 6 and 8, all regions shown correspond to tumor areas since partial nephrectomies were performed and adjacent tumor regions were not available. M: 100 bp size marker.

Figure 4:
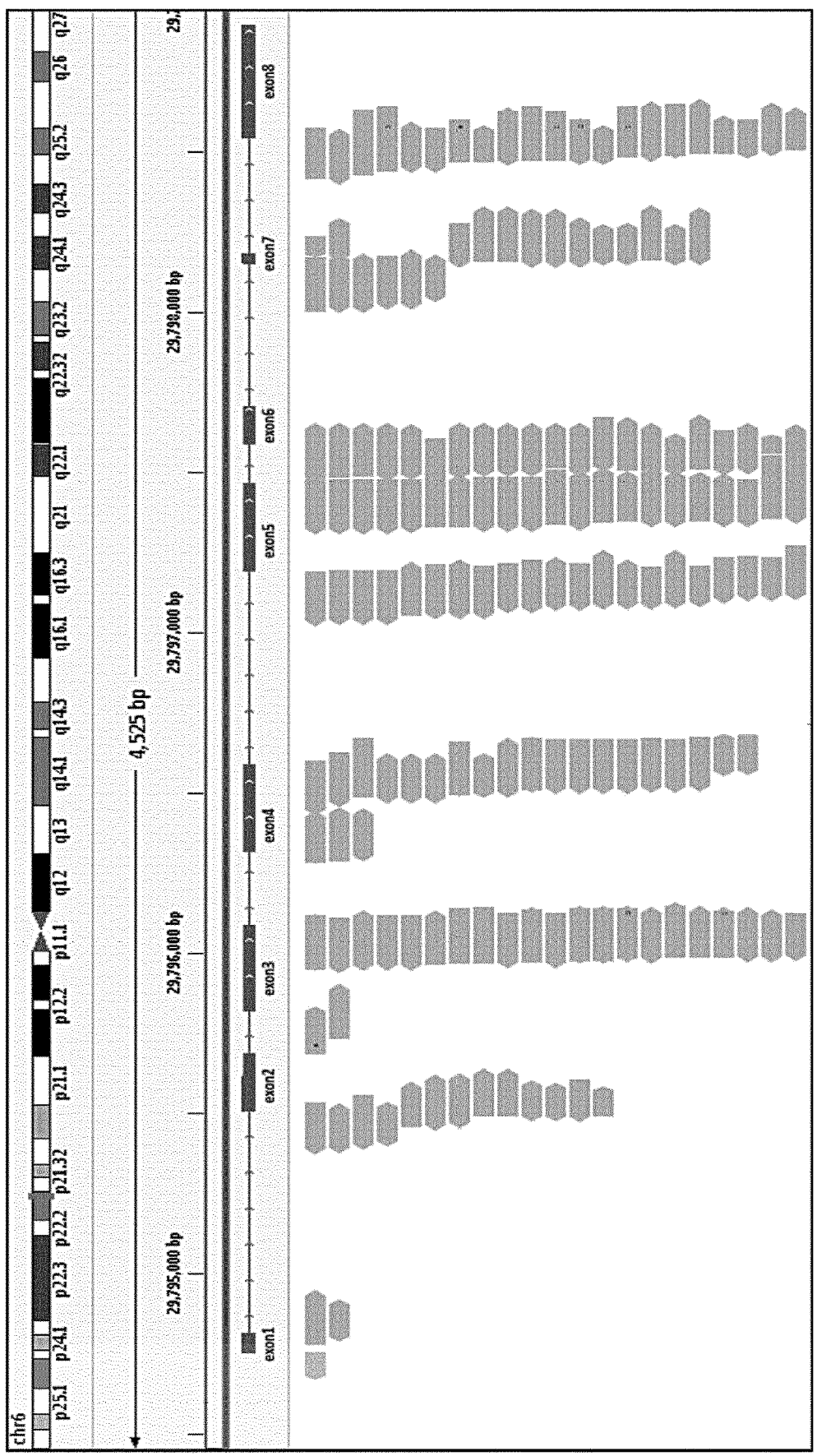

FIG. 4—Intron retention events found in HLA-G transcripts. Only reads spanning intron-exon junctions have been considered. Reads corresponding exclusively to intron sequences were discarded.

Figure 5:
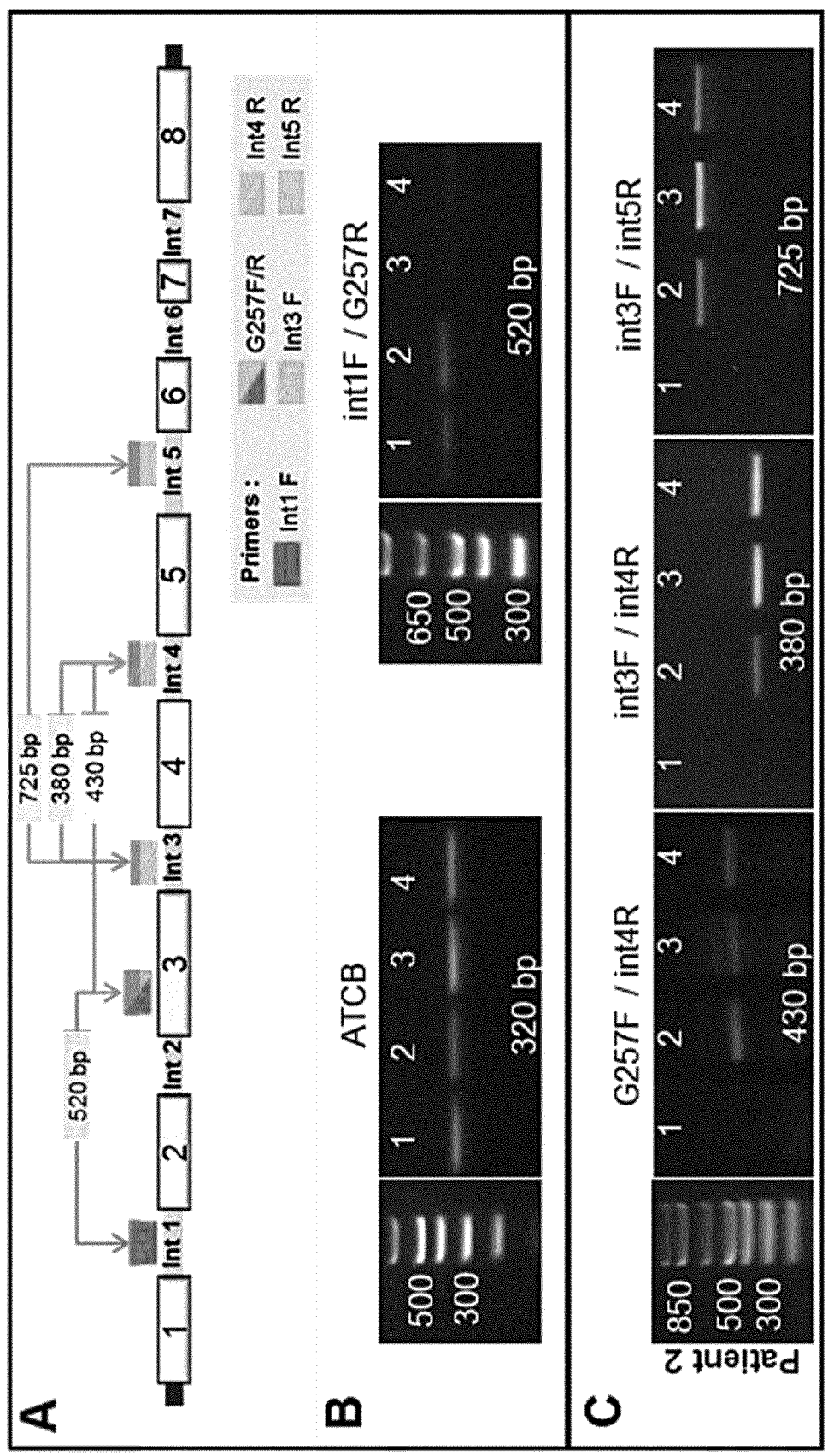

FIG. 5—Molecular validation of main intron retention events. A: Diagrammatic representation of the RT-PCR strategy developed to amplify retained introns. B: Results of the RT-PCR analysis using actin primers as control for the absence of genomic DNA (left) and Int1 and G257R primers to detect the presence of intron 1 (right). The band of 523 bp reveals the absence of intron 2, which would produce a band of 649 bp C: HLA-G transcripts that retain only intron 4 (left panel) or HLA-G transcripts that retain several introns simultaneously (middle and right panels).

Figure 6:
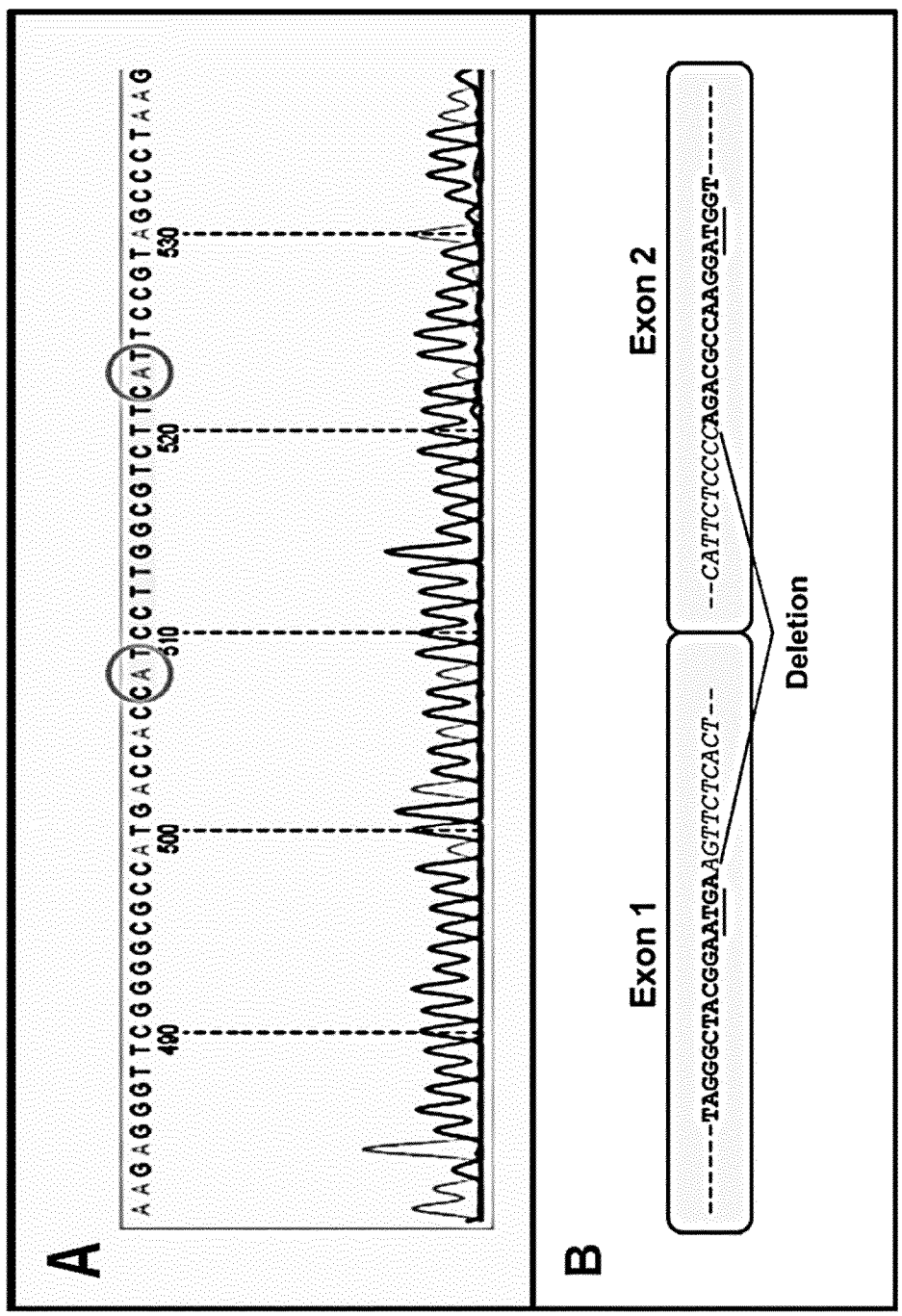

FIG. 6—Identification of the 5'-extended transcript HLA-G1. A. Detail of the DNA sequence showing the reduced distance between the two ATGs. The sequence was performed upwards using the G526R primer B. Schematic representation of the 106 bp-deletion; the two ATG are underlined.

Figure 7:
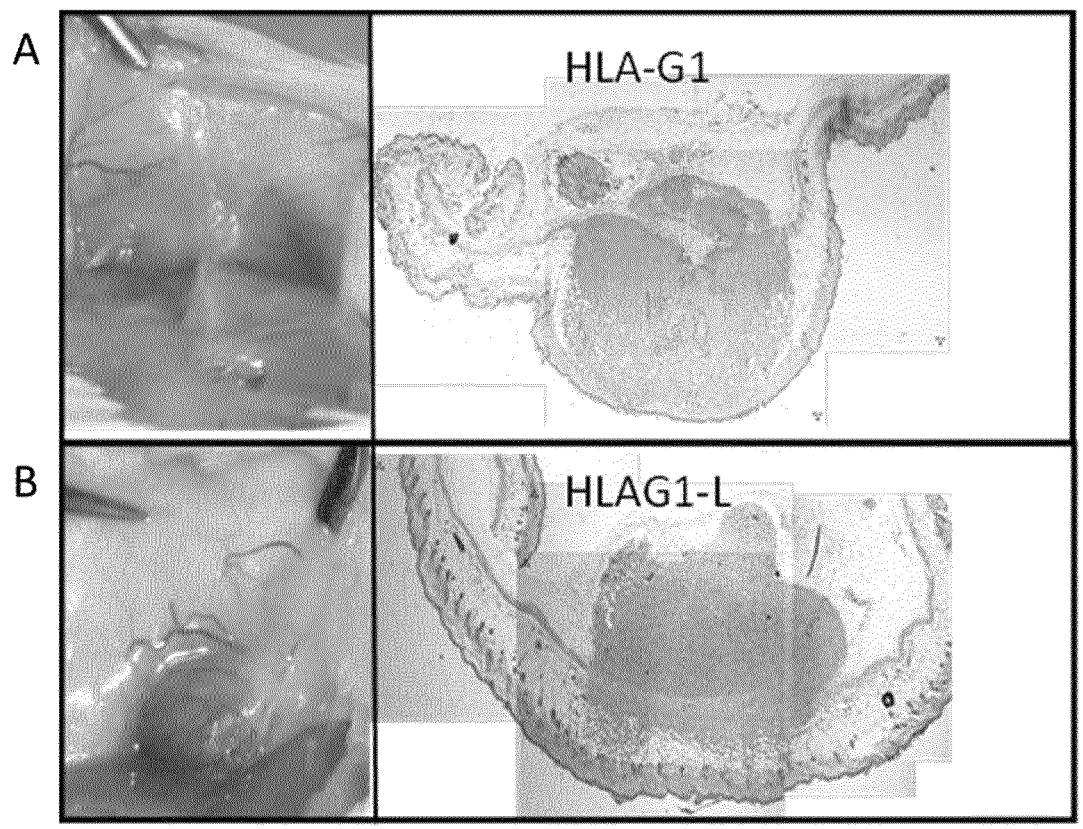

FIG. 7: A: Pictures of NSG mice xenografted with RCC7 cells infected with a viral vector encoding the long HLA-G1, taken on day 38 after injection. B: Pictures of NSG mice xenografted with RCC7 cells infected with a viral vector encoding the long HLA-G1L, taken on day 38 after injection.

Figure 8:
Figure 8:
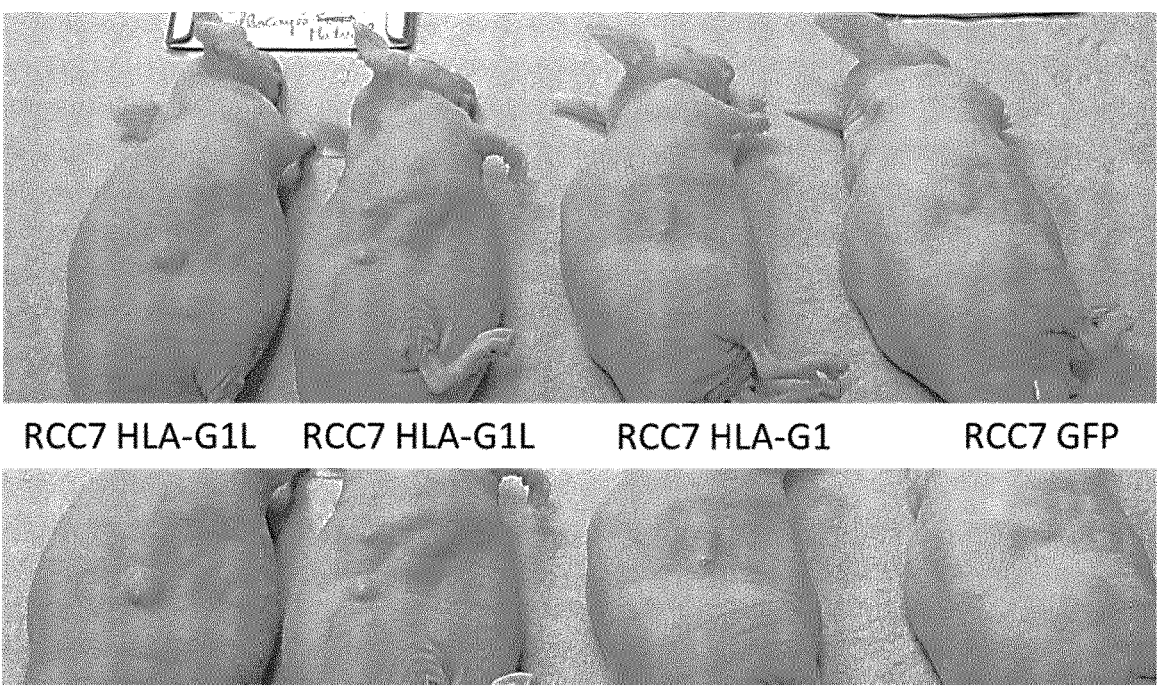

FIG. 8: A: Pictures of nude mice xenografted with RCC7 cells expressing either GFP, HLA-G1 or HLA-G1L, on day 25 after intradermal injection. B: Pictures of nude mice xenografted with RCC7 cells grown on matrigel and expressing either GFP, HLA-G1 or HLA-G1L, on day 25 after intradermal injection.

Figure 9:
Figure 9:

FIG. 9: Pictures of NSG immunodeficient mice 8 days after injection of a control RCC7 cells (expressing GFP) in the left ear, and of RCC7 cells expressing HLA-G1L in the right ear (A and B).

Figure 10:
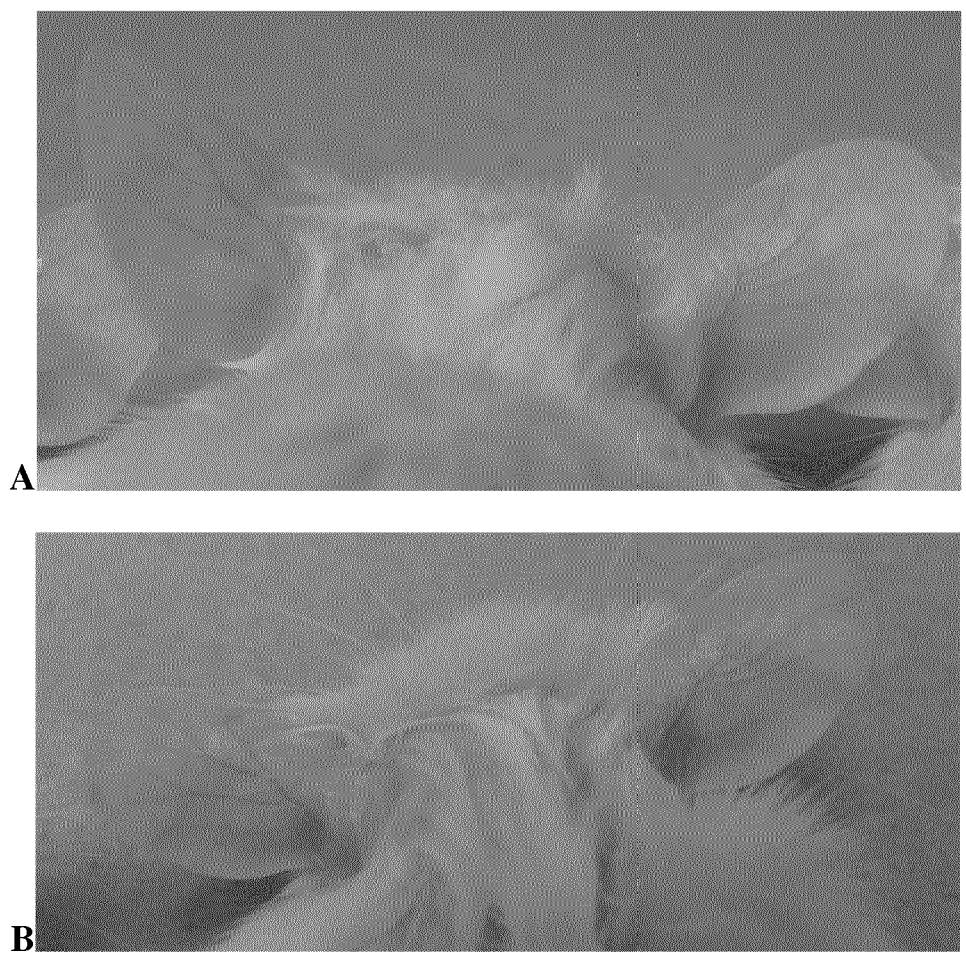

FIG. 10 Pictures of NSG immunodeficient mice 8 days after injection of control RCC7 cells in the left ear, and of RCC7 cells expressing HLA-G1 in the right ear (A and B).

EXAMPLES

A. Detection and Analysis of New HLA-G Isoforms
1. Materials and Methods
1.1 Tumor and Patients All patients of this study underwent a radical nephrectomy for ccRCC as first therapeutic intervention in the urology department of Saint-Louis Hospital (Paris, France) from November 2014 to April 2015. The median tumor size was of 50 mm (range, 35 to 175). According to the 2010 primary tumor TNM classification, these tumors were classified as pT1a (patient 6), pT1b (patients 1, 3, and 8), and pT3a (patients 2, 4, 5, and 7). Two patients (patients 2 and 4) had visceral metastases at presentation. All these renal tumors were classified as ccRCC by an experienced uropathologist according to the WHO classification of tumors of the kidney [8]. All patients that participated to this study gave their free and informed writing consent. The study was approved by the institutional review boards of Saint-Louis Hospital, Paris.

1.2 Tumor Specimen Processing

For each tumor and according to the tumor size, we isolated between 3 and 10 samples of 10×5×5 mm, representing the spatial extent and macroscopic intra-tumor heterogeneity. Half of each sample was snap frozen in liquid nitrogen within 1 h of clamping of the renal artery and the other half was used to perform histological analysis and was documented by photography. Regions that did not contain tumor cells on histopathological examination were also isolated as controls.

1.3 Immunohistochemistry

An immunohistochemical study was performed for each tumor on 4-μm-thick, formalin-fixed and paraffin-embedded tumor tissue sections. The following murine antibodies were used: 4H84, an IgG1 recognizing an epitope located into the alpha1 domain common to all HLA-G isoforms (dilution 1/200, Santa Cruz Biotechnology, Santa Cruz, Calif.), and two antibodies 5A6G7 and 2A12 recognizing the epitope encoded by the retained intron 5 (Ensembl database) present in soluble HLA-G5 and -G6 isoforms (dilution 1/100, Exbio antibodies, Exbio Co., CR). The staining was performed on automated slide stainers from Roche (BenchMark ULTRA system, Tucson, Ariz.) using the OptiView DAB IHC Detection Kit (Roche), Cell Conditioning 1 (CC1) short or standard antigen retrieval, an antibody incubation time of 32 min at 37° C., ultraWash procedure, counterstaining with Hematoxylin II for 4 min and bluing reagent for 8 min. Positive and negative controls gave appropriate results for each procedure.

The immunohistochemical analyses were performed by the uropathologist using a BX51 microscope (Olympus France S.A.S, Rungis). Each immunostaining was scored on the basis of membranous and/or cytoplasmic staining by both intensity of staining as negative, weak, moderate, or strong and distribution of staining as negative (0% of tumor area), minimal (0-10% of tumor area), focal (<50% of tumor area), or diffuse (>50% of tumor area). A trophoblastic tissue was used as the positive control and isotype-specific immunoglobulins were used for negative controls with each run.

1.4 Trophoblast Sample Preparation

Trophoblastic tissues were obtained from abortions (less than three months of pregnancy). After mechanical dissociation, the samples were preserved in Trizol™ Reagent (LifeTech, ref. 15596-026) at −80° C. until RNA extraction using the protocol described below.

1.5 RNA Extraction

Total RNA was isolated from tissue sections manually crushed in Trizol™ Reagent (LifeTechnologie, ref. 15596026). After chloroform separation, the RNA was purified using miRNeasy mini Kit (Qiagen, ref. 217004) according to the manufacturer's instruction, with a DNase treatment extra step (Qiagen, ref. 79254). The RNA purity and concentration was assessed using a Nanodrop spectrophotometer and the Agilent 2100 Bioanalyzer System. RNA Integrity Number (RIN) values were mostly >8.

1.6 RT-PCR

Reverse transcription of RNA into cDNA was perfomed using GoScript Reverse Transcriptase kit (Promega, ref. A5001) with a thermocycler Eppendorf (MasterCycler, Pro S). The PCR reactions were carried out in a final volume of 10 μL, containing 2 μL of cDNA template, using an ampliTaq polymerase from LifeTech (Ref. N80800166). For amplification, 40 cycles (at 94° C. for 30 sec, 55 or 60° C. for 30 sec, and 72° C. for 30 sec) were conducted. HLA-G and actin (ATCB) primers are described in Table 1. ATCB amplification was performed as control in all the experiments. The PCR amplification product was mixed with 6× loading dye (Promega, ref. G1881) and analyzed on 2% agarose gel stained with 2 μL of ethidium bromide at 1 mg/mL for 100 mL of agarose gel. The molecular weight marker used was 1 Kb plus DNA ladder from Invitrogen (Ref. 10787018). Imaging was performed using a ChemiDoc XRS System (Biorad), and interpretation using ImageLab software (Biorad).

TABLE 1

PCR primers for RT-PCR experiments

| Gene | SEQ ID NO: | Sequence (5' to 3') |
| --- | --- | --- |
| PrPr F | 77 | 5'-GTAACATAGTGTGGTACTTTG |
| Ex1F | 76 | 5'-CCTGGACTCACACGGAAACT |
| E2 F | 81 | 5'-GGACTCATTCTCCCCAGACG |
| 257 F | 82 | 5'-GGAAGAGGAGACACGGAACA |
| 257 R | 83 | 5'-TGTTCCGTGTCTCCTCTTCC |
| 526 F | 84 | 5'-CCAATGTGGCTGAACAAAGG |
| 526 R | 85 | 5'-CCTTTGTTCAGCCACATTGG |
| 963 R | 86 | 5'-GCAGCTCCAGTGACTACAGC |
| Int1 F | 89 | 5'-GGCCTCAAGCGTGGCTCTCA |
| Int3 F | 78 | 5'-CCCAAGGCGCCTTTACCAAA |
| Int4 R | 75 | 5'-CCACTGCCCCTGGTAC |
| Int5 R | 79 | 5'-AGCCCTCACCACCGACC |
| ATCB F | 87 | 5'-TCCTGTGGCATCCACGAAACT |
| ATCB R | 88 | 5'-GAAGCATTTGCGGTGGACGAT |

1.7 RNA Sequencing

Indexed complementary DNA libraries were prepared from 1 μg of total RNA following the Illumina TRUSEQ protocol. Average size of the AMPure XP beads (Beckman Coulter, Inc.) purified PCR products was 275 bp. The paired-end 150 bp reads sequencing of the transcriptome was performed on equimolar pools of four cDNA libraries on a NextSeq 500 (ILLUMINA).

1.8 High-Throughput Analysis of HLA-G Isoforms

The Ensembl nomenclature will be used throughout the text. Short reads from NGS sequencing were mapped to human Reference Genome NCBI Hg19 using BWA aligner (BWA MEM option) [20]. Low quality mapping reads were filtered out from alignment files and the reads mapping to the HLA-G locus were extracted using samtools (Li et al., 2009). Intron retained detection was performed by selecting reads overlapping an intron and one of the surrounding exons, retention for an intron was assessed only when we detected reads overlapping both 5' and 3' flanking exons. Exon skipping detection was performed by analyzing reads presenting split mapping, searching for discontinuity in the order of mapped exons, eg: a read that is mapped to exon the end of 4 and start of exon 6 but is not mapped to exon 5, presents a skipping of exons. Each read subset was visually validated with IGV [22]. For the retention of intron n, the percentage of reads $p_{ni}$ supporting the event is calculated as the ratio between the reads supporting the events (reads at junction exon n/intron n, internal intronic reads on intron n and reads at junction intron n/exon n+1) and the total number of reads spanning the region where the event occurs (the region starting from the junction between exon n and intron n to the junction between intron n and exon n+1): Let $R(i)$ be the number of reads strictly in region i (the reads are only in region i and do not overlap with other regions) and $R(i, j)$ be the number of reads overlapping both regions i and j. Let $S(i)$ be the number of reads supporting a skipping of exon i (reads overlapping exon n and exon m where m>n+1). The number of reads supporting the retention of intron n is thus $IR_n = R(exon_n, intron_n) + R(intron_n) + R(intron_n, exon_{n+1})$. The total number of reads in the region of the retention of intron n is $T_n = IR_n + R(exon_n, exon_{n+1}) + S(n)$; $p_{ni}$ is thus given by $p_{ni} = IR_n/T_n$.

For the skipping of exon n, the percentage of reads pne supporting the event is given by pne=S(n)/Tn. Analysis of potential biases were assessed by using the TopHat2 aligner [24].

2. Results 2.1 Marked Subcellular Heterogeneity of HLA-G Isoforms Distribution in ccRCC In order to consider HLA-G as a potential target for cancer therapy, the expression of HLA-G in tumor cells derived from patients with ccRCC was assessed. To this end, 3 to 10 sections for each tumor were isolated, according to the tumor size. Microscopy analysis performed on hematoxylin and eosin (H&E) stained slides confirmed a morphologic heterogeneity (FIG. 2, left panel), classically associated with ccRCC [8]. We further dissected this heterogeneity by immunostaining with specific antibodies directed against HLA-G: 4H84, which recognizes an epitope located into the alpha1 domain common to all seven reported HLA-G isoforms and the antibody 5A6G7 that only recognizes soluble HLA-G5 and HLA-G6 isoforms. This antibody targets the amino acids encoded by the retained intron 5 (previously known as intron 4 according to the IMGT/HLA nomenclature). Trophoblastic cells, which express HLA-G at high levels, were used as positive controls.

Even though all tumors expressed HLA-G in at least one area, this expression was distinct between and inside tumors. Tumors of patients 1 and 2 showed a strong immunostaining with 4H84 antibody in all regions. The staining was membranous and cytoplasmic (FIG. 2). Noteworthy, an additional very strong staining of hyaline globules located in the cytoplasm of the tumor cells was also detected. These hyaline globules were well visible on H&E slides and constituted a very uncommon aspect of tumor [9]. On the other hand, using the 5A6G7 antibody, a weak or moderate granular cytoplasmic immunostaining was noticed in the cytoplasm but not in hyaline globules. The expression of HLA-G in tumors from other patients was very different: tumors of patients 6 and 7 presented a diffuse but moderate membrane immunostaining with 4H84 antibody. These two tumors showed no (patient 6) or weak and focal (patient 7) granular intracytoplasmic immunostaining with 5A6G7 which denoted the absence of soluble proteins HLA-G5 and HLA-G6. In two other tumors (patients 4 and 5), the expression of HLA-G evaluated by 4H84 antibody was noted in small microscopic areas of only one tumor region. Of note, the only HLA-G positive area of patient 4's tumor corresponds precisely to intracytoplasmic hyaline globules. No stain was observed in any other region of the tumor.

The immunostaining profiles of tumor cells of patients 3 and 8 were unexpected. No immunostaining was detected with the 4H84 antibody which labels all the reported HLA-G isoforms. The lack of labeling of tumor sections with this antibody normally accounts for the absence of HLA-G expression. However, a diffuse and strong granular intracytoplasmic 5A6G7 immunostaining, and a diffuse, thin and granular intracytoplasmic immunostaining were observed in tumor cells of patients 3 and 8, respectively. This was unpredictable considering our current knowledge on the structure of the seven reported HLA-G isoforms since they all contain the alpha 1 domain recognized by the 4H84 antibody. To try to better understand these differences, we have performed a similar analysis using an antibody that also recognizes the epitope encoded by the retained intron 5 (Ensembl database) present in soluble HLA-G5 and -G6 isoforms named 2A12. The results revealed different and unanticipated immune-staining patterns, notably the labeling of hyaline globules in patients 1 and 2.

Together, the results of the immunohistochemical study clearly demonstrate intra- and inter-heterogeneity of HLA-G expression in ccRCC tumors. However, some immunostaining patterns were unexpected within the boundaries of our prevailing knowledge on the structure of HLA-G isoforms.

2.2 Survey of HLA-G1 Transcripts Expressed in ccRCC

To gain a better insight into the HLA-G isoforms that are expressed in ccRCC and clarify the results of the immunohistochemical analysis, a survey of HLA-G isoform diversity was further assessed by RT-PCR. The tumor sections of the eight patients studied above were amplified with the well-known G257F and G526R primers [10] schematically represented in FIG. 1B. These primers amplify a region that contains the epitope recognized by the 4H84 antibody. Amplification of actin mRNA was performed for each sample as control. A predicted band of 290 bp, specific for the amplification of HLA-G1 transcripts, was found in all tumor sections for patients 1, 2 and 6 whereas this band was only detected in one or two regions of tumors of other patients (FIG. 3). No amplification products were detected in non-tumoral adjacent tissues. Since the sequence of the different isoforms are highly similar and these RT-PCR conditions do not allow the identification of other isoforms like HLA-G2, -G3, -G6 or -G7 which lack exon 4, the target of primer G526, we undertook a large-scale study by RNAseq in order to provide a comprehensive picture of isoforms expressed in ccRCC.

2.3 RNA-Seq Reveals Unannotated HLA-G Transcripts

RNAseq technology provides the most powerful method to analyze expressed isoforms, offering the opportunity to detect alternative splicing events and unannotated transcripts which are essential for understanding development and disease mechanisms in a species [25].

As a first look, we have undertaken the sequencing of four representative samples at a very high depth of coverage (depth>300×). Reads were aligned and quantified according to the Ensembl 70 (GRCh37.p8) reference annotation as described in Material and Methods. Alternative spliced isoforms were mainly categorized into two major groups: exon skipping and intron retention, in which a single exon or intron is alternatively spliced or included out of the mature message.

To verify whether the HLA-G expression patterns of ccRCC patients described above constitute a representative subset of general profiles found in ccRCC patients, we have compared our results to those obtained for the "Cancer Genome of the Kidney" (CAGEKID) cohort which includes a hundred ccRCC patients that were treated in four different European countries (Czech Republic, United Kingdom, Romania and Russia). The data that have been generated constitute a high-quality resource that allowed detecting alternative splicing events with high accuracy (Scelo et al., 2014). Moreover, we have deeply assessed whether common factors such as the choice of the aligner for RNAseq data or the reference sequence to study HLA-G might potentially bias our analysis by using two different aligners, BWA MEM and TopHat2. The results confirmed that the data aligned with BWA MEM or TopHat2 produce similar results (supplementary data). Further, the count of reads at the individual level showed a great similarity between the expression profiles of HLA-G transcripts found in our small cohort of ccRCC patients and that of Cagekid. These results are summarized on Tables 2 and 3 and will be discussed more thoroughly in the following sections.

2.4 Undescribed Intron Retention Events in Expressed HLA-G Transcripts

Intron retention is the rarest type of alternative splicing in mammals and account for only approximately 3% of alternate transcripts [12]. So far, only the retention of intron 3 or intron 5 (previously known as intron 2 and intron 4, according to IMGT/HLA nomenclature) was reported in literature for HLA-G transcripts. Transcripts that retain intron 3 encode HLA-G7 [13] and those retaining intron 5 encode HLA-G5 and HLA-G6 [7].

In our RNAseq analysis, introns subsumed by an exon were labeled as retained. The results, represented graphically on FIG. 4 and summarized in Table 2, showed that reads representing the retention of introns 3 and 5 were the most abundant. In addition, the data support a number of overall new findings that originate from the retention of four additional introns: 1, 4, 6 and 7. To validate the expression of intron-retained transcripts, we first looked for the presence of transcripts containing the intron 1. To this end, we performed RT-PCR amplifications using a strategy described in FIG. 5. First, primer that targets intron 1 (Int1F) was used in combination with G257R, the reverse primer of G257F [13]. Since the presence of introns may be due to contaminating endogenous genomic DNA, all samples were amplified in parallel with actin specific primers located in two different exons. The expected size for the amplification of cDNA derived from mRNA is 320 bp whereas that of genomic DNA is 560 bp. The results show only the amplification of a 320 bp-fragment in all samples, demonstrating the absence of genomic contamination (FIG. 5B, left panel). In view of this result, we further amplified tumor samples using primers Int1F and G257R. An amplified band of the expected size (521 bp) was obtained, consistent with the presence of intron 1 in HLA-G transcripts (FIG. 5-B, right panel). This event was not reported before in literature since the initiation of transcription of HLA-G was solely assigned to exon 2 [26]. We did not detect a PCR amplification band of 649 bp that would correspond to the concomitant retention of intron 2. This is consistent with the results of the RNAseq analysis showing that intron 2 is infrequently retained.

TABLE 2

Number of reads for all observed HLA-G splicing events in ccRCC samples

| | Patient 1 | Patient 3 | Patient 4 | Patient 5 | B00E4I3 | B00E4IS |
|---|---|---|---|---|---|---|
| #reads q30 at HLA-G locus (mean) | 4324 | 1353 | 238 | 142 | 6216 | 5066 |
| exon1 total reads | 6 | 6 | 0 | 0 | 0 | 0 |
| exon2 total reads | 120 | 2 | 0 | 5 | 39 | 15 |
| exon3 total reads | 1344 | 367 | 11 | 11 | 390 | 384 |
| exon4 total reads | 1483 | 260 | 37 | 19 | 1054 | 1078 |
| exon5 total reads | 1397 | 319 | 28 | 21 | 2002 | 1375 |
| exon6 total reads | 449 | 47 | 0 | 11 | 260 | 187 |
| exon7 total reads | 248 | 10 | 0 | 9 | 2 | 6 |
| exon8 total reads | 1079 | 676 | 16 | 25 | 1934 | 1503 |
| retention of intron 1 | 40 | 4 | 1 | 0 | 38 | 12 |
| retention of intron 2 | 0 | 3 | 3 | 0 | 4 | 1 |
| retention of intron 3 | 2 | 101 | 38 | 0 | 36 | 71 |
| retention of intron 4 | 133 | 28 | 2 | 0 | 31 | 84 |
| retention of intron 5 | 148 | 28 | 8 | 0 | 179 | 87 |
| retention of intron 6 | 37 | 46 | 2 | 7 | 35 | 67 |
| retention of intron 7 | 119 | 47 | 0 | 0 | 454 | 96 |
| skipping of exon 4 | 1 | 0 | 0 | 0 | 9 | 7 |
| skipping of exon 5 | 0 | 0 | 0 | 0 | 0 | 0 |
| skipping of exon 6 | 2 | 0 | 0 | 0 | 0 | 0 |
| skipping of exon 7 | 21 | 1 | 0 | 0 | 29 | 31 |
| skipping of exon 4 and 5 | 2 | 0 | 0 | 0 | 3 | 4 |
| skipping of exon 4, 5, 6 and 7 | 0 | 0 | 0 | 0 | 0 | 0 |
| skipping of exon 4, 5 and 7 | 0 | 0 | 0 | 0 | 0 | 0 |
| skipping of exon 5, 6 and 7 | 0 | 0 | 0 | 0 | 0 | 0 |
| skipping of exon 6 and 7 | 2 | 0 | 0 | 0 | 12 | 8 |
| raw count of reads start exon2 | 132 | 15 | 0 | 0 | 0 | 0 |
| raw count of reads start exon3 | 0 | 5 | 0 | 0 | 1 | 23 |
| raw count of reads start exon4 | 0 | 3 | 0 | 0 | 10 | 8 |
| raw count of reads start exon5 | 291 | 67 | 6 | 5 | 10 | 3 |

Patients 1, 3, 4 and 5 are representative samples selected for exploring the diversity of HLA-G isoforms. B00E4I3 and B00E4IS are the two samples with the highest HLA-G expression within the CAGEKID (CAncer GEnome of the KIDney) [14].

Further analysis were conducted to validate the retention of intron 4 (FIG. 5C). To this end, RT-PCR was performed using primer G257F in combination with a primer that specifically targets intron 4 (named int4R). Amplification with these primers generated a DNA fragment of 430 bp (FIG. 5C, left panel), demonstrating the presence of intron 4 in HLA-G transcripts. The size of the amplified band is also consistent with the presence of a concomitant retention of intron 3. To further assess whether the same transcript might retain several introns simultaneously, we have performed a RT-PCR amplification using primer int3F (whose sequence is complementary to a region of intron 3) in combination with primer int4R. The results reveal a DNA fragment of 380 bp, as expected for the retention of introns 3 and 4 in the same transcript (FIG. 5C, middle panel). In addition, amplification with Int3F and Int5R primers generated an amplified band of 725 pb (FIG. 5C, right panel). Of note, the size of this band corresponds to the retention of intron 3 and 5, excluding intron 4. These results clearly demonstrate that tumor samples might express transcripts that retain a single intron and others that retain several different introns which may vary from one transcript to the other. To our knowledge, these events were not previously described.

2.5 Novel HLA-G Transcripts with 5'-Extended End

The RNAseq data further revealed that some of the reads aligned on either side of exon 1 (FIG. 4). Transcripts that originate from this area were not previously reported. In fact, the structure of this region is still a matter of debate since information contained in the Ensembl database suggests that HLA-G transcripts may be initiated at this exon, which is located 5' of the exon 1 defined by IMGT/HLA nomenclature (FIG. 1A). The presence or absence of this exon may result in major modifications which include the promoter localization, the length of the 5'-untranslated region and the transcription/translation initiation site. We assess whether HLA-G transcripts may be initiated in this exon or even upstream by RT-PCR amplification. Two specific primers were designed. Primer Ex1F, whose sequence is complementary to a region located in exon1 (Ensembl database) and primer PrPr, whose sequence is complementary to a region located further upstream currently considered as the promoter region (schematically represented in FIG. 1B). RT-PCR using these two upstream primers in combination with G526R produced two bands of expected sizes: 690 bp (for Ex1F-G526R) and 725 bp (for PrPr-G526R) respectively (data not shown). To verify the specificity of these fragments, amplified DNA samples were sequenced and nucleotide similarities were searched in public databases using BLAST. The results demonstrated a high degree of similarity with HLA-G except for a deletion of 106 bp fragment. Resulting from this deletion, the distance between the ATG located at the end of exon 1 and the one located in exon 2 was reduced from 118 bp to 12 bp (FIG. 6A). As a consequence, the 106-bp deletion brings both ATG in frame. This may now allow the initiation of translation at the ATG located in the first exon and generate a protein that would have a 5'-extended end of five additional amino acids (MKTPR (SEQ ID NO: 1)). At present, the only translation initiation start site was attributed to the ATG located in exon 2 (which corresponds to exon 1 defined by IMGT/HLA nomenclature). This transcript was also found in some of the trophoblast samples tested but not all. This indicates that factors regulating it expression are still to be elucidated.

Altogether these results are consistent with the existence of a novel HLA-G transcript, named HLA-G1L, having an extended 5'-end, which might be co-expressed in trophoblasts and ccRCC tumor cells with previously reported HLA-G isoforms.

2.6 Alternatively Spliced Exons Potentially Generate Novel Soluble HLA-G Isoforms Exon skipping is one of the major forms of alternative splicing, which generates multiple mRNA isoforms differing in the precise combinations of their exon sequences. Here, we define an exon skipping event as a pairing between an exon-containing form and an exon-excluding form, occurring at the same exon and with the same flanking introns. The same exon may be involved in multiple exon skipping events.

For HLA-G, only the skipping of exon 4 (HLA-G2), exon 5 (HLA-G4), or both simultaneously (HLA-G3), were reported in literature. In this study, aligned reads with BWA mem reveal the skipping of exons never uncovered before. The main skipping events are reported in Table 2. We also confirmed these results by using TopHat2.

The highest read coverage was consistent with the skipping of exon 7 alone, which contains the stop codon of the protein. However, no major modifications are expected in the encoded protein lacking this exon since a supplementary in-frame stop codon is found at the beginning of exon 8. Most importantly, skipping of exon 7 concomitantly to exon 6, which encodes the transmembrane domain, is highly relevant since their absence may generate isoforms that lack the transmembrane domain and the cytoplasmic tail and therefore would constitute still unreported soluble proteins.

When RT-PCR was performed with primer G963R, whose sequence is complementary to a region of exon 6, no amplification products could be obtained in combination with the forward primers G257F (exon 3) or G256F (exon 4). However, an expected 290 bp amplified fragment was generated when the primer G257F was used in combination with G526R. Together these results are consistent with HLA-G transcripts that possess exons 3 and 4 but lack exon 6. In addition, when these primers were used to analyze samples from patient 1, amplified bands were obtained using the primer combination G526F-G963R whereas no amplification was detected using G257F-G963R, consistent with the expression of transcripts that lack exon 3.

2.7 Alternative Spliced HLA-G Isoforms Lack the Alpha-1 Domain

Further analysis of RNAseq data reveals that some of the reads might be initiated at exon 4. This was determined by quantifying the raw count of reads within 20 pb upstream of the exon acceptor site. The predicted N-terminal-truncated protein would lack the peptide signal and the alpha1 domain. To assess whether the translation into a protein might start in this region, we have examined the nucleotide sequence of exon 4. This analysis revealed the presence of an in-frame ATG that might serve as a translation initiation codon. Our preliminary results (not shown) reveal that transcripts that lack the alpha-1 domain may lack also the alpha-2 domain and therefore encode only the alpha-3 domain.

Notably, the expression of these isoforms may now provide a hypothesis on the differences of immuno-staining patterns generated following the labeling of some tumor samples with 4H84 and antibodies that have been raised against soluble isoforms, which could not be explained previously within the boundaries of widespread knowledge on the structure of HLA-G isoforms.

TABLE 3

Percentage of transcripts for each splicing event observed

| Alternative splicing events | % overall Samples | median | % overall Samples CAGEKID | median CAGEKID |
|---|---|---|---|---|
| retention of intron 1 | 50 | 100 | 25.97 | 100 |
| retention of intron 2 | 25 | 0 | 41.56 | 0 |
| retention of intron 3 | 50 | 43.9 | 85.71 | 8.62 |
| retention of intron 4 | 50 | 84.85 | 75.32 | 13.89 |
| retention of intron 5 | 75 | 82.35 | 92.21 | 15.62 |

TABLE 3-continued

Percentage of transcripts for each splicing event observed

| Alternative splicing events | % overall Samples | median | % overall Samples CAGEKID | median CAGEKID |
|---|---|---|---|---|
| retention of intron 6 | 75 | 70.66 | 90.91 | 17.02 |
| retention of intron 7 | 50 | 85.62 | 90.91 | 54.17 |
| skipping of exon 4 | 0 | 0 | 38.96 | 0 |
| skipping of exon 6 | 0 | 0 | 31.17 | 0 |
| skipping of exon 7 | 50 | 7.66 | 81.82 | 21.23 |
| skipping of exon 6 and 7 | 0 | 0 | 62.34 | 2.25 |

Percentage of overall samples is the percentage of samples presenting the event.
The last two columns are the same metrics calculated for 77 CAGEKID samples expressing HLA-G.

B. Pro-Tumoral Effect of the HLA-G Isoforms
1. Materials and Methods
1.1 Production of Lentiviruses Expressing HLA-G Isoforms The HLA-G1 and HLA-G1L isoforms were introduced into the plasmid pWPXL (10510 bp), between the BamH1 (3499) and NdeI (4334) sites, just 3' of the EF-1α promoter which directs the expression of two isoforms HLA-G.
For HLA-G1:

The inserted fragment of 3438 bp comprises the HLA-G1 cDNA initiated in the SEQ ID NO. 93 AGTGTGGTACTTT sequence and ending in 3' with the SEQ ID NO. 94 TGGAAGACATGAGAACTTTCCA sequence. This fragment is followed by a "red" variant of the GFP (Aequorea victoria green fluorescent protein jellyfish), named Neptune that has been brought under control of the CMV promoter. Finally, at the 3' end, a molecular barcode was introduced as an integration marker and for in vivo monitoring of metastases (Grosselin et al., Stem Cells, 10: 2162-71, 2013).
For HLA-G1L:

The inserted fragment of 3279 bp comprises the HLA-G1L cDNA initiated at the SEQ ID NO. 95 ATATAGTAACATAGTGT sequence and ending in 3' with the SEQ ID NO. 94 TGGAAGACATGAGAACTTTCCA sequence. This fragment is followed by a "blue" (cyan) variant of GFP, the ECFP which has a bimodal excitation and emission spectrum at 433/445 nm and 475/503 nm leading to a fluorochrome with a gloss and improved photostability. ECFP was put under control of the CMV promoter. Finally, at the 3' end, a molecular barcode was introduced as integration marker and for in vivo monitoring of metastases (Grosselin et al., Stem Cells, 10: 2162-71, 2013).

These 2 plasmids were used to produce lentivirus WPXL ΔU3 SIN, envelope VSV-G, OGM group II, class 2 at 1.20E+08 TU (Transduction Unit)/ml.
2. Results Each lentivirus contains a different HLA-G isoform. The lentiviruses were transduced in a line of renal cell carcinoma clear (cells RCC7) lineage perfectly characterized, not expressing HLA-G. For each isoform, two independent transductions were performed to increase the reliability and robustness of our results.

An intradermal injection was performed of each of the RCC7 cell lines transduced, into 5 NSG mice per condition. Non-transduced RCC7 cells are used as a control.

After intradermal injection of the cells, tumor/metastatic growth was evaluated regularly.

At the time of sacrifice of the mice, tumors metastases, and different tissues were removed, for immunohistochemical and expression (RNA) analysis. Each isoform is associated with a barcode, making it possible to ensure that the tumors and metastases obtained come from the injected cells.

As can be seen in FIG. 7, the xenografted mice from the cells from the RCC7 line bearing the long HLA-G1L isoform showed at J 38, a more marked tumor growth, at least partially linked to a more developed intra and perituomoral neovascularization. No intra-tumoral necrotic reworking is observed in these tumors, unlike those resulting from the RCC7 line carrying the HLA-G1 isoform.

Similar experiments were done with nude mice. FIG. 8A shows the pictures of nude mice xenografted with RCC7 cells expressing either GFP, HLA-G1 or HLA-G1L, on day 25 after injection. FIG. 8B shows the pictures of nude mice xenografted with RCC7 cells grown on matrigel and expressing either GFP, HLA-G1 or HLA-G1L, on day 25 after injection.

C. Pro-Angiogenic Effect of the HLA-G Isoforms

RCC7 cells expressing either GFP, HLA-G1 or HLA-G1L were prepared as disclosed above (point B).

The left ear of NSG mice were injected with control (RCC7 cells expressing GFP), while their right ear were injected with RCC7 cells expressing either HLA-G1 or HLA-G1L. Pictures were taken on day 8. The results are shown in FIG. 9 (control RCC7 cells vs HLA-G1L) and in FIG. 10 (control RCC7 cells vs HLA-G1).

The results demonstrate a pro-angiogenic effect of the expression of HLA-G1L, which is not reproduced by the expression of HLA-G1.

REFERENCES

1. Rouas-Freiss, N., et al., Direct evidence to support the role of HLA-G in protecting the fetus from maternal uterine natural killer cytolysis. Proc Natl Acad Sci USA, 1997. 94(21): p. 11520-5.
2. Ibrahim, E. C., et al., Tumor-specific up-regulation of the nonclassical class I HLA-G antigen expression in renal carcinoma. Cancer Res, 2001. 61(18): p. 6838-45.
3. Bukur, J., et al., Functional role of human leukocyte antigen-G up-regulation in renal cell carcinoma. Cancer Res, 2003. 63(14): p. 4107-11.
4. Brugarolas, J., Molecular genetics of clear-cell renal cell carcinoma. J Clin Oncol, 2014. 32(18): p. 1968-76.
5. Agaugue, S., E. D. Carosella, and N. Rouas-Freiss, Role of HLA-G in tumor escape through expansion of myeloid-derived suppressor cells and cytokinic balance in favor of Th2 versus Th1/Th17. Blood, 2011. 117(26): p. 7021-31.
6. Loumagne, L., et al., In vivo evidence that secretion of HLA-G by immunogenic tumor cells allows their evasion from immunosurveillance. Int J Cancer, 2014. 135(9): p. 2107-17.
7. Fujii, T., A. Ishitani, and D. E. Geraghty, A soluble form of the HLA-G antigen is encoded by a messenger ribonucleic acid containing intron 4. J Immunol, 1994. 153 (12): p. 5516-24.
8. Moch, H., et al., The 2016 WHO Classification of Tumours of the Urinary System and Male Genital Organs-Part A: Renal, Penile, and Testicular Tumours. Eur Urol, 2016. 70(1): p. 93-105.
9. Krishnan, B. and L. D. Truong, Renal epithelial neoplasms: the diagnostic implications of electron microscopic study in 55 cases. Hum Pathol, 2002. 33(1): p. 68-79.
10. Paul, P., et al., HLA-G, -E, -F preworkshop: tools and protocols for analysis of non-classical class I genes transcription and protein expression. Hum Immunol, 2000. 61(11): p. 1177-95.

11. Woolard, J., et al., Molecular diversity of VEGF-A as a regulator of its biological activity. Microcirculation, 2009. 16(7): p. 572-92.
12. Wong, J. J., et al., Intron retention in mRNA: No longer nonsense: Known and putative roles of intron retention in normal and disease biology. Bioessays, 2016. 38(1): p. 41-9.
13. Paul, P., et al., Identification of HLA-G7 as a new splice variant of the HLA-G mRNA and expression of soluble HLA-G5, -G6, and -G7 transcripts in human transfected cells. Hum Immunol, 2000. 61(11): p. 1138-49.
14. Scelo, G., et al., Variation in genomic landscape of clear cell renal cell carcinoma across Europe. Nat Commun, 2014. 5: p. 5135.
15. Nayar, R., E. Bourtsos, and D. V. DeFrias, Hyaline globules in renal cell carcinoma and hepatocellular carcinoma. A clue or a diagnostic pitfall on fine-needle aspiration? Am J Clin Pathol, 2000. 114(4): p. 576-82.
16. Gerlinger, M., et al., Genomic architecture and evolution of clear cell renal cell carcinomas defined by multiregion sequencing. Nat Genet, 2014. 46(3): p. 225-33.
17. Carosella, E. D., et al., HLA-G and HLA-E: fundamental and pathophysiological aspects. Immunol Today, 2000. 21(11): p. 532-4.
18. Hoare, H. L., et al., Subtle changes in peptide conformation profoundly affect recognition of the non-classical MHC class I molecule HLA-E by the CD94-NKG2 natural killer cell receptors. J Mol Biol, 2008. 377(5): p. 1297-303.
19. Kraemer, T., et al., HLA-E: Presentation of a Broader Peptide Repertoire Impacts the Cellular Immune Response-Implications on HSCT Outcome. Stem Cells hit, 2015. 2015: p. 346714.
20. Li, H. and R. Durbin, Fast and accurate short read alignment with Burrows-Wheeler transform. Bioinformatics, 2009. 25(14): p. 1754-60.
21. Li, H., et al., The Sequence Alignment/Map format and SAMtools. Bioinformatics, 2009. 25(16): p. 2078-9.
22. Robinson, J. T., et al., Integrative genomics viewer. Nat Biotechnol, 2011. 29(1): p. 24-6.
23. Morandi, F., et al., Recent Advances in Our Understanding of HLA-G Biology: Lessons from a Wide Spectrum of Human Diseases; Journal of Immunology Research, vol. 2016, Article ID 4326495, 2016.
24. Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome biology 14, R36.
25. Wang, E. T., Sandberg, R., Luo, S., Khrebtukova, I., Zhang, L., Mayr, C., Kingsmore, S. F., Schroth, G. P., and Burge, C. B. (2008). Alternative isoform regulation in human tissue transcriptomes. Nature 456, 470-476.
26. Geraghty, D. E., Koller, B. H., and Orr, H. T. (1987). A human major histocompatibility complex class I gene that encodes a protein with a shortened cytoplasmic segment. Proceedings of the National Academy of Sciences of the United States of America 84, 9145-9149.
27. Tatusova et al, "Blast 2 sequences—a new tool for comparing protein and nucleotide sequences", FEMS Microbiol, 1999, Lett. 174:247-250.
28. Fons, P., Chabot, S., Cartwright, J. E., Lenfant, F., L'Faqihi, F., Giustiniani, J., Herault, J., Gueguen, G., Bono, F., Savi, P., Aguerre-Girr, M., Fournel, S., Malecaze, F., Bensussan, A., Plouët, J., & Le Bouteiller, P. (2006). Soluble HLA-G1 inhibits angiogenesis through an apoptotic pathway and by direct binding to CD160 receptor expressed by endothelial cells. Blood, 108(8), 2608-2615.
29. Tronik-Le Roux D, Renard J, Vérine J, et al. Novel landscape of HLA-G isoforms expressed in clear cell renal cell carcinoma patients. Molecular Oncology. 2017; 11(11):1561-1578.

The invention claimed is:

1. A method of treating ischemia, comprising administering to a subject in need thereof a therapeutically effective amount of an isolated HLA-G protein, wherein the sequence of the isolated HLA-G protein is devoid of transmembrane/cytoplasmic domain and comprises or consists of a sequence selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 21, SEQ ID NO: 23, SEQ ID NO: 25, SEQ ID NO: 27, SEQ ID NO: 28, and SEQ ID NO: 30.

2. The method of claim 1, wherein the ischemia is ischemia associated with a cardiovascular disease, a peripheral artery disease or stroke.

* * * * *

SEQUENCE LISTING

```
<160> NUMBER OF SEQ ID NOS: 95

<210> SEQ ID NO 1
<211> LENGTH: 5
<212> TYPE: PRT
<213> ORGANISM: Homo sapiens

<400> SEQUENCE: 1

Met Lys Thr Pro Arg
1               5

<210> SEQ ID NO 2
<211> LENGTH: 24
<212> TYPE: PRT
<213> ORGANISM: Homo sapiens

<400> SEQUENCE: 2

Met Val Val Met Ala Pro Arg Thr Leu Phe Leu Leu Leu Ser Gly Ala
1               5                  10                  15

Leu Thr Leu Thr Glu Thr Trp Ala
            20

<210> SEQ ID NO 3
<211> LENGTH: 90
<212> TYPE: PRT
<213> ORGANISM: Homo sapiens
```

<400> SEQUENCE: 3

Gly Ser His Ser Met Arg Tyr Phe Ser Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Thr
    50                  55                  60

Arg Asn Thr Lys Ala His Ala Gln Thr Asp Arg Met Asn Leu Gln Thr
65                  70                  75                  80

Leu Arg Gly Tyr Tyr Asn Gln Ser Glu Ala
                85                  90

<210> SEQ ID NO 4
<211> LENGTH: 92
<212> TYPE: PRT
<213> ORGANISM: Homo sapiens

<400> SEQUENCE: 4

Ser Ser His Thr Leu Gln Trp Met Ile Gly Cys Asp Leu Gly Ser Asp
1               5                   10                  15

Gly Arg Leu Leu Arg Gly Tyr Glu Gln Tyr Ala Tyr Asp Gly Lys Asp
            20                  25                  30

Tyr Leu Ala Leu Asn Glu Asp Leu Arg Ser Trp Thr Ala Ala Asp Thr
        35                  40                  45

Ala Ala Gln Ile Ser Lys Arg Lys Cys Glu Ala Ala Asn Val Ala Glu
    50                  55                  60

Gln Arg Arg Ala Tyr Leu Glu Gly Thr Cys Val Glu Trp Leu His Arg
65                  70                  75                  80

Tyr Leu Glu Asn Gly Lys Glu Met Leu Gln Arg Ala
                85                  90

<210> SEQ ID NO 5
<211> LENGTH: 92
<212> TYPE: PRT
<213> ORGANISM: Homo sapiens

<400> SEQUENCE: 5

Asp Pro Pro Lys Thr His Val Thr His His Pro Val Phe Asp Tyr Glu
1               5                   10                  15

Ala Thr Leu Arg Cys Trp Ala Leu Gly Phe Tyr Pro Ala Glu Ile Ile
            20                  25                  30

Leu Thr Trp Gln Arg Asp Gly Glu Asp Gln Thr Gln Asp Val Glu Leu
        35                  40                  45

Val Glu Thr Arg Pro Ala Gly Asp Gly Thr Phe Gln Lys Trp Ala Ala
    50                  55                  60

Val Val Val Pro Ser Gly Glu Glu Gln Arg Tyr Thr Cys His Val Gln
65                  70                  75                  80

His Glu Gly Leu Pro Glu Pro Leu Met Leu Arg Trp
                85                  90

<210> SEQ ID NO 6
<211> LENGTH: 40
<212> TYPE: PRT
<213> ORGANISM: Homo sapiens

<400> SEQUENCE: 6

```
Lys Gln Ser Ser Leu Pro Thr Ile Pro Ile Met Gly Ile Val Ala Gly
1               5                   10                  15

Leu Val Val Leu Ala Ala Val Val Thr Gly Ala Ala Val Ala Ala Val
            20                  25                  30

Leu Trp Arg Lys Lys Ser Ser Asp
        35                  40

<210> SEQ ID NO 7
<211> LENGTH: 343
<212> TYPE: PRT
<213> ORGANISM: Homo sapiens

<400> SEQUENCE: 7

Met Lys Thr Pro Arg Met Val Val Met Ala Pro Arg Thr Leu Phe Leu
1               5                   10                  15

Leu Leu Ser Gly Ala Leu Thr Leu Thr Glu Thr Trp Ala Gly Ser His
            20                  25                  30

Ser Met Arg Tyr Phe Ser Ala Ala Val Ser Arg Pro Gly Arg Gly Glu
        35                  40                  45

Pro Arg Phe Ile Ala Met Gly Tyr Val Asp Asp Thr Gln Phe Val Arg
    50                  55                  60

Phe Asp Ser Asp Ser Ala Cys Pro Arg Met Glu Pro Arg Ala Pro Trp
65                  70                  75                  80

Val Glu Gln Glu Gly Pro Glu Tyr Trp Glu Gly Glu Thr Arg Asn Thr
                85                  90                  95

Lys Ala His Ala Gln Thr Asp Arg Met Asn Leu Gln Thr Leu Arg Gly
            100                 105                 110

Tyr Tyr Asn Gln Ser Glu Ala Ser Ser His Thr Leu Gln Trp Met Ile
        115                 120                 125

Gly Cys Asp Leu Gly Ser Asp Gly Arg Leu Leu Arg Gly Tyr Glu Gln
    130                 135                 140

Tyr Ala Tyr Asp Gly Lys Asp Tyr Leu Ala Leu Asn Glu Asp Leu Arg
145                 150                 155                 160

Ser Trp Thr Ala Ala Asp Thr Ala Ala Gln Ile Ser Lys Arg Lys Cys
                165                 170                 175

Glu Ala Ala Asn Val Ala Glu Gln Arg Arg Ala Tyr Leu Glu Gly Thr
            180                 185                 190

Cys Val Glu Trp Leu His Arg Tyr Leu Glu Asn Gly Lys Glu Met Leu
        195                 200                 205

Gln Arg Ala Asp Pro Pro Lys Thr His Val Thr His His Pro Val Phe
    210                 215                 220

Asp Tyr Glu Ala Thr Leu Arg Cys Trp Ala Leu Gly Phe Tyr Pro Ala
225                 230                 235                 240

Glu Ile Ile Leu Thr Trp Gln Arg Asp Gly Glu Asp Gln Thr Gln Asp
                245                 250                 255

Val Glu Leu Val Glu Thr Arg Pro Ala Gly Asp Gly Thr Phe Gln Lys
            260                 265                 270

Trp Ala Ala Val Val Pro Ser Gly Glu Glu Gln Arg Tyr Thr Cys
        275                 280                 285

His Val Gln His Glu Gly Leu Pro Glu Pro Leu Met Leu Arg Trp Lys
    290                 295                 300

Gln Ser Ser Leu Pro Thr Ile Pro Ile Met Gly Ile Val Ala Gly Leu
305                 310                 315                 320

Val Val Leu Ala Ala Val Val Thr Gly Ala Ala Val Ala Ala Val Leu
```

<210> SEQ ID NO 8
<211> LENGTH: 304
<212> TYPE: PRT
<213> ORGANISM: Homo sapiens

<400> SEQUENCE: 8

Met Lys Thr Pro Arg Met Val Val Met Ala Pro Arg Thr Leu Phe Leu
1               5                   10                  15

Leu Leu Ser Gly Ala Leu Thr Leu Thr Glu Thr Trp Ala Gly Ser His
            20                  25                  30

Ser Met Arg Tyr Phe Ser Ala Ala Val Ser Arg Pro Gly Arg Gly Glu
        35                  40                  45

Pro Arg Phe Ile Ala Met Gly Tyr Val Asp Asp Thr Gln Phe Val Arg
    50                  55                  60

Phe Asp Ser Asp Ser Ala Cys Pro Arg Met Glu Pro Arg Ala Pro Trp
65                  70                  75                  80

Val Glu Gln Glu Gly Pro Glu Tyr Trp Glu Glu Thr Arg Asn Thr
            85                  90                  95

Lys Ala His Ala Gln Thr Asp Arg Met Asn Leu Gln Thr Leu Arg Gly
            100                 105                 110

Tyr Tyr Asn Gln Ser Glu Ala Ser Ser His Thr Leu Gln Trp Met Ile
        115                 120                 125

Gly Cys Asp Leu Gly Ser Asp Gly Arg Leu Leu Arg Gly Tyr Glu Gln
    130                 135                 140

Tyr Ala Tyr Asp Gly Lys Asp Tyr Leu Ala Leu Asn Glu Asp Leu Arg
145                 150                 155                 160

Ser Trp Thr Ala Ala Asp Thr Ala Ala Gln Ile Ser Lys Arg Lys Cys
                165                 170                 175

Glu Ala Ala Asn Val Ala Glu Gln Arg Arg Ala Tyr Leu Glu Gly Thr
            180                 185                 190

Cys Val Glu Trp Leu His Arg Tyr Leu Glu Asn Gly Lys Glu Met Leu
        195                 200                 205

Gln Arg Ala Asp Pro Pro Lys Thr His Val Thr His His Pro Val Phe
    210                 215                 220

Asp Tyr Glu Ala Thr Leu Arg Cys Trp Ala Leu Gly Phe Tyr Pro Ala
225                 230                 235                 240

Glu Ile Ile Leu Thr Trp Gln Arg Asp Gly Glu Asp Gln Thr Gln Asp
                245                 250                 255

Val Glu Leu Val Glu Thr Arg Pro Ala Gly Asp Gly Thr Phe Gln Lys
            260                 265                 270

Trp Ala Ala Val Val Pro Ser Gly Glu Glu Gln Arg Tyr Thr Cys
        275                 280                 285

His Val Gln His Glu Gly Leu Pro Glu Pro Leu Met Leu Arg Trp Met
    290                 295                 300

<210> SEQ ID NO 9
<211> LENGTH: 253
<212> TYPE: PRT
<213> ORGANISM: Homo sapiens

<400> SEQUENCE: 9

Met Lys Thr Pro Arg Met Val Val Met Ala Pro Arg Thr Leu Phe Leu

-continued

```
                1               5                  10                  15
            Leu Leu Ser Gly Ala Leu Thr Leu Thr Glu Thr Trp Ala Gly Ser His
                            20                  25                  30

Thr Leu Gln Trp Met Ile Gly Cys Asp Leu Gly Ser Asp Gly Arg Leu
                            35                  40                  45

Leu Arg Gly Tyr Glu Gln Tyr Ala Tyr Asp Gly Lys Asp Tyr Leu Ala
                            50                  55                  60

Leu Asn Glu Asp Leu Arg Ser Trp Thr Ala Ala Asp Thr Ala Ala Gln
             65                 70                  75                  80

Ile Ser Lys Arg Lys Cys Glu Ala Ala Asn Val Ala Glu Gln Arg Arg
                            85                  90                  95

Ala Tyr Leu Glu Gly Thr Cys Val Glu Trp Leu His Arg Tyr Leu Glu
                           100                 105                 110

Asn Gly Lys Glu Met Leu Gln Arg Ala Asp Pro Pro Lys Thr His Val
                           115                 120                 125

Thr His His Pro Val Phe Asp Tyr Glu Ala Thr Leu Arg Cys Trp Ala
                       130                 135                 140

Leu Gly Phe Tyr Pro Ala Glu Ile Ile Leu Thr Trp Gln Arg Asp Gly
            145                 150                 155                 160

Glu Asp Gln Thr Gln Asp Val Glu Leu Val Glu Thr Arg Pro Ala Gly
                           165                 170                 175

Asp Gly Thr Phe Gln Lys Trp Ala Ala Val Val Val Pro Ser Gly Glu
                       180                 185                 190

Glu Gln Arg Tyr Thr Cys His Val Gln His Glu Gly Leu Pro Glu Pro
                       195                 200                 205

Leu Met Leu Arg Trp Lys Gln Ser Ser Leu Pro Thr Ile Pro Ile Met
                       210                 215                 220

Gly Ile Val Ala Gly Leu Val Val Leu Ala Ala Val Val Thr Gly Ala
            225                 230                 235                 240

Ala Val Ala Ala Val Leu Trp Arg Lys Lys Ser Ser Asp
                           245                 250

<210> SEQ ID NO 10
<211> LENGTH: 214
<212> TYPE: PRT
<213> ORGANISM: Homo sapiens

<400> SEQUENCE: 10

Met Lys Thr Pro Arg Met Val Val Met Ala Pro Arg Thr Leu Phe Leu
             1                  5                  10                  15

Leu Leu Ser Gly Ala Leu Thr Leu Thr Glu Thr Trp Ala Gly Ser His
                            20                  25                  30

Thr Leu Gln Trp Met Ile Gly Cys Asp Leu Gly Ser Asp Gly Arg Leu
                            35                  40                  45

Leu Arg Gly Tyr Glu Gln Tyr Ala Tyr Asp Gly Lys Asp Tyr Leu Ala
                            50                  55                  60

Leu Asn Glu Asp Leu Arg Ser Trp Thr Ala Ala Asp Thr Ala Ala Gln
             65                 70                  75                  80

Ile Ser Lys Arg Lys Cys Glu Ala Ala Asn Val Ala Glu Gln Arg Arg
                            85                  90                  95

Ala Tyr Leu Glu Gly Thr Cys Val Glu Trp Leu His Arg Tyr Leu Glu
                           100                 105                 110

Asn Gly Lys Glu Met Leu Gln Arg Ala Asp Pro Pro Lys Thr His Val
                           115                 120                 125
```

Thr His His Pro Val Phe Asp Tyr Glu Ala Thr Leu Arg Cys Trp Ala
130                 135                 140

Leu Gly Phe Tyr Pro Ala Glu Ile Ile Leu Thr Trp Gln Arg Asp Gly
145                 150                 155                 160

Glu Asp Gln Thr Gln Asp Val Glu Leu Val Glu Thr Arg Pro Ala Gly
                165                 170                 175

Asp Gly Thr Phe Gln Lys Trp Ala Ala Val Val Pro Ser Gly Glu
            180                 185                 190

Glu Gln Arg Tyr Thr Cys His Val Gln His Glu Gly Leu Pro Glu Pro
                195                 200                 205

Leu Met Leu Arg Trp Met
        210

<210> SEQ ID NO 11
<211> LENGTH: 161
<212> TYPE: PRT
<213> ORGANISM: Homo sapiens

<400> SEQUENCE: 11

Met Lys Thr Pro Arg Met Val Val Met Ala Pro Arg Thr Leu Phe Leu
1               5                   10                  15

Leu Leu Ser Gly Ala Leu Thr Leu Thr Glu Thr Trp Ala Gly Ser His
                20                  25                  30

Thr Leu Gln Trp Met Ile Gly Cys Asp Leu Gly Ser Asp Gly Arg Leu
            35                  40                  45

Leu Arg Gly Tyr Glu Gln Tyr Ala Tyr Asp Gly Lys Asp Tyr Leu Ala
        50                  55                  60

Leu Asn Glu Asp Leu Arg Ser Trp Thr Ala Ala Asp Thr Ala Ala Gln
65                  70                  75                  80

Ile Ser Lys Arg Lys Cys Glu Ala Ala Asn Val Ala Glu Gln Arg Arg
                85                  90                  95

Ala Tyr Leu Glu Gly Thr Cys Val Glu Trp Leu His Arg Tyr Leu Glu
            100                 105                 110

Asn Gly Lys Glu Met Leu Gln Arg Ala Glu Gln Ser Ser Leu Pro Thr
        115                 120                 125

Ile Pro Ile Met Gly Ile Val Ala Gly Leu Val Val Leu Ala Ala Val
130                 135                 140

Val Thr Gly Ala Ala Val Ala Ala Val Leu Trp Arg Lys Lys Ser Ser
145                 150                 155                 160

Asp

<210> SEQ ID NO 12
<211> LENGTH: 122
<212> TYPE: PRT
<213> ORGANISM: Homo sapiens

<400> SEQUENCE: 12

Met Lys Thr Pro Arg Met Val Val Met Ala Pro Arg Thr Leu Phe Leu
1               5                   10                  15

Leu Leu Ser Gly Ala Leu Thr Leu Thr Glu Thr Trp Ala Gly Ser His
                20                  25                  30

Thr Leu Gln Trp Met Ile Gly Cys Asp Leu Gly Ser Asp Gly Arg Leu
            35                  40                  45

Leu Arg Gly Tyr Glu Gln Tyr Ala Tyr Asp Gly Lys Asp Tyr Leu Ala
        50                  55                  60

Leu Asn Glu Asp Leu Arg Ser Trp Thr Ala Ala Asp Thr Ala Ala Gln

```
                   65                  70                  75                  80
Ile Ser Lys Arg Lys Cys Glu Ala Ala Asn Val Ala Glu Gln Arg Arg
                    85                  90                  95

Ala Tyr Leu Glu Gly Thr Cys Val Glu Trp Leu His Arg Tyr Leu Glu
                100                 105                 110

Asn Gly Lys Glu Met Leu Gln Arg Ala Val
            115                 120

<210> SEQ ID NO 13
<211> LENGTH: 161
<212> TYPE: PRT
<213> ORGANISM: Homo sapiens

<400> SEQUENCE: 13

Met Lys Thr Pro Arg Met Val Val Met Ala Pro Arg Thr Leu Phe Leu
1               5                   10                  15

Leu Leu Ser Gly Ala Leu Thr Leu Thr Glu Thr Trp Ala Asp Pro Pro
                20                  25                  30

Lys Thr His Val Thr His His Pro Val Phe Asp Tyr Glu Ala Thr Leu
            35                  40                  45

Arg Cys Trp Ala Leu Gly Phe Tyr Pro Ala Glu Ile Ile Leu Thr Trp
        50                  55                  60

Gln Arg Asp Gly Glu Asp Gln Thr Gln Asp Val Glu Leu Val Glu Thr
65                  70                  75                  80

Arg Pro Ala Gly Asp Gly Thr Phe Gln Lys Trp Ala Ala Val Val Val
                85                  90                  95

Pro Ser Gly Glu Glu Gln Arg Tyr Thr Cys His Val Gln His Glu Gly
                100                 105                 110

Leu Pro Glu Pro Leu Met Leu Arg Trp Lys Gln Ser Ser Leu Pro Thr
            115                 120                 125

Ile Pro Ile Met Gly Ile Val Ala Gly Leu Val Val Leu Ala Ala Val
        130                 135                 140

Val Thr Gly Ala Ala Val Ala Ala Val Leu Trp Arg Lys Lys Ser Ser
145                 150                 155                 160

Asp

<210> SEQ ID NO 14
<211> LENGTH: 122
<212> TYPE: PRT
<213> ORGANISM: Homo sapiens

<400> SEQUENCE: 14

Met Lys Thr Pro Arg Met Val Val Met Ala Pro Arg Thr Leu Phe Leu
1               5                   10                  15

Leu Leu Ser Gly Ala Leu Thr Leu Thr Glu Thr Trp Ala Asp Pro Pro
                20                  25                  30

Lys Thr His Val Thr His His Pro Val Phe Asp Tyr Glu Ala Thr Leu
            35                  40                  45

Arg Cys Trp Ala Leu Gly Phe Tyr Pro Ala Glu Ile Ile Leu Thr Trp
        50                  55                  60

Gln Arg Asp Gly Glu Asp Gln Thr Gln Asp Val Glu Leu Val Glu Thr
65                  70                  75                  80

Arg Pro Ala Gly Asp Gly Thr Phe Gln Lys Trp Ala Ala Val Val Val
                85                  90                  95

Pro Ser Gly Glu Glu Gln Arg Tyr Thr Cys His Val Gln His Glu Gly
                100                 105                 110
```

```
Leu Pro Glu Pro Leu Met Leu Arg Trp Met
        115                 120
```

<210> SEQ ID NO 15
<211> LENGTH: 159
<212> TYPE: PRT
<213> ORGANISM: Homo sapiens
<400> SEQUENCE: 15

```
Met Lys Thr Pro Arg Met Val Val Met Ala Pro Arg Thr Leu Phe Leu
1               5                   10                  15

Leu Leu Ser Gly Ala Leu Thr Leu Thr Glu Thr Trp Ala Gly Ser His
            20                  25                  30

Ser Met Arg Tyr Phe Ser Ala Ala Val Ser Arg Pro Gly Arg Gly Glu
        35                  40                  45

Pro Arg Phe Ile Ala Met Gly Tyr Val Asp Asp Thr Gln Phe Val Arg
    50                  55                  60

Phe Asp Ser Asp Ser Ala Cys Pro Arg Met Glu Pro Arg Ala Pro Trp
65                  70                  75                  80

Val Glu Gln Glu Gly Pro Glu Tyr Trp Glu Glu Glu Thr Arg Asn Thr
                85                  90                  95

Lys Ala His Ala Gln Thr Asp Arg Met Asn Leu Gln Thr Leu Arg Gly
            100                 105                 110

Tyr Tyr Asn Gln Ser Glu Ala Lys Gln Ser Ser Leu Pro Thr Ile Pro
        115                 120                 125

Ile Met Gly Ile Val Ala Gly Leu Val Val Leu Ala Ala Val Val Thr
    130                 135                 140

Gly Ala Ala Val Ala Ala Val Leu Trp Arg Lys Lys Ser Ser Asp
145                 150                 155
```

<210> SEQ ID NO 16
<211> LENGTH: 120
<212> TYPE: PRT
<213> ORGANISM: Homo sapiens
<400> SEQUENCE: 16

```
Met Lys Thr Pro Arg Met Val Val Met Ala Pro Arg Thr Leu Phe Leu
1               5                   10                  15

Leu Leu Ser Gly Ala Leu Thr Leu Thr Glu Thr Trp Ala Gly Ser His
            20                  25                  30

Ser Met Arg Tyr Phe Ser Ala Ala Val Ser Arg Pro Gly Arg Gly Glu
        35                  40                  45

Pro Arg Phe Ile Ala Met Gly Tyr Val Asp Asp Thr Gln Phe Val Arg
    50                  55                  60

Phe Asp Ser Asp Ser Ala Cys Pro Arg Met Glu Pro Arg Ala Pro Trp
65                  70                  75                  80

Val Glu Gln Glu Gly Pro Glu Tyr Trp Glu Glu Glu Thr Arg Asn Thr
                85                  90                  95

Lys Ala His Ala Gln Thr Asp Arg Met Asn Leu Gln Thr Leu Arg Gly
            100                 105                 110

Tyr Tyr Asn Gln Ser Glu Ala Met
        115                 120
```

<210> SEQ ID NO 17
<211> LENGTH: 137
<212> TYPE: PRT
<213> ORGANISM: Homo sapiens

<400> SEQUENCE: 17

Met Leu Gln Arg Ala Asp Pro Pro Lys Thr His Val Thr His His Pro
1               5                   10                  15

Val Phe Asp Tyr Glu Ala Thr Leu Arg Cys Trp Ala Leu Gly Phe Tyr
                20                  25                  30

Pro Ala Glu Ile Ile Leu Thr Trp Gln Arg Asp Gly Glu Asp Gln Thr
            35                  40                  45

Gln Asp Val Glu Leu Val Glu Thr Arg Pro Ala Gly Asp Gly Thr Phe
    50                  55                  60

Gln Lys Trp Ala Ala Val Val Val Pro Ser Gly Glu Glu Gln Arg Tyr
65                  70                  75                  80

Thr Cys His Val Gln His Glu Gly Leu Pro Glu Pro Leu Met Leu Arg
                85                  90                  95

Trp Lys Gln Ser Ser Leu Pro Thr Ile Pro Ile Met Gly Ile Val Ala
                100                 105                 110

Gly Leu Val Val Leu Ala Ala Val Val Thr Gly Ala Ala Val Ala Ala
            115                 120                 125

Val Leu Trp Arg Lys Lys Ser Ser Asp
        130                 135

<210> SEQ ID NO 18
<211> LENGTH: 98
<212> TYPE: PRT
<213> ORGANISM: Homo sapiens

<400> SEQUENCE: 18

Met Leu Gln Arg Ala Asp Pro Pro Lys Thr His Val Thr His His Pro
1               5                   10                  15

Val Phe Asp Tyr Glu Ala Thr Leu Arg Cys Trp Ala Leu Gly Phe Tyr
                20                  25                  30

Pro Ala Glu Ile Ile Leu Thr Trp Gln Arg Asp Gly Glu Asp Gln Thr
            35                  40                  45

Gln Asp Val Glu Leu Val Glu Thr Arg Pro Ala Gly Asp Gly Thr Phe
    50                  55                  60

Gln Lys Trp Ala Ala Val Val Val Pro Ser Gly Glu Glu Gln Arg Tyr
65                  70                  75                  80

Thr Cys His Val Gln His Glu Gly Leu Pro Glu Pro Leu Met Leu Arg
                85                  90                  95

Trp Met

<210> SEQ ID NO 19
<211> LENGTH: 217
<212> TYPE: PRT
<213> ORGANISM: Homo sapiens

<400> SEQUENCE: 19

Met Ile Gly Cys Asp Leu Gly Ser Asp Gly Arg Leu Leu Arg Gly Tyr
1               5                   10                  15

Glu Gln Tyr Ala Tyr Asp Gly Lys Asp Tyr Leu Ala Leu Asn Glu Asp
                20                  25                  30

Leu Arg Ser Trp Thr Ala Ala Asp Thr Ala Ala Gln Ile Ser Lys Arg
            35                  40                  45

Lys Cys Glu Ala Ala Asn Val Ala Glu Gln Arg Arg Ala Tyr Leu Glu
    50                  55                  60

Gly Thr Cys Val Glu Trp Leu His Arg Tyr Leu Glu Asn Gly Lys Glu

```
                65                  70                  75                  80
Met Leu Gln Arg Ala Asp Pro Pro Lys Thr His Val Thr His His Pro
                    85                  90                  95

Val Phe Asp Tyr Glu Ala Thr Leu Arg Cys Trp Ala Leu Gly Phe Tyr
                    100                 105                 110

Pro Ala Glu Ile Ile Leu Thr Trp Gln Arg Asp Gly Glu Asp Gln Thr
                    115                 120                 125

Gln Asp Val Glu Leu Val Glu Thr Arg Pro Ala Gly Asp Gly Thr Phe
                    130                 135                 140

Gln Lys Trp Ala Ala Val Val Val Pro Ser Gly Glu Glu Gln Arg Tyr
145                 150                 155                 160

Thr Cys His Val Gln His Glu Gly Leu Pro Glu Pro Leu Met Leu Arg
                    165                 170                 175

Trp Lys Gln Ser Ser Leu Pro Thr Ile Pro Ile Met Gly Ile Val Ala
                    180                 185                 190

Gly Leu Val Val Leu Ala Ala Val Val Thr Gly Ala Ala Val Ala Ala
                    195                 200                 205

Val Leu Trp Arg Lys Lys Ser Ser Asp
210                 215
```

```
<210> SEQ ID NO 20
<211> LENGTH: 178
<212> TYPE: PRT
<213> ORGANISM: Homo sapiens

<400> SEQUENCE: 20

Met Ile Gly Cys Asp Leu Gly Ser Asp Gly Arg Leu Leu Arg Gly Tyr
1               5                   10                  15

Glu Gln Tyr Ala Tyr Asp Gly Lys Asp Tyr Leu Ala Leu Asn Glu Asp
                    20                  25                  30

Leu Arg Ser Trp Thr Ala Ala Asp Thr Ala Ala Gln Ile Ser Lys Arg
                    35                  40                  45

Lys Cys Glu Ala Ala Asn Val Ala Glu Gln Arg Arg Ala Tyr Leu Glu
                50                  55                  60

Gly Thr Cys Val Glu Trp Leu His Arg Tyr Leu Glu Asn Gly Lys Glu
65                  70                  75                  80

Met Leu Gln Arg Ala Asp Pro Pro Lys Thr His Val Thr His His Pro
                    85                  90                  95

Val Phe Asp Tyr Glu Ala Thr Leu Arg Cys Trp Ala Leu Gly Phe Tyr
                    100                 105                 110

Pro Ala Glu Ile Ile Leu Thr Trp Gln Arg Asp Gly Glu Asp Gln Thr
                    115                 120                 125

Gln Asp Val Glu Leu Val Glu Thr Arg Pro Ala Gly Asp Gly Thr Phe
                    130                 135                 140

Gln Lys Trp Ala Ala Val Val Val Pro Ser Gly Glu Glu Gln Arg Tyr
145                 150                 155                 160

Thr Cys His Val Gln His Glu Gly Leu Pro Glu Pro Leu Met Leu Arg
                    165                 170                 175

Trp Met
```

```
<210> SEQ ID NO 21
<211> LENGTH: 299
<212> TYPE: PRT
<213> ORGANISM: Homo sapiens

<400> SEQUENCE: 21
```

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65              70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Met
    290                 295

<210> SEQ ID NO 22
<211> LENGTH: 248
<212> TYPE: PRT
<213> ORGANISM: Homo sapiens

<400> SEQUENCE: 22

Met Val Val Met Ala Pro Arg Thr Leu Phe Leu Leu Leu Ser Gly Ala
1               5                   10                  15

Leu Thr Leu Thr Glu Thr Trp Ala Gly Ser His Thr Leu Gln Trp Met
            20                  25                  30

Ile Gly Cys Asp Leu Gly Ser Asp Gly Arg Leu Leu Arg Gly Tyr Glu
        35                  40                  45

Gln Tyr Ala Tyr Asp Gly Lys Asp Tyr Leu Ala Leu Asn Glu Asp Leu
    50                  55                  60

Arg Ser Trp Thr Ala Ala Asp Thr Ala Ala Gln Ile Ser Lys Arg Lys

```
                 65                  70                  75                  80
Cys Glu Ala Ala Asn Val Ala Glu Gln Arg Arg Ala Tyr Leu Glu Gly
                 85                  90                  95

Thr Cys Val Glu Trp Leu His Arg Tyr Leu Glu Asn Gly Lys Glu Met
            100                 105                 110

Leu Gln Arg Ala Asp Pro Pro Lys Thr His Val Thr His His Pro Val
        115                 120                 125

Phe Asp Tyr Glu Ala Thr Leu Arg Cys Trp Ala Leu Gly Phe Tyr Pro
    130                 135                 140

Ala Glu Ile Ile Leu Thr Trp Gln Arg Asp Gly Glu Asp Gln Thr Gln
145                 150                 155                 160

Asp Val Glu Leu Val Glu Thr Arg Pro Ala Gly Asp Gly Thr Phe Gln
                165                 170                 175

Lys Trp Ala Ala Val Val Val Pro Ser Gly Glu Glu Gln Arg Tyr Thr
            180                 185                 190

Cys His Val Gln His Glu Gly Leu Pro Glu Pro Leu Met Leu Arg Trp
        195                 200                 205

Lys Gln Ser Ser Leu Pro Thr Ile Pro Ile Met Gly Ile Val Ala Gly
    210                 215                 220

Leu Val Val Leu Ala Ala Val Val Thr Gly Ala Ala Val Ala Ala Val
225                 230                 235                 240

Leu Trp Arg Lys Lys Ser Ser Asp
                245

<210> SEQ ID NO 23
<211> LENGTH: 209
<212> TYPE: PRT
<213> ORGANISM: Homo sapiens

<400> SEQUENCE: 23

Met Val Val Met Ala Pro Arg Thr Leu Phe Leu Leu Leu Ser Gly Ala
1               5                   10                  15

Leu Thr Leu Thr Glu Thr Trp Ala Gly Ser His Thr Leu Gln Trp Met
                20                  25                  30

Ile Gly Cys Asp Leu Gly Ser Asp Gly Arg Leu Leu Arg Gly Tyr Glu
            35                  40                  45

Gln Tyr Ala Tyr Asp Gly Lys Asp Tyr Leu Ala Leu Asn Glu Asp Leu
        50                  55                  60

Arg Ser Trp Thr Ala Ala Asp Thr Ala Ala Gln Ile Ser Lys Arg Lys
65                  70                  75                  80

Cys Glu Ala Ala Asn Val Ala Glu Gln Arg Arg Ala Tyr Leu Glu Gly
                85                  90                  95

Thr Cys Val Glu Trp Leu His Arg Tyr Leu Glu Asn Gly Lys Glu Met
            100                 105                 110

Leu Gln Arg Ala Asp Pro Pro Lys Thr His Val Thr His His Pro Val
        115                 120                 125

Phe Asp Tyr Glu Ala Thr Leu Arg Cys Trp Ala Leu Gly Phe Tyr Pro
    130                 135                 140

Ala Glu Ile Ile Leu Thr Trp Gln Arg Asp Gly Glu Asp Gln Thr Gln
145                 150                 155                 160

Asp Val Glu Leu Val Glu Thr Arg Pro Ala Gly Asp Gly Thr Phe Gln
                165                 170                 175

Lys Trp Ala Ala Val Val Val Pro Ser Gly Glu Glu Gln Arg Tyr Thr
            180                 185                 190
```

Cys His Val Gln His Glu Gly Leu Pro Glu Pro Leu Met Leu Arg Trp
            195                 200                 205

Met

<210> SEQ ID NO 24
<211> LENGTH: 156
<212> TYPE: PRT
<213> ORGANISM: Homo sapiens

<400> SEQUENCE: 24

Met Val Val Met Ala Pro Arg Thr Leu Phe Leu Leu Leu Ser Gly Ala
1               5                   10                  15

Leu Thr Leu Thr Glu Thr Trp Ala Gly Ser His Thr Leu Gln Trp Met
            20                  25                  30

Ile Gly Cys Asp Leu Gly Ser Asp Gly Arg Leu Leu Arg Gly Tyr Glu
        35                  40                  45

Gln Tyr Ala Tyr Asp Gly Lys Asp Tyr Leu Ala Leu Asn Glu Asp Leu
    50                  55                  60

Arg Ser Trp Thr Ala Ala Asp Thr Ala Ala Gln Ile Ser Lys Arg Lys
65                  70                  75                  80

Cys Glu Ala Ala Asn Val Ala Glu Gln Arg Arg Ala Tyr Leu Glu Gly
                85                  90                  95

Thr Cys Val Glu Trp Leu His Arg Tyr Leu Glu Asn Gly Lys Glu Met
            100                 105                 110

Leu Gln Arg Ala Glu Gln Ser Ser Leu Pro Thr Ile Pro Ile Met Gly
        115                 120                 125

Ile Val Ala Gly Leu Val Leu Ala Ala Val Val Thr Gly Ala Ala
    130                 135                 140

Val Ala Ala Val Leu Trp Arg Lys Lys Ser Ser Asp
145                 150                 155

<210> SEQ ID NO 25
<211> LENGTH: 117
<212> TYPE: PRT
<213> ORGANISM: Homo sapiens

<400> SEQUENCE: 25

Met Val Val Met Ala Pro Arg Thr Leu Phe Leu Leu Leu Ser Gly Ala
1               5                   10                  15

Leu Thr Leu Thr Glu Thr Trp Ala Gly Ser His Thr Leu Gln Trp Met
            20                  25                  30

Ile Gly Cys Asp Leu Gly Ser Asp Gly Arg Leu Leu Arg Gly Tyr Glu
        35                  40                  45

Gln Tyr Ala Tyr Asp Gly Lys Asp Tyr Leu Ala Leu Asn Glu Asp Leu
    50                  55                  60

Arg Ser Trp Thr Ala Ala Asp Thr Ala Ala Gln Ile Ser Lys Arg Lys
65                  70                  75                  80

Cys Glu Ala Ala Asn Val Ala Glu Gln Arg Arg Ala Tyr Leu Glu Gly
                85                  90                  95

Thr Cys Val Glu Trp Leu His Arg Tyr Leu Glu Asn Gly Lys Glu Met
            100                 105                 110

Leu Gln Arg Ala Val
        115

<210> SEQ ID NO 26
<211> LENGTH: 156
<212> TYPE: PRT

<213> ORGANISM: Homo sapiens

<400> SEQUENCE: 26

Met Val Val Met Ala Pro Arg Thr Leu Phe Leu Leu Leu Ser Gly Ala
1               5                   10                  15

Leu Thr Leu Thr Glu Thr Trp Ala Asp Pro Pro Lys Thr His Val Thr
            20                  25                  30

His His Pro Val Phe Asp Tyr Glu Ala Thr Leu Arg Cys Trp Ala Leu
        35                  40                  45

Gly Phe Tyr Pro Ala Glu Ile Ile Leu Thr Trp Gln Arg Asp Gly Glu
    50                  55                  60

Asp Gln Thr Gln Asp Val Glu Leu Val Glu Thr Arg Pro Ala Gly Asp
65                  70                  75                  80

Gly Thr Phe Gln Lys Trp Ala Ala Val Val Pro Ser Gly Glu Glu
                85                  90                  95

Gln Arg Tyr Thr Cys His Val Gln His Glu Gly Leu Pro Glu Pro Leu
            100                 105                 110

Met Leu Arg Trp Lys Gln Ser Ser Leu Pro Thr Ile Pro Ile Met Gly
        115                 120                 125

Ile Val Ala Gly Leu Val Val Leu Ala Ala Val Val Thr Gly Ala Ala
    130                 135                 140

Val Ala Ala Val Leu Trp Arg Lys Lys Ser Ser Asp
145                 150                 155

<210> SEQ ID NO 27
<211> LENGTH: 117
<212> TYPE: PRT
<213> ORGANISM: Homo sapiens

<400> SEQUENCE: 27

Met Val Val Met Ala Pro Arg Thr Leu Phe Leu Leu Leu Ser Gly Ala
1               5                   10                  15

Leu Thr Leu Thr Glu Thr Trp Ala Asp Pro Pro Lys Thr His Val Thr
            20                  25                  30

His His Pro Val Phe Asp Tyr Glu Ala Thr Leu Arg Cys Trp Ala Leu
        35                  40                  45

Gly Phe Tyr Pro Ala Glu Ile Ile Leu Thr Trp Gln Arg Asp Gly Glu
    50                  55                  60

Asp Gln Thr Gln Asp Val Glu Leu Val Glu Thr Arg Pro Ala Gly Asp
65                  70                  75                  80

Gly Thr Phe Gln Lys Trp Ala Ala Val Val Pro Ser Gly Glu Glu
                85                  90                  95

Gln Arg Tyr Thr Cys His Val Gln His Glu Gly Leu Pro Glu Pro Leu
            100                 105                 110

Met Leu Arg Trp Met
        115

<210> SEQ ID NO 28
<211> LENGTH: 115
<212> TYPE: PRT
<213> ORGANISM: Homo sapiens

<400> SEQUENCE: 28

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

```
Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
 50                  55                  60

Ala Cys Pro Arg Met Glu Pro Arg Ala Pro Trp Val Glu Gln Glu Gly
 65                  70                  75                  80

Pro Glu Tyr Trp Glu Glu Glu Thr Arg Asn Thr Lys Ala His Ala Gln
                 85                  90                  95

Thr Asp Arg Met Asn Leu Gln Thr Leu Arg Gly Tyr Tyr Asn Gln Ser
                100                 105                 110

Glu Ala Met
        115

<210> SEQ ID NO 29
<211> LENGTH: 125
<212> TYPE: PRT
<213> ORGANISM: Homo sapiens

<400> SEQUENCE: 29

Met Ile Gly Cys Asp Leu Gly Ser Asp Gly Arg Leu Leu Arg Gly Tyr
 1               5                  10                  15

Glu Gln Tyr Ala Tyr Asp Gly Lys Asp Tyr Leu Ala Leu Asn Glu Asp
                 20                  25                  30

Leu Arg Ser Trp Thr Ala Ala Asp Thr Ala Ala Gln Ile Ser Lys Arg
            35                  40                  45

Lys Cys Glu Ala Ala Asn Val Ala Glu Gln Arg Arg Ala Tyr Leu Glu
 50                  55                  60

Gly Thr Cys Val Glu Trp Leu His Arg Tyr Leu Glu Asn Gly Lys Glu
 65                  70                  75                  80

Met Leu Gln Arg Ala Glu Gln Ser Ser Leu Pro Thr Ile Pro Ile Met
                 85                  90                  95

Gly Ile Val Ala Gly Leu Val Val Leu Ala Ala Val Val Thr Gly Ala
                100                 105                 110

Ala Val Ala Ala Val Leu Trp Arg Lys Lys Ser Ser Asp
            115                 120                 125

<210> SEQ ID NO 30
<211> LENGTH: 86
<212> TYPE: PRT
<213> ORGANISM: Homo sapiens

<400> SEQUENCE: 30

Met Ile Gly Cys Asp Leu Gly Ser Asp Gly Arg Leu Leu Arg Gly Tyr
 1               5                  10                  15

Glu Gln Tyr Ala Tyr Asp Gly Lys Asp Tyr Leu Ala Leu Asn Glu Asp
                 20                  25                  30

Leu Arg Ser Trp Thr Ala Ala Asp Thr Ala Ala Gln Ile Ser Lys Arg
            35                  40                  45

Lys Cys Glu Ala Ala Asn Val Ala Glu Gln Arg Arg Ala Tyr Leu Glu
 50                  55                  60

Gly Thr Cys Val Glu Trp Leu His Arg Tyr Leu Glu Asn Gly Lys Glu
 65                  70                  75                  80

Met Leu Gln Arg Ala Val
                 85

<210> SEQ ID NO 31
```

```
<211> LENGTH: 44
<212> TYPE: PRT
<213> ORGANISM: Homo sapiens

<400> SEQUENCE: 31

Met Leu Arg Trp Lys Gln Ser Ser Leu Pro Thr Ile Pro Ile Met Gly
1               5                   10                  15

Ile Val Ala Gly Leu Val Val Leu Ala Ala Val Val Thr Gly Ala Ala
            20                  25                  30

Val Ala Ala Val Leu Trp Arg Lys Lys Ser Ser Asp
        35                  40

<210> SEQ ID NO 32
<211> LENGTH: 40
<212> TYPE: DNA
<213> ORGANISM: Homo sapiens

<400> SEQUENCE: 32
ctgaccgaga cctgggcggg ttctcacacc ctccagtgga                        40

<210> SEQ ID NO 33
<211> LENGTH: 33
<212> TYPE: DNA
<213> ORGANISM: Homo sapiens

<400> SEQUENCE: 33
ccgagacctg ggcggacccc cccaagacac acg                               33

<210> SEQ ID NO 34
<211> LENGTH: 32
<212> TYPE: DNA
<213> ORGANISM: Homo sapiens

<400> SEQUENCE: 34
tcatgctgag atggatgtga aacagctgcc ct                                32

<210> SEQ ID NO 35
<211> LENGTH: 9
<212> TYPE: PRT
<213> ORGANISM: Homo sapiens

<400> SEQUENCE: 35

Trp Ala Gly Ser His Thr Leu Gln Trp
1               5

<210> SEQ ID NO 36
<211> LENGTH: 10
<212> TYPE: PRT
<213> ORGANISM: Homo sapiens

<400> SEQUENCE: 36

Glu Thr Trp Ala Asp Pro Pro Lys Thr His
1               5                   10

<210> SEQ ID NO 37
<211> LENGTH: 5
<212> TYPE: PRT
<213> ORGANISM: Homo sapiens

<400> SEQUENCE: 37

Met Leu Arg Trp Met
1               5
```

```
<210> SEQ ID NO 38
<211> LENGTH: 1490
<212> TYPE: DNA
<213> ORGANISM: Homo sapiens

<400> SEQUENCE: 38
atatagtaac atagtgtggt actttgtctt gaggagatgt cctggactca cacggaaact      60
tagggctacg gaatgaagac gccaaggatg gtggtcatgg cgccccgaac cctcttcctg     120
ctgctctcgg gggccctgac cctgaccgag acctgggcgg gctcccactc catgaggtat     180
ttcagcgccg ccgtgtcccg gcccggccgc ggggagcccc gcttcatcgc catgggctac     240
gtggacgaca cgcagttcgt gcggttcgac agcgactcgg cgtgtccgag gatggagccg     300
cgggcgccgt gggtggagca ggaggggccg gagtattggg aagaggagac acggaacacc     360
aaggcccacg cacagactga cagaatgaac ctgcagaccc tgcgcggcta ctacaaccag     420
agcgaggcca gttctcacac cctccagtgg atgattggct gcgacctggg gtccgacgga     480
cgcctcctcc gcgggtatga acagtatgcc tacgatggca aggattacct cgccctgaac     540
gaggacctgc gctcctggac cgcagcggac actgcggctc agatctccaa gcgcaagtgt     600
gaggcggcca atgtgctga caaaggaga gcctacctgg agggcacgtg cgtggagtgg     660
ctccacagat acctggagaa cgggaaggag atgctgcagc gcgcggaccc ccccaagaca     720
cacgtgaccc accaccctgt cttttgactat gaggccaccc tgaggtgctg ggccctgggc     780
ttctaccctg cggagatcat actgacctgg cagcgggatg gggaggacca gacccaggac     840
gtggagctcg tggagaccag gcctgcaggg gatggaacct tccagaagtg gcagctgtg     900 gtggtgcctt ctggagagga gcagagatac acgtgccatg tgcagcatga ggggctgccg     960
gagcccctca tgctgagatg gaagcagtct tccctgccca ccatcccat catgggtatc    1020 gttgctggcc tggttgtcct tgcagctgta gtcactggag ctgcggtcgc tgctgtgctg    1080
tggagaaaga agagctcaga ttgaaaagga gggagctact tcaggctgc aatgtgaaac    1140 agctgccctg tgtgggactg agtggcaagt cccttttgtga cttcaagaac cctgactcct    1200
ctttgtgcag agaccagccc accctgtgc ccaccatgac cctcttcctc atgctgaact    1260
gcattccttc cccaatcacc tttcctgttc cagaaaaggg gctgggatgt ctccgtctct    1320
gtctcaaatt tgtggtccac tgagctataa cttacttctg tattaaaatt agaatctgag    1380
tataaattta cttttttcaaa ttatttccaa gagagattga tgggttaatt aaaggagaag    1440
attcctgaaa tttgagagac aaaataaatg gaagacatga gaactttcca                1490

<210> SEQ ID NO 39
<211> LENGTH: 1340
<212> TYPE: DNA
<213> ORGANISM: Homo sapiens

<400> SEQUENCE: 39
atatagtaac atagtgtggt actttgtctt gaggagatgt cctggactca cacggaaact      60
tagggctacg gaatgaagac gccaaggatg gtggtcatgg cgccccgaac cctcttcctg     120
ctgctctcgg gggccctgac cctgaccgag acctgggcgg gctcccactc catgaggtat     180
ttcagcgccg ccgtgtcccg gcccggccgc ggggagcccc gcttcatcgc catgggctac     240
gtggacgaca cgcagttcgt gcggttcgac agcgactcgg cgtgtccgag gatggagccg     300
cgggcgccgt gggtggagca ggaggggccg gagtattggg aagaggagac acggaacacc     360
aaggcccacg cacagactga cagaatgaac ctgcagaccc tgcgcggcta ctacaaccag     420
```

| | |
|---|---|
| agcgaggcca gttctcacac cctccagtgg atgattggct gcgacctggg gtccgacgga | 480 |
| cgcctcctcc gcgggtatga acagtatgcc tacgatggca aggattacct cgccctgaac | 540 |
| gaggacctgc gctcctggac cgcagcggac actgcggctc agatctccaa gcgcaagtgt | 600 |
| gaggcggcca atgtggctga acaaaggaga gcctacctgg agggcacgtg cgtggagtgg | 660 |
| ctccacagat acctggagaa cgggaaggag atgctgcagc gcgcggaccc ccccaagaca | 720 |
| cacgtgaccc accaccctgt ctttgactat gaggccaccc tgaggtgctg ggccctgggc | 780 |
| ttctaccctg cggagatcat actgacctgg cagcgggatg gggaggacca gacccaggac | 840 |
| gtggagctcg tggagaccag gcctgcaggg gatggaacct tccagaagtg ggcagctgtg | 900 |
| gtggtgcctt ctggagagga gcagagatac acgtgccatg tgcagcatga ggggctgccg | 960 |
| gagcccctca tgctgagatg gatgtgaaac agctgccctg tgtgggactg agtggcaagt | 1020 |
| cccttttgtga cttcaagaac cctgactcct ctttgtgcag agaccagccc acccctgtgc | 1080 |
| ccaccatgac cctcttcctc atgctgaact gcattccttc cccaatcacc tttcctgttc | 1140 |
| cagaaaaggg gctgggatgt ctccgtctct gtctcaaatt tgtggtccac tgagctataa | 1200 |
| cttacttctg tattaaaatt agaatctgag tataaattta cttttcaaa ttatttccaa | 1260 |
| gagagattga tgggttaatt aaaggagaag attcctgaaa tttgagagac aaaataaatg | 1320 |
| gaagacatga gaactttcca | 1340 |

<210> SEQ ID NO 40
<211> LENGTH: 1220
<212> TYPE: DNA
<213> ORGANISM: Homo sapiens

<400> SEQUENCE: 40

| | |
|---|---|
| atatagtaac atagtgtggt actttgtctt gaggagatgt cctggactca cacggaaact | 60 |
| tagggctacg gaatgaagac gccaaggatg gtggtcatgg cgccccgaac cctcttcctg | 120 |
| ctgctctcgg ggcccctgac cctgaccgag acctgggcgg gttctcacac cctccagtgg | 180 |
| atgattggct gcgacctggg gtccgacgga cgcctcctcc gcgggtatga acagtatgcc | 240 |
| tacgatggca aggattacct cgccctgaac gaggacctgc gctcctggac cgcagcggac | 300 |
| actgcggctc agatctccaa gcgcaagtgt gaggcggcca atgtggctga acaaaggaga | 360 |
| gcctacctgg agggcacgtg cgtggagtgg ctccacagat acctggagaa cgggaaggag | 420 |
| atgctgcagc gcgcggaccc ccccaagaca cacgtgaccc accaccctgt ctttgactat | 480 |
| gaggccaccc tgaggtgctg ggccctgggc ttctaccctg cggagatcat actgacctgg | 540 |
| cagcgggatg gggaggacca gacccaggac gtggagctcg tggagaccag gcctgcaggg | 600 |
| gatggaacct tccagaagtg ggcagctgtg gtggtgcctt ctggagagga gcagagatac | 660 |
| acgtgccatg tgcagcatga ggggctgccg gagcccctca tgctgagatg gaagcagtct | 720 |
| tccctgccca ccatcccat catgggtatc gttgctggcc tggttgtcct tgcagctgta | 780 |
| gtcactggag ctgcggtcgc tgctgtgctg tggagaaaga gagctcaga ttgaaaagga | 840 |
| gggagctact ctcaggctgc aatgtgaaac agctgccctg tgtgggactg agtggcaagt | 900 |
| cccttttgtga cttcaagaac cctgactcct ctttgtgcag agaccagccc acccctgtgc | 960 |
| ccaccatgac cctcttcctc atgctgaact gcattccttc cccaatcacc tttcctgttc | 1020 |
| cagaaaaggg gctgggatgt ctccgtctct gtctcaaatt tgtggtccac tgagctataa | 1080 |
| cttacttctg tattaaaatt agaatctgag tataaattta cttttcaaa ttatttccaa | 1140 |
| gagagattga tgggttaatt aaaggagaag attcctgaaa tttgagagac aaaataaatg | 1200 | gaagacatga gaactttcca                                              1220

<210> SEQ ID NO 41
<211> LENGTH: 1070
<212> TYPE: DNA
<213> ORGANISM: Homo sapiens

<400> SEQUENCE: 41
atatagtaac atagtgtggt actttgtctt gaggagatgt cctggactca cacggaaact    60
tagggctacg gaatgaagac gccaaggatg gtggtcatgg cgccccgaac cctcttcctg   120
ctgctctcgg gggccctgac cctgaccgag acctgggcgg gttctcacac cctccagtgg   180
atgattggct gcgacctggg gtccgacgga cgcctcctcc gcgggtatga acagtatgcc   240
tacgatggca aggattacct cgccctgaac gaggacctgc gctcctggac cgcagcggac   300
actgcggctc agatctccaa gcgcaagtgt gaggcggcca atgtggctga acaaaggaga   360
gcctacctgg agggcacgtg cgtggagtgg ctccacagat acctggagaa cgggaaggag   420
atgctgcagc gcgcggaccc ccccaagaca cacgtgaccc accaccctgt ctttgactat   480
gaggccaccc tgaggtgctg ggccctgggc ttctaccctg cggagatcat actgacctgg   540
cagcgggatg gggaggacca gacccaggac gtggagctcg tggagaccag gcctgcaggg   600
gatgaacct tccagaagtg ggcagctgtg gtggtgcctt ctggagagga gcagagatac   660
acgtgccatg tgcagcatga ggggctgccg agcccctca tgctgagatg gatgtgaaac   720
agctgccctg tgtgggactg agtggcaagt cccttgtga cttcaagaac cctgactcct   780
ctttgtgcag agaccagccc acccctgtgc ccaccatgac cctcttcctc atgctgaact   840
gcattccttc cccaatcacc tttcctgttc cagaaaaggg gctgggatgt ctccgtctct   900
gtctcaaatt tgtggtccac tgagctataa cttacttctg tattaaaatt agaatctgag   960
tataaattta cttttcaaa ttatttccaa gagagattga tgggttaatt aaaggagaag  1020
attcctgaaa tttgagagac aaaataaatg gaagacatga gaactttcca               1070

<210> SEQ ID NO 42
<211> LENGTH: 944
<212> TYPE: DNA
<213> ORGANISM: Homo sapiens

<400> SEQUENCE: 42
atatagtaac atagtgtggt actttgtctt gaggagatgt cctggactca cacggaaact    60
tagggctacg gaatgaagac gccaaggatg gtggtcatgg cgccccgaac cctcttcctg   120
ctgctctcgg gggccctgac cctgaccgag acctgggcgg gttctcacac cctccagtgg   180
atgattggct gcgacctggg gtccgacgga cgcctcctcc gcgggtatga acagtatgcc   240
tacgatggca aggattacct cgccctgaac gaggacctgc gctcctggac cgcagcggac   300
actgcggctc agatctccaa gcgcaagtgt gaggcggcca atgtggctga acaaaggaga   360
gcctacctgg agggcacgtg cgtggagtgg ctccacagat acctggagaa cgggaaggag   420
atgctgcagc gcgcggagca gtcttccctg cccaccatcc ccatcatggg tatcgttgct   480
ggcctggttg tccttgcagc tgtagtcact ggagctgcgc tcgctgctgt gctgtggaga   540
aagaagagct cagattgaaa aggagggagc tactctcagg ctgcaatgtg aaacagctgc   600
cctgtgtggg actgagtggc aagtcccttt gtgacttcaa gaaccctgac tcctcttgt   660
gcagagacca gcccaccccct gtgcccacca tgaccctctt cctcatgctg aactgcattc   720

```
cttccccaat cacctttcct gttccagaaa aggggctggg atgtctccgt ctctgtctca    780
aatttgtggt ccactgagct ataacttact tctgtattaa aattagaatc tgagtataaa    840 tttactttt caaattattt ccaagagaga ttgatgggtt aattaaagga gaagattcct    900
gaaatttgag agacaaaata aatggaagac atgagaactt tcca                    944

<210> SEQ ID NO 43
<211> LENGTH: 794
<212> TYPE: DNA
<213> ORGANISM: Homo sapiens

<400> SEQUENCE: 43
atatagtaac atagtgtggt actttgtctt gaggagatgt cctggactca cacggaaact     60
tagggctacg gaatgaagac gccaaggatg gtggtcatgg cgccccgaac cctcttcctg    120
ctgctctcgg gggccctgac cctgaccgag acctgggcgg ttctcacac cctccagtgg     180 atgattggct gcgacctggg gtccgacgga cgcctcctcc gcgggtatga acagtatgcc    240
tacgatggca aggattacct cgccctgaac gaggacctgc gctcctggac cgcagcggac    300
actgcggctc agatctccaa gcgcaagtgt gaggcggcca atgtggctga caaaggaga     360 gcctacctgg agggcacgtg cgtggagtgg ctccacagat acctgagaa cgggaaggag    420 atgctgcagc gcgcggtgtg aaacagctgc cctgtgtggg actgagtggc aagtcccttt    480
gtgacttcaa gaaccctgac tcctcttgt gcagagacca gccacccct gtgcccacca    540 tgaccctctt cctcatgctg aactgcattc cttccccaat cacctttcct gttccagaaa    600
aggggctggg atgtctccgt ctctgtctca aatttgtggt ccactgagct ataacttact    660
tctgtattaa aattagaatc tgagtataaa tttactttt caaattattt ccaagagaga    720
ttgatgggtt aattaaagga gaagattcct gaaatttgag agacaaaata aatggaagac    780
atgagaactt tcca                                                     794

<210> SEQ ID NO 44
<211> LENGTH: 944
<212> TYPE: DNA
<213> ORGANISM: Homo sapiens

<400> SEQUENCE: 44
atatagtaac atagtgtggt actttgtctt gaggagatgt cctggactca cacggaaact     60
tagggctacg gaatgaagac gccaaggatg gtggtcatgg cgccccgaac cctcttcctg    120
ctgctctcgg gggccctgac cctgaccgag acctgggcgg accccccaa gacacacgtg    180 acccaccacc ctgtctttga ctatgaggcc acctgaggt gctgggccct gggcttctac    240
cctgcggaga tcatactgac ctggcagcgg gatggggagg accagaccca ggacgtggag    300
ctcgtggaga ccaggcctgc aggggatgga accttccaga agtgggcagc tgtggtggtg    360
ccttctggag aggagcagag atacacgtgc catgtgcagc atgagggct gccggagccc    420 ctcatgctga gatggaagca gtcttccctg cccaccatcc ccatcatggg tatcgttgct    480
ggcctggttg tccttgcagc tgtagtcact ggagctgcgg tcgctgctgt gctgtggaga    540
aagaagagct cagattgaaa aggagggagc tactctcagg ctgcaatgtg aaacagctgc    600
cctgtgtggg actgagtggc aagtcccttt gtgacttcaa gaaccctgac tcctcttgt    660 gcagagacca gccacccct gtgcccacca tgaccctctt cctcatgctg aactgcattc    720
cttccccaat cacctttcct gttccagaaa aggggctggg atgtctccgt ctctgtctca    780
aatttgtggt ccactgagct ataacttact tctgtattaa aattagaatc tgagtataaa    840
```

```
tttactttttt caaattattt ccaagagaga ttgatgggtt aattaaagga gaagattcct      900
gaaatttgag agacaaaata aatggaagac atgagaactt ccca                        944
```

<210> SEQ ID NO 45
<211> LENGTH: 794
<212> TYPE: DNA
<213> ORGANISM: Homo sapiens

<400> SEQUENCE: 45

```
atatagtaac atagtgtggt actttgtctt gaggagatgt cctggactca cacggaaact       60
tagggctacg gaatgaagac gccaaggatg gtggtcatgg cgccccgaac cctcttcctg      120
ctgctctcgg gggccctgac cctgaccgag acctgggcgg accccccaa gacacacgtg       180 acccaccacc ctgtctttga ctatgaggcc accctgaggt gctgggccct ggcttctac      240 cctgcggaga tcatactgac ctggcagcgg gatggggagg accagaccca ggacgtggag      300
ctcgtggaga ccaggcctgc aggggatgga accttccaga gtgggcagc tgtggtggtg      360 ccttctggag aggagcagag atacacgtgc catgtgcagc atgagggct gccggagccc      420 ctcatgctga gatggatgtg aaacagctgc cctgtgtggg actgagtggc aagtcccttt     480
gtgacttcaa gaaccctgac tcctctttgt gcagagacca gcccacccct gtgcccacca    540
tgaccctctt cctcatgctg aactgcattc cttccccaat caccttttcct gttccagaaa    600 agggggctggg atgtctccgt ctctgtctca aatttgtggt ccactgagct ataacttact    660
tctgtattaa aattagaatc tgagtataaa tttacttttt caaattattt ccaagagaga    720
ttgatgggtt aattaaagga gaagattcct gaaatttgag agacaaaata aatggaagac    780
atgagaactt tcca                                                        794
```

<210> SEQ ID NO 46
<211> LENGTH: 938
<212> TYPE: DNA
<213> ORGANISM: Homo sapiens

<400> SEQUENCE: 46

```
atatagtaac atagtgtggt actttgtctt gaggagatgt cctggactca cacggaaact       60
tagggctacg gaatgaagac gccaaggatg gtggtcatgg cgccccgaac cctcttcctg      120
ctgctctcgg gggccctgac cctgaccgag acctgggcgg ctcccactc catgaggtat      180 ttcagcgccg ccgtgtcccg gcccggccgc ggggagcccc gcttcatcgc catgggctac      240
gtggacgaca cgcagttcgt gcggttcgac agcgactcgg cgtgtccgag gatggagccg     300
cgggcgccgt gggtggagca ggaggggccg gagtattggg aagaggagac acggaacacc     360
aaggcccacg cacagactga cagaatgaac ctgcagaccc tgcgcggcta ctacaaccag     420
agcgaggcca gcagtcttc cctgcccacc atccccatca tgggtatcgt tgctggcctg    480
gttgtccttg cagctgtagt cactggagct gcggtcgctg ctgtgctgtg agaaagaag     540 agctcagatt gaaaaggagg gagctactct caggctgcaa tgtgaaacag ctgccctgtg     600
tgggactgag tggcaagtcc ctttgtgact tcaagaaccc tgactcctct ttgtgcagag     660
accagcccac ccctgtgccc accatgaccc tcttcctcat gctgaactgc attccttccc     720 caatcaccctt tcctgttcca gaaaagggc tgggatgtct ccgtctctgt ctcaaatttg    780
tggtccactg agctataact tacttctgta ttaaaattag aatctgagta taaatttact    840
ttttcaaatt atttccaaga gagattgatg ggttaattaa aggagaagat tcctgaaatt    900
```
tgagagacaa ataaatgga agacatgaga actttcca                            938

<210> SEQ ID NO 47
<211> LENGTH: 788
<212> TYPE: DNA
<213> ORGANISM: Homo sapiens

<400> SEQUENCE: 47
atatagtaac atagtgtggt actttgtctt gaggagatgt cctggactca cacggaaact    60
tagggctacg gaatgaagac gccaaggatg gtggtcatgg cgccccgaac cctcttcctg   120
ctgctctcgg gggccctgac cctgaccgag acctgggcgg gctcccactc catgaggtat   180
ttcagcgccg ccgtgtcccg gcccggccgc ggggagcccc gcttcatcgc catgggctac   240
gtggacgaca cgcagttcgt gcggttcgac agcgactcgg cgtgtccgag gatggagccg   300
cgggcgccgt gggtggagca ggaggggccg gagtattggg aagaggagac acggaacacc   360
aaggcccacg cacagactga cagaatgaac ctgcagaccc tgcgcggcta ctacaaccag   420
agcgaggcca tgtgaaacag ctgccctgtg tgggactgag tggcaagtcc ctttgtgact   480
tcaagaaccc tgactcctct ttgtgcagag accagcccac ccctgtgccc accatgaccc   540
tcttcctcat gctgaactgc attccttccc caatcacctt tcctgttcca gaaaaggggc   600
tgggatgtct ccgtctctgt ctcaaatttg tggtccactg agctataact tacttctgta   660
ttaaaattag aatctgagta taaatttact ttttcaaatt atttccaaga gagattgatg   720
ggttaattaa aggagaagat tcctgaaatt tgagagacaa aataaatgga agacatgaga   780
actttcca                                                           788

<210> SEQ ID NO 48
<211> LENGTH: 1427
<212> TYPE: DNA
<213> ORGANISM: Homo sapiens

<400> SEQUENCE: 48
actcattctc cccagacgcc aaggatggtg gtcatggcgc ccgaaccct cttcctgctg    60 ctctcggggg ccctgaccct gaccgagacc tgggcgggct cccactccat gaggtatttc   120
agcgccgccg tgtcccggcc cggccgcggg gagccccgct tcatcgccat gggctacgtg   180
gacgacacgc agttcgtgcg gttcgacagc gactcggcgt gtccgaggat ggagccgcgg   240
gcgccgtggg tggagcagga ggggccggag tattgggaag aggagacacg gaacaccaag   300
gcccacgcac agactgacag aatgaacctg cagaccctgc gcggctacta caaccagagc   360
gaggccagtt ctcacaccct ccagtggatg attggctgcg acctggggtc cgacggacgc   420
ctcctccgcg gtatgaaca gtatgcctac gatggcaagg attacctcgc cctgaacgag   480
gacctgcgct cctggaccgc agcggacact gcggctcaga tctccaagcg caagtgtgag   540
gcggccaatg tggctgaaca aaggagagcc tacctggagg gcacgtgcgt ggagtggctc   600
cacagatacc tggagaacgg gaaggagatg ctgcagcgcg cggacccccc caagacacac   660
gtgacccacc accctgtctt tgactatgag gccaccctga ggtgctgggc cctgggcttc   720
taccctgcgg agatcatact gacctggcag cgggatgggg aggaccagac ccaggacgtg   780
gagctcgtgg agaccaggcc tgcaggggat ggaaccttcc agaagtgggc agctgtggtg   840
gtgccttctg gagaggagca gagatacacg tgccatgtgc agcatgaggg gctgccggag   900 ccctcatgc tgagatggaa gcagtcttcc ctgcccacca tccccatcat gggtatcgtt   960
gctggcctgg ttgtccttgc agctgtagtc actggagctg cggtcgctgc tgtgctgtgg  1020

```
agaaagaaga gctcagattg aaaaggaggg agctactctc aggctgcaat gtgaaacagc    1080
tgccctgtgt gggactgagt ggcaagtccc tttgtgactt caagaaccct gactcctctt    1140
tgtgcagaga ccagcccacc cctgtgccca ccatgaccct cttcctcatg ctgaactgca    1200
ttccttcccc aatcaccttt cctgttccag aaaaggggct gggatgtctc cgtctctgtc    1260
tcaaatttgt ggtccactga gctataactt acttctgtat aaaattaga atctgagtat    1320 aaatttactt tttcaaatta tttccaagag agattgatgg gttaattaaa ggagaagatt    1380
cctgaaattt gagagacaaa ataaatggaa gacatgagaa ctttcca                 1427
```

<210> SEQ ID NO 49
<211> LENGTH: 1276
<212> TYPE: DNA
<213> ORGANISM: Homo sapiens

<400> SEQUENCE: 49

```
actcattctc cccagacgcc aaggatggtg gtcatggcgc cccgaaccct cttcctgctg     60
ctctcggggg ccctgaccct gaccgagacc tgggcgggct cccactccat gaggtatttc    120
agcgccgccg tgtcccggcc cggccgcggg gagccccgct tcatcgccat gggctacgtg    180
gacgacacgc agttcgtgcg gttcgacagc gactcggcgt gtccgaggat ggagccgcgg    240
gcgccgtggg tggagcagga ggggccggag tattgggaag aggagacacg gaacaccaag    300
gcccacgcac agactgacag aatgaacctg cagaccctgc gcggctacta caaccagagc    360
gaggccagtt ctcacaccct ccagtggatg attggctgcg acctgggggtc cgacggacgc    420 ctcctccgcg gtatgaaca gtatgcctac gatggcaagg attacctcgc cctgaacgag    480
gacctgcgct cctggaccgc agcggacact gcggctcaga tctccaagcg caagtgtgag    540
gcggccaatg tggctgaaca aaggagagcc tacctggagg gcacgtgcgt ggagtggctc    600
cacagatacc tggagaacgg gaaggagatg ctgcagcgcg cggaccccccc caagacacac    660 gtgacccacc accctgtctt tgactatgag gccaccctga ggtgctgggc cctgggcttc    720
taccctgcgg agatcatact gacctggcag cgggatggga ggaccagacc caggacgtgg    780
agctcgtgga gaccaggcct gcaggggatg gaaccttcca gaagtgggca gctgtggtgg    840
tgccttctgg agaggagcag agatacacgt gccatgtgca gcatgagggg ctgccggagc    900
ccctcatgct gagatggatg tgaaacagct gccctgtgtg ggactgagtg gcaagtccct    960 tgtgacttc aagaaccctg actcctcttt gtgcagagac cagcccaccc ctgtgcccac    1020
catgaccctt tcctcatgc tgaactgcat tccttcccca atcaccttc ctgttccaga    1080 aaaggggctg gatgtctcc gtctctgtct caaatttgtg gtccactgag ctataactta    1140
cttctgtatt aaaattagaa tctgagtata aatttacttt ttcaaattat ttccaagaga    1200
gattgatggg ttaattaaag gagaagattc ctgaaatttg agagacaaaa taaatggaag    1260
acatgagaac tttcca                                                    1276
```

<210> SEQ ID NO 50
<211> LENGTH: 1157
<212> TYPE: DNA
<213> ORGANISM: Homo sapiens

<400> SEQUENCE: 50

```
actcattctc cccagacgcc aaggatggtg gtcatggcgc cccgaaccct cttcctgctg     60
ctctcggggg ccctgaccct gaccgagacc tgggcgggtt ctcacaccct ccagtggatg    120
```

```
attggctgcg acctggggtc cgacggacgc ctcctccgcg ggtatgaaca gtatgcctac      180
gatggcaagg attacctcgc cctgaacgag gacctgcgct cctggaccgc agcggacact      240
gcggctcaga tctccaagcg caagtgtgag gcggccaatg tggctgaaca aaggagagcc      300
tacctggagg gcacgtgcgt ggagtggctc cacagatacc tggagaacgg gaaggagatg      360
ctgcagcgcg cggaccccc caagacacac gtgacccacc accctgtctt tgactatgag      420
gccaccctga ggtgctgggc cctgggcttc taccctgcgg agatcatact gacctggcag      480
cgggatgggg aggaccagac ccaggacgtg gagctcgtgg agaccaggcc tgcaggggat      540
ggaaccttcc agaagtgggc agctgtggtg gtgccttctg gagaggagca gagatacacg      600
tgccatgtgc agcatgaggg gctgccggag cccctcatgc tgagatggaa gcagtcttcc      660
ctgcccacca tccccatcat gggtatcgtt gctggcctgg ttgtccttgc agctgtagtc      720
actggagctg cggtcgctgc tgtgctgtgg agaaagaaga gctcagattg aaaaggaggg      780
agctactctc aggctgcaat gtgaaacagc tgccctgtgt gggactgagt ggcaagtccc      840
tttgtgactt caagaaccct gactcctctt tgtgcagaga ccagcccacc cctgtgccca      900
ccatgaccct cttcctcatg ctgaactgca ttccttcccc aatcaccttt cctgttccag      960
aaaaggggct gggatgtctc cgtctctgtc tcaaatttgt ggtccactga gctataactt     1020
acttctgtat taaaattaga atctgagtat aaatttactt tttcaaatta tttccaagag     1080
agattgatgg gttaattaaa ggagaagatt cctgaaattt gagagacaaa ataaatggaa     1140
gacatgagaa ctttcca                                                    1157

<210> SEQ ID NO 51
<211> LENGTH: 1040
<212> TYPE: DNA
<213> ORGANISM: Homo sapiens

<400> SEQUENCE: 51
actcattctc cccagacgcc aaggatggtg gtcatggcgc cccgaaccct cttcctgctg       60
ctctcggggg ccctgaccct gaccgagacc tgggcgggtt ctcacaccct ccagtggatg      120
attggctgcg acctggggtc cgacggacgc ctcctccgcg ggtatgaaca gtatgcctac      180
gatggcaagg attacctcgc cctgaacgag gacctgcgct cctggaccgc agcggacact      240
gcggctcaga tctccaagcg caagtgtgag gcggccaatg tggctgaaca aaggagagcc      300
tacctggagg gcacgtgcgt ggagtggctc cacagatacc tggagaacgg gaaggagatg      360
ctgcagcgcg cggaccccc caagacacac gtgacccacc accctgtctt tgactatgag      420
gccaccctga ggtgctgggc cctgggcttc taccctgcgg agatcatact gacctggcag      480
cgggatgggg aggaccagac ccaggacgtg gagctcgtgg agaccaggcc tgcaggggat      540
ggaaccttcc agaagtgggc agctgtggtg gtgccttctg gagaggagca gagatacacg      600
tgccatgtgc agcatgaggg gctgccggag cccctcatgc tgagatggaa ttgaaaagga      660
gggagctact ctcaggctgc aatgtgaaac agctgccctg tgtgggactg agtggcaagt      720 cccctttgtga cttcaagaac cctgactcct ctttgtgcag agaccagccc accctgtgc      780 ccaccatgac cctcttcctc atgctgaact gcattccttc cccaatcacc tttcctgttc      840
cagaaaaggg gctgggatgt ctccgtctct gtctcaaatt tgtggtccac tgagctataa      900
cttacttctg tattaaaatt agaatctgag tataaattta cttttcaaa ttatttccaa      960 gagagattga tgggttaatt aaaggagaag attcctgaaa tttgagagac aaaataaatg     1020
gaagacatga actttcca                                                   1040
```

```
<210> SEQ ID NO 52
<211> LENGTH: 881
<212> TYPE: DNA
<213> ORGANISM: Homo sapiens

<400> SEQUENCE: 52
actcattctc cccagacgcc aaggatggtg gtcatggcgc cccgaaccct cttcctgctg     60
ctctcggggg ccctgaccct gaccgagacc tgggcgggtt ctcacaccct ccagtggatg    120
attggctgcg acctggggtc cgacggacgc ctcctccgcg ggtatgaaca gtatgcctac    180
gatggcaagg attacctcgc cctgaacgag gacctgcgct cctggaccgc agcggacact    240
gcggctcaga tctccaagcg caagtgtgag gcggccaatg tggctgaaca aaggagagcc    300
tacctggagg gcacgtgcgt ggagtggctc cacagatacc tggagaacgg gaaggagatg    360
ctgcagcgcg cggagcagtc ttccctgccc accatcccca tcatgggtat cgttgctggc    420
ctggttgtcc ttgcagctgt agtcactgga gctgcggtcg ctgctgtgct gtggagaaag    480
aagagctcag attgaaaagg agggagctac tctcaggctg caatgtgaaa cagctgccct    540
gtgtgggact gagtggcaag tccctttgtg acttcaagaa ccctgactcc tctttgtgca    600
gagaccagcc caccctgtg cccaccatga ccctcttcct catgctgaac tgcattcctt    660
ccccaatcac ctttcctgtt ccagaaaagg ggctgggatg tctccgtctc tgtctcaaat    720
ttgtggtcca ctgagctata acttacttct gtattaaaat tagaatctga gtataaattt    780 acttttcaa attatttcca agagagattg atgggttaat taaggagaa gattcctgaa    840 atttgagaga caaataaat ggaagacatg agaactttcc a                        881

<210> SEQ ID NO 53
<211> LENGTH: 731
<212> TYPE: DNA
<213> ORGANISM: Homo sapiens

<400> SEQUENCE: 53
actcattctc cccagacgcc aaggatggtg gtcatggcgc cccgaaccct cttcctgctg     60
ctctcggggg ccctgaccct gaccgagacc tgggcgggtt ctcacaccct ccagtggatg    120
attggctgcg acctggggtc cgacggacgc ctcctccgcg ggtatgaaca gtatgcctac    180
gatggcaagg attacctcgc cctgaacgag gacctgcgct cctggaccgc agcggacact    240
gcggctcaga tctccaagcg caagtgtgag gcggccaatg tggctgaaca aaggagagcc    300
tacctggagg gcacgtgcgt ggagtggctc cacagatacc tggagaacgg gaaggagatg    360
ctgcagcgcg cggtgtgaaa cagctgccct gtgtgggact gagtggcaag tccctttgtg    420
acttcaagaa ccctgactcc tctttgtgca gagaccagcc caccctgtg cccaccatga    480 ccctcttcct catgctgaac tgcattcctt ccccaatcac ctttcctgtt ccagaaaagg    540
ggctgggatg tctccgtctc tgtctcaaat ttgtggtcca ctgagctata acttacttct    600
gtattaaaat tagaatctga gtataaattt acttttcaa attatttcca agagagattg    660
atgggttaat taaggagaa gattcctgaa atttgagaga caaataaat ggaagacatg    720 agaactttcc a                                                         731

<210> SEQ ID NO 54
<211> LENGTH: 881
<212> TYPE: DNA
<213> ORGANISM: Homo sapiens
```

<400> SEQUENCE: 54

```
actcattctc cccagacgcc aaggatggtg gtcatggcgc cccgaaccct cttcctgctg      60
ctctcggggg ccctgaccct gaccgagacc tgggcggacc cccccaagac acacgtgacc     120
caccaccctg tctttgacta tgaggccacc ctgaggtgct gggccctggg cttctaccct     180
gcggagatca tactgacctg gcagcgggat ggggaggacc agacccagga cgtggagctc     240
gtggagacca ggcctgcagg ggatggaacc ttccagaagt gggcagctgt ggtggtgcct     300
tctggagagg agcagagata cacgtgccat gtgcagcatg aggggctgcc ggagcccctc     360
atgctgagat ggaagcagtc ttccctgccc accatcccca tcatgggtat cgttgctggc     420
ctggttgtcc ttgcagctgt agtcactgga gctgcggtcg ctgctgtgct gtggagaaag     480
aagagctcag attgaaaagg agggagctac tctcaggctg caatgtgaaa cagctgccct     540
gtgtgggact gagtggcaag tccctttgtg acttcaagaa ccctgactcc tctttgtgca     600
gagaccagcc caccctgtg cccaccatga ccctcttcct catgctgaac tgcattcctt     660
ccccaatcac ctttcctgtt ccagaaaagg ggctgggatg tctccgtctc tgtctcaaat     720
tgtggtcca ctgagctata acttacttct gtattaaaat tagaatctga gtataaattt     780
actttttcaa attatttcca agagagattg atgggttaat taaggagaa gattcctgaa     840
atttgagaga caaataaat ggaagacatg agaactttcc a                         881
```

<210> SEQ ID NO 55
<211> LENGTH: 731
<212> TYPE: DNA
<213> ORGANISM: Homo sapiens

<400> SEQUENCE: 55

```
actcattctc cccagacgcc aaggatggtg gtcatggcgc cccgaaccct cttcctgctg      60
ctctcggggg ccctgaccct gaccgagacc tgggcggacc cccccaagac acacgtgacc     120
caccaccctg tctttgacta tgaggccacc ctgaggtgct gggccctggg cttctaccct     180
gcggagatca tactgacctg gcagcgggat ggggaggacc agacccagga cgtggagctc     240
gtggagacca ggcctgcagg ggatggaacc ttccagaagt gggcagctgt ggtggtgcct     300
tctggagagg agcagagata cacgtgccat gtgcagcatg aggggctgcc ggagcccctc     360
atgctgagat ggatgtgaaa cagctgccct gtgtgggact gagtggcaag tccctttgtg     420
acttcaagaa ccctgactcc tctttgtgca gagaccagcc caccctgtg cccaccatga     480
ccctcttcct catgctgaac tgcattcctt ccccaatcac ctttcctgtt ccagaaaagg     540
ggctgggatg tctccgtctc tgtctcaaat tgtggtcca ctgagctata acttacttct     600
gtattaaaat tagaatctga gtataaattt actttttcaa attatttcca agagagattg     660
atgggttaat taaggagaa gattcctgaa atttgagaga caaataaat ggaagacatg     720
agaactttcc a                                                         731
```

<210> SEQ ID NO 56
<211> LENGTH: 875
<212> TYPE: DNA
<213> ORGANISM: Homo sapiens

<400> SEQUENCE: 56

```
actcattctc cccagacgcc aaggatggtg gtcatggcgc cccgaaccct cttcctgctg      60
ctctcggggg ccctgaccct gaccgagacc tgggcgggct cccactccat gaggtatttc     120
agcgccgccg tgtcccggcc cggccgcggg gagccccgct tcatcgccat gggctacgtg     180
```

```
gacgacacgc agttcgtgcg gttcgacagc gactcggcgt gtccgaggat ggagccgcgg    240
gcgccgtggg tggagcagga ggggccggag tattgggaag aggagacacg gaacaccaag    300
gcccacgcac agactgacag aatgaacctg cagaccctgc gcggctacta caaccagagc    360
gaggccaagc agtcttccct gcccaccatc cccatcatgg gtatcgttgc tggcctggtt    420
gtccttgcag ctgtagtcac tggagctgcg gtcgctgctg tgctgtggag aaagaagagc    480
tcagattgaa aaggagggag ctactctcag gctgcaatgt gaaacagctg ccctgtgtgg    540
gactgagtgg caagtccctt tgtgacttca agaaccctga ctcctctttg tgcagagacc    600
agcccacccc tgtgcccacc atgaccctct tcctcatgct gaactgcatt ccttccccaa    660
tcacctttcc tgttccagaa aaggggctgg gatgtctccg tctctgtctc aaatttgtgg    720
tccactgagc tataacttac ttctgtatta aaattagaat ctgagtataa atttactttt    780
tcaaattatt ccaagagag attgatgggt taattaaagg agaagattcc tgaaatttga    840
gagacaaaat aaatggaaga catgagaact ttcca    875

<210> SEQ ID NO 57
<211> LENGTH: 725
<212> TYPE: DNA
<213> ORGANISM: Homo sapiens

<400> SEQUENCE: 57
actcattctc cccagacgcc aaggatggtg gtcatggcgc cccgaacccct cttcctgctg     60 ctctcggggg ccctgaccct gaccgagacc tgggcgggct cccactccat gaggtatttc    120
agcgccgccg tgtcccggcc cggccgcggg gagccccgct tcatcgccat gggctacgtg    180
gacgacacgc agttcgtgcg gttcgacagc gactcggcgt gtccgaggat ggagccgcgg    240
gcgccgtggg tggagcagga ggggccggag tattgggaag aggagacacg gaacaccaag    300
gcccacgcac agactgacag aatgaacctg cagaccctgc gcggctacta caaccagagc    360
gaggccatgt gaaacagctg ccctgtgtgg gactgagtgg caagtccctt tgtgacttca    420
agaaccctga ctcctctttg tgcagagacc agcccacccc tgtgcccacc atgaccctct    480
tcctcatgct gaactgcatt ccttccccaa tcacctttcc tgttccagaa aaggggctgg    540
gatgtctccg tctctgtctc aaatttgtgg tccactgagc tataacttac ttctgtatta    600
aaattagaat ctgagtataa atttactttt tcaaattatt ccaagagag attgatgggt    660 taattaaagg agaagattcc tgaaatttga gagacaaaat aaatggaaga catgagaact    720
ttcca                                                                725

<210> SEQ ID NO 58
<211> LENGTH: 1578
<212> TYPE: DNA
<213> ORGANISM: Homo sapiens

<400> SEQUENCE: 58
agtgtggtac tttgtcttga ggagatgtcc tggactcaca cggaaactta gggctacgga     60
atgaagttct cactcccatt aggtgacagg ttttagaga agccaatcag cgtcgccgcg    120
gtcctggttc taaagtcctc gctcacccac ccggactcat tctccccaga cgccaaggat    180
ggtggtcatg gcgccccgaa ccctcttcct gctgctctcg ggggccctga ccctgaccga    240
gacctgggcg gctccccact ccatgaggta tttcagcgcc gccgtgtccc ggcccggccg    300
cggggagccc cgcttcatcg ccatgggcta cgtggacgac acgcagttcg tgcggttcga    360
```

```
cagcgactcg gcgtgtccga ggatggagcc gcgggcgccg tgggtggagc aggaggggcc    420
ggagtattgg gaagaggaga cacggaacac caaggcccac gcacagactg acagaatgaa    480
cctgcagacc ctgcgcggct actacaacca gagcgaggcc agttctcaca ccctccagtg    540
gatgattggc tgcgacctgg ggtccgacgg acgcctcctc cgcgggtatg aacagtatgc    600
ctacgatggc aaggattacc tcgccctgaa cgaggacctg cgctcctgga ccgcagcgga    660
cactgcggct cagatctcca agcgcaagtg tgaggcggcc aatgtggctg aacaaaggag    720
agcctacctg gagggcacgt gcgtggagtg gctccacaga tacctggaga cgggaaggga    780
gatgctgcag cgcgcggacc ccccaagac acacgtgacc caccaccctg tctttgacta    840
tgaggccacc ctgaggtgct gggccctggg cttctaccct gcggagatca tactgacctg    900
gcagcgggat ggggaggacc agacccagga cgtggagctc gtggagacca ggcctgcagg    960
ggatggaacc ttccagaagt gggcagctgt ggtggtgcct tctggagagg agcagagata   1020
cacgtgccat gtgcagcatg aggggctgcc ggagcccctc atgctgagat ggaagcagtc   1080
ttccctgccc accatcccca tcatgggtat cgttgctggc ctggttgtcc ttgcagctgt   1140
agtcactgga gctgcggtcg ctgctgtgct gtggagaaag aagagctcag attgaaaagg   1200
agggagctac tctcaggctg caatgtgaaa cagctgccct gtgtgggact gagtggcaag   1260 tcccttttgtg acttcaagaa ccctgactcc tctttgtgca gagaccagcc caccctgtg    1320 cccaccatga ccctcttcct catgctgaac tgcattcctt ccccaatcac ctttcctgtt   1380
ccagaaaagg ggctgggatg tctccgtctc tgtctcaaat ttgtggtcca ctgagctata   1440
acttacttct gtattaaaat tagaatctga gtataaattt actttttcaa attatttcca   1500
agagagattg atgggttaat taaaggagaa gattcctgaa atttgagaga caaaataaat   1560
ggaagacatg agaacttt                                                  1578

<210> SEQ ID NO 59
<211> LENGTH: 1428
<212> TYPE: DNA
<213> ORGANISM: Homo sapiens

<400> SEQUENCE: 59
agtgtggtac tttgtcttga ggagatgtcc tggactcaca cggaaactta gggctacgga     60
atgaagttct cactcccatt aggtgacagg ttttttagaga agccaatcag cgtcgccgcg    120
gtcctggttc taaagtcctc gctcacccac ccggactcat tctccccaga cgccaaggat    180
ggtggtcatg gcgccccgaa ccctcttcct gctgctctcg ggggccctga ccctgaccga    240
gacctgggcg ggctcccact ccatgaggta tttcagcgcc gccgtgtccc ggcccggccg    300
cggggagccc cgcttcatcg ccatgggcta cgtggacgac acgcagttcg tgcggttcga    360
cagcgactcg gcgtgtccga ggatggagcc gcgggcgccg tgggtggagc aggaggggcc    420
ggagtattgg gaagaggaga cacggaacac caaggcccac gcacagactg acagaatgaa    480
cctgcagacc ctgcgcggct actacaacca gagcgaggcc agttctcaca ccctccagtg    540
gatgattggc tgcgacctgg ggtccgacgg acgcctcctc cgcgggtatg aacagtatgc    600
ctacgatggc aaggattacc tcgccctgaa cgaggacctg cgctcctgga ccgcagcgga    660
cactgcggct cagatctcca agcgcaagtg tgaggcggcc aatgtggctg aacaaaggag    720
agcctacctg gagggcacgt gcgtggagtg gctccacaga tacctggaga cgggaaggga    780
gatgctgcag cgcgcggacc ccccaagac acacgtgacc caccaccctg tctttgacta    840
tgaggccacc ctgaggtgct gggccctggg cttctaccct gcggagatca tactgacctg    900
```

```
gcagcgggat ggggaggacc agacccagga cgtggagctc gtggagacca ggcctgcagg        960
ggatggaacc ttccagaagt gggcagctgt ggtggtgcct tctggagagg agcagagata       1020
cacgtgccat gtgcagcatg aggggctgcc ggagcccctc atgctgagat ggatgtgaaa       1080
cagctgccct gtgtgggact gagtggcaag tcccttttgtg acttcaagaa ccctgactcc      1140
tctttgtgca gagaccagcc cacccctgtg cccaccatga ccctcttcct catgctgaac       1200
tgcattcctt ccccaatcac ctttcctgtt ccagaaaagg ggctgggatg tctccgtctc       1260
tgtctcaaat ttgtggtcca ctgagctata acttacttct gtattaaaat tagaatctga       1320
gtataaattt acttttttcaa attatttcca agagagattg atgggttaat taaaggagaa      1380
gattcctgaa atttgagaga caaaataaat ggaagacatg agaacttt                    1428
```

<210> SEQ ID NO 60
<211> LENGTH: 1308
<212> TYPE: DNA
<213> ORGANISM: Homo sapiens

<400> SEQUENCE: 60

```
agtgtggtac tttgtcttga ggagatgtcc tggactcaca cggaaactta gggctacgga        60
atgaagttct cactcccatt aggtgacagg tttttagaga agccaatcag cgtcgccgcg       120
gtcctggttc taaagtcctc gctcacccac ccggactcat tctccccaga cgccaaggat       180
ggtggtcatg gcgccccgaa ccctcttcct gctgctctcg ggggccctga ccctgaccga       240
gacctgggcg ggttctcaca ccctccagtg gatgattggc tgcgacctgg ggtccgacgg       300
acgcctcctc cgcgggtatg aacagtatgc ctacgatggc aaggattacc tcgccctgaa       360
cgaggacctg cgctcctgga ccgcagcgga cactgcggct cagatctcca agcgcaagtg       420
tgaggcggcc aatgtggctg aacaaaggag agcctacctg gagggcacgt gcgtggagtg       480
gctccacaga tacctggaga cgggaagga tgatgctgcag cgcgcggacc ccccaagac        540 acacgtgacc caccacctg tctttgacta tgaggccacc ctgaggtgct gggccctggg       600 cttctacccct gcgagatca tactgacctg gcagcgggat ggggaggacc agacccagga       660
cgtggagctc gtggagacca ggcctgcagg ggatggaacc ttccagaagt gggcagctgt       720
ggtggtgcct tctggagagg agcagagata cacgtgccat gtgcagcatg aggggctgcc       780
ggagcccctc atgctgagat ggaagcagtc ttccctgccc accatcccca tcatgggtat       840
cgttgctggc ctggttgtcc ttgcagctgt agtcactgga gctgcggtcg ctgctgtgct       900
gtggagaaag aagagctcag attgaaaagg agggagctac tctcaggctg caatgtgaaa       960
cagctgccct gtgtgggact gagtggcaag tcccttttgtg acttcaagaa ccctgactcc      1020
tctttgtgca gagaccagcc cacccctgtg cccaccatga ccctcttcct catgctgaac       1080
tgcattcctt ccccaatcac ctttcctgtt ccagaaaagg ggctgggatg tctccgtctc       1140
tgtctcaaat ttgtggtcca ctgagctata acttacttct gtattaaaat tagaatctga       1200
gtataaattt acttttttcaa attatttcca agagagattg atgggttaat taaaggagaa      1260
gattcctgaa atttgagaga caaaataaat ggaagacatg agaacttt                    1308
```

<210> SEQ ID NO 61
<211> LENGTH: 1158
<212> TYPE: DNA
<213> ORGANISM: Homo sapiens

<400> SEQUENCE: 61

| | |
|---|---|
| agtgtggtac tttgtcttga ggagatgtcc tggactcaca cggaaactta gggctacgga | 60 |
| atgaagttct cactcccatt aggtgacagg ttttagaga agccaatcag cgtcgccgcg | 120 |
| gtcctggttc taaagtcctc gctcacccac ccggactcat tctccccaga cgccaaggat | 180 |
| ggtggtcatg gcgccccgaa ccctcttcct gctgctctcg ggggccctga ccctgaccga | 240 |
| gacctgggcg ggttctcaca ccctccagtg gatgattggc tgcgacctgg ggtccgacgg | 300 |
| acgcctcctc cgcgggtatg aacagtatgc ctacgatggc aaggattacc tcgccctgaa | 360 |
| cgaggacctg cgctcctgga ccgcagcgga cactgcggct cagatctcca agcgcaagtg | 420 |
| tgaggcggcc aatgtggctg aacaaaggag agcctacctg gagggcacgt gcgtggagtg | 480 |
| gctccacaga tacctggaga acgggaagga gatgctgcag cgcgcggacc ccccaagac | 540 |
| acacgtgacc caccccctg tctttgacta tgaggccacc ctgaggtgct gggcctggg | 600 |
| cttctaccct gcggagatca tactgacctg gcagcgggat ggggaggacc agacccagga | 660 |
| cgtggagctc gtggagacca ggcctgcagg ggatggaacc ttccagaagt gggcagctgt | 720 |
| ggtggtgcct tctggagagg agcagagata cacgtgccat gtgcagcatg aggggctgcc | 780 |
| ggagcccctc atgctgagat ggatgtgaaa cagctgccct gtgtgggact gagtggcaag | 840 |
| tcccttgtg acttcaagaa ccctgactcc tctttgtgca gagaccagcc caccctgtg | 900 |
| cccaccatga ccctcttcct catgctgaac tgcattcctt ccccaatcac ctttcctgtt | 960 |
| ccagaaaagg ggctgggatg tctccgtctc tgtctcaaat ttgtggtcca ctgagctata | 1020 |
| acttacttct gtattaaaat tagaatctga gtataaattt acttttcaa attatttcca | 1080 |
| agagagattg atgggttaat taaggagaa gattcctgaa atttgagaga caaataaat | 1140 |
| ggaagacatg agaacttt | 1158 |

<210> SEQ ID NO 62
<211> LENGTH: 1032
<212> TYPE: DNA
<213> ORGANISM: Homo sapiens

<400> SEQUENCE: 62

| | |
|---|---|
| agtgtggtac tttgtcttga ggagatgtcc tggactcaca cggaaactta gggctacgga | 60 |
| atgaagttct cactcccatt aggtgacagg ttttagaga agccaatcag cgtcgccgcg | 120 |
| gtcctggttc taaagtcctc gctcacccac ccggactcat tctccccaga cgccaaggat | 180 |
| ggtggtcatg gcgccccgaa ccctcttcct gctgctctcg ggggccctga ccctgaccga | 240 |
| gacctgggcg ggttctcaca ccctccagtg gatgattggc tgcgacctgg ggtccgacgg | 300 |
| acgcctcctc cgcgggtatg aacagtatgc ctacgatggc aaggattacc tcgccctgaa | 360 |
| cgaggacctg cgctcctgga ccgcagcgga cactgcggct cagatctcca agcgcaagtg | 420 |
| tgaggcggcc aatgtggctg aacaaaggag agcctacctg gagggcacgt gcgtggagtg | 480 |
| gctccacaga tacctggaga acgggaagga gatgctgcag cgcgcggagc agtcttccct | 540 |
| gcccaccatc cccatcatgg gtatcgttgc tggcctggtt gtccttgcag ctgtagtcac | 600 |
| tggagctgcg gtcgctgctg tgctgtggag aaagaagagc tcagattgaa aaggagggag | 660 |
| ctactctcag gctgcaatgt gaaacagctg ccctgtgtgg gactgagtgg caagtccctt | 720 |
| tgtgacttca agaaccctga ctcctctttg tgcagagacc agcccacccc tgtgcccacc | 780 |
| atgaccctct tcctcatgct gaactgcatt ccttccccaa tcacctttcc tgttccagaa | 840 |
| aaggggctgg gatgtctccg tctctgtctc aaatttgtgg tccactgagc tataacttac | 900 |
| ttctgtatta aaattagaat ctgagtataa atttactttt tcaaattatt tccaagagag | 960 |

| | |
|---|---|
| attgatgggt taattaaagg agaagattcc tgaaatttga gagacaaaat aaatggaaga | 1020 |
| catgagaact tt | 1032 |

<210> SEQ ID NO 63
<211> LENGTH: 882
<212> TYPE: DNA
<213> ORGANISM: Homo sapiens

<400> SEQUENCE: 63

| | |
|---|---|
| agtgtggtac tttgtcttga ggagatgtcc tggactcaca cggaaactta gggctacgga | 60 |
| atgaagttct cactcccatt aggtgacagg tttttagaga agccaatcag cgtcgccgcg | 120 |
| gtcctggttc taaagtcctc gctcacccac ccggactcat tctccccaga cgccaaggat | 180 |
| ggtggtcatg gcgccccgaa ccctcttcct gctgctctcg ggggccctga ccctgaccga | 240 |
| gacctgggcg ggttctcaca ccctccagtg gatgattggc tgcgacctgg ggtccgacgg | 300 |
| acgcctcctc cgcgggtatg aacagtatgc ctacgatggc aaggattacc tcgccctgaa | 360 |
| cgaggacctg cgctcctgga ccgcagcgga cactgcggct cagatctcca gcgcaagtg | 420 |
| tgaggcggcc aatgtggctg aacaaaggag agcctacctg agggcacgt gcgtggagtg | 480 |
| gctccacaga tacctggaga cgggaagga gatgctgcag cgcgcggtgt gaaacagctg | 540 |
| ccctgtgtgg gactgagtgg caagtccctt tgtgacttca agaaccctga ctcctctttg | 600 |
| tgcagagacc agcccacccc tgtgcccacc atgaccctct cctcatgct gaactgcatt | 660 |
| ccttccccaa tcacctttcc tgttccagaa aaggggctgg gatgtctccg tctctgtctc | 720 |
| aaatttgtgg tccactgagc tataacttac ttctgtatta aaattagaat ctgagtataa | 780 |
| atttactttt tcaaattatt tccaagagag attgatgggt taattaaagg agaagattcc | 840 |
| tgaaatttga gagacaaaat aaatggaaga catgagaact tt | 882 |

<210> SEQ ID NO 64
<211> LENGTH: 1032
<212> TYPE: DNA
<213> ORGANISM: Homo sapiens

<400> SEQUENCE: 64

| | |
|---|---|
| agtgtggtac tttgtcttga ggagatgtcc tggactcaca cggaaactta gggctacgga | 60 |
| atgaagttct cactcccatt aggtgacagg tttttagaga agccaatcag cgtcgccgcg | 120 |
| gtcctggttc taaagtcctc gctcacccac ccggactcat tctccccaga cgccaaggat | 180 |
| ggtggtcatg gcgccccgaa ccctcttcct gctgctctcg ggggccctga ccctgaccga | 240 |
| gacctgggcg gaccccccca agacacacgt gacccaccac cctgtctttg actatgaggc | 300 |
| caccctgagg tgctgggccc tgggcttcta ccctgcggag atcatactga cctggcagcg | 360 |
| ggatggggag gaccagaccc aggacgtgga gctcgtggag accaggcctg caggggatgg | 420 |
| aaccttccag aagtgggcag ctgtggtggt gccttctgga gaggagcaga gatacacgtg | 480 |
| ccatgtgcag catgaggggc tgccggagcc cctcatgctg agatggaagc agtcttccct | 540 |
| gcccaccatc cccatcatgg gtatcgttgc tggcctggtt gtccttgcag ctgtagtcac | 600 |
| tggagctgcg gtcgctgctg tgctgtggag aaagaagagc tcagattgaa aaggaggag | 660 |
| ctactctcag gctgcaatgt gaaacagctg ccctgtgtgg gactgagtgg caagtccctt | 720 |
| tgtgacttca agaaccctga ctcctctttg tgcagagacc agcccacccc tgtgcccacc | 780 |
| atgaccctct cctcatgct gaactgcatt ccttccccaa tcacctttcc tgttccagaa | 840 |

```
aaggggctgg gatgtctccg tctctgtctc aaatttgtgg tccactgagc tataacttac        900
ttctgtatta aaattagaat ctgagtataa atttactttt tcaaattatt tccaagagag        960
attgatgggt taattaaagg agaagattcc tgaaatttga gagacaaaat aaatggaaga       1020
catgagaact tt                                                          1032

<210> SEQ ID NO 65
<211> LENGTH: 882
<212> TYPE: DNA
<213> ORGANISM: Homo sapiens

<400> SEQUENCE: 65
agtgtggtac tttgtcttga ggagatgtcc tggactcaca cggaaactta gggctacgga         60
atgaagttct cactcccatt aggtgacagg ttttagaga agccaatcag cgtcgccgcg        120
gtcctggttc taaagtcctc gctcacccac ccggactcat tctccccaga cgccaaggat        180
ggtggtcatg gcgccccgaa ccctcttcct gctgctctcg ggggccctga ccctgaccga        240
gacctgggcg gacccccca agacacacgt gacccaccac cctgtctttg actatgaggc        300
caccctgagg tgctgggccc tgggcttcta ccctgcggag atcatactga cctggcagcg        360
ggatggggag gaccagaccc aggacgtgga gctcgtggag accaggcctg caggggatgg        420
aaccttccag aagtgggcag ctgtggtggt gccttctgga gaggagcaga gatacacgtg        480
ccatgtgcag catgaggggc tgccggagcc cctcatgctg agatggatgt gaaacagctg        540
ccctgtgtgg gactgagtgg caagtcccc tgtgacttca agaacctga ctcctctttg         600 tgcagagacc agcccacccc tgtgcccacc atgaccctct tcctcatgct gaactgcatt        660
ccttccccaa tcacctttcc tgttccagaa aaggggctgg gatgtctccg tctctgtctc        720
aaatttgtgg tccactgagc tataacttac ttctgtatta aaattagaat ctgagtataa        780
atttactttt tcaaattatt tccaagagag attgatgggt taattaaagg agaagattcc        840
tgaaatttga gagacaaaat aaatggaaga catgagaact tt                         882

<210> SEQ ID NO 66
<211> LENGTH: 1026
<212> TYPE: DNA
<213> ORGANISM: Homo sapiens

<400> SEQUENCE: 66
agtgtggtac tttgtcttga ggagatgtcc tggactcaca cggaaactta gggctacgga         60
atgaagttct cactcccatt aggtgacagg ttttagaga agccaatcag cgtcgccgcg        120
gtcctggttc taaagtcctc gctcacccac ccggactcat tctccccaga cgccaaggat        180
ggtggtcatg gcgccccgaa ccctcttcct gctgctctcg ggggccctga ccctgaccga        240
gacctgggcg ggctcccact ccatgaggta tttcagcgcc gccgtgtccc ggcccggccg        300
cggggagccc cgcttcatcg ccatgggcta cgtggacgac acgcagttcg tgcggttcga        360
cagcgactcg gcgtgtccga ggatggagcc gcgggcgccg tgggtggagc aggaggggcc        420
ggagtattgg gaagaggaga cacggaacac caaggcccac gcacagactg acagaatgaa        480
cctgcagacc ctgcgcggct actacaacca gagcgaggcc aagcagtctt ccctgcccac        540
catccccatc atgggtatcg ttgctggcct ggttgtcctt gcagctgtag tcactggagc        600
tgcggtcgct gctgtgctgt ggagaaagaa gagctcagat tgaaaaggag ggagctactc        660
tcaggctgca atgtgaaaca gctgcccgt gtggactga gtggcaagtc cctttgtgac         720
ttcaagaacc ctgactcctc tttgtgcaga gaccagccca ccctgtgcc caccatgacc        780
```

| | |
|---|---|
| ctcttcctca tgctgaactg cattccttcc ccaatcacct ttcctgttcc agaaaagggg | 840 |
| ctgggatgtc tccgtctctg tctcaaattt gtggtccact gagctataac ttacttctgt | 900 |
| attaaaatta gaatctgagt ataaatttac tttttcaaat tatttccaag agagattgat | 960 |
| gggttaatta aaggagaaga ttcctgaaat ttgagagaca aaataaatgg aagacatgag | 1020 |
| aacttt | 1026 |

<210> SEQ ID NO 67
<211> LENGTH: 876
<212> TYPE: DNA
<213> ORGANISM: Homo sapiens

<400> SEQUENCE: 67

| | |
|---|---|
| agtgtggtac tttgtcttga ggagatgtcc tggactcaca cggaaactta gggctacgga | 60 |
| atgaagttct cactcccatt aggtgacagg ttttagaga agccaatcag cgtcgccgcg | 120 |
| gtcctggttc taaagtcctc gctcacccac ccggactcat tctccccaga cgccaaggat | 180 |
| ggtggtcatg gcgccccgaa ccctcttcct gctgctctcg ggggccctga ccctgaccga | 240 |
| gacctgggcg gctcccact ccatgaggta tttcagcgcc gccgtgtccc ggcccggccg | 300 |
| cggggagccc cgcttcatcg ccatgggcta cgtggacgac acgcagttcg tgcggttcga | 360 |
| cagcgactcg gcgtgtccga ggatggagcc gcgggcgccg tgggtggagc aggaggggcc | 420 |
| ggagtattgg gaagaggaga cacggaacac caaggcccac gcacagactg acagaatgaa | 480 |
| cctgcagacc ctgcgcggct actacaacca gagcgaggcc atgtgaaaca gctgccctgt | 540 |
| gtgggactga gtggcaagtc cctttgtgac ttcaagaacc ctgactcctc tttgtgcaga | 600 |
| gaccagccca cccctgtgcc caccatgacc ctcttcctca tgctgaactg cattccttcc | 660 |
| ccaatcacct ttcctgttcc agaaaagggg ctgggatgtc tccgtctctg tctcaaattt | 720 |
| gtggtccact gagctataac ttacttctgt attaaaatta gaatctgagt ataaatttac | 780 |
| tttttcaaat tatttccaag agagattgat gggttaatta aaggagaaga ttcctgaaat | 840 |
| ttgagagaca aaataaatgg aagacatgag aacttt | 876 |

<210> SEQ ID NO 68
<211> LENGTH: 781
<212> TYPE: DNA
<213> ORGANISM: Homo sapiens

<400> SEQUENCE: 68

| | |
|---|---|
| gttctcacac cctccagtgg atgattggct gcgacctggg gtccgacgga cgcctcctcc | 60 |
| gcgggtatga acagtatgcc tacgatggca aggattacct cgccctgaac gaggacctgc | 120 |
| gctcctggac cgcagcggac actgcggctc agatctccaa gcgcaagtgt gaggcggcca | 180 |
| atgtggctga acaaaggaga gcctacctgg agggcacgtg cgtggagtgg ctccacagat | 240 |
| acctggagaa cgggaaggag atgctgcagc gcgcggagca gtcttccctg cccaccatcc | 300 |
| ccatcatggg tatcgttgct ggcctggttg tccttgcagc tgtagtcact ggagctgcgg | 360 |
| tcgctgctgt gctgtggaga aagaagagct cagattgaaa aggagggagc tactctcagg | 420 |
| ctgcaatgtg aaacagctgc cctgtgtggg actgagtggc aagtcccttt gtgacttcaa | 480 |
| gaaccctgac tcctctttgt gcagagacca gcccacccct gtgccaccat gaccctcttc | 540 |
| cctcatgctg aactgcattc cttccccaat caccttccct gttccagaaa aggggctggg | 600 |
| atgtctccgt ctctgtctca aatttgtggt ccactgagct ataacttact tctgtattaa | 660 |

```
aattagaatc tgagtataaa tttactttt  caaattattt  ccaagagaga  ttgatgggtt         720
aattaaagga gaagattcct gaaatttgag agacaaaata aatggaagac atgagaactt         780
t                                                                        781
```

<210> SEQ ID NO 69
<211> LENGTH: 631
<212> TYPE: DNA
<213> ORGANISM: Homo sapiens

<400> SEQUENCE: 69

```
gttctcacac cctccagtgg atgattggct gcgacctggg gtccgacgga cgcctcctcc          60
gcgggtatga acagtatgcc tacgatggca aggattacct cgccctgaac gaggacctgc         120
gctcctggac cgcagcggac actgcggctc agatctccaa gcgcaagtgt gaggcggcca         180
atgtggctga acaaaggaga gcctacctgg agggcacgtg cgtggagtgg ctccacagat         240
acctggagaa cgggaaggag atgctgcagc gcgcggtgtg aaacagctgc cctgtgtggg         300
actgagtggc aagtcccttt gtgacttcaa gaaccctgac tcctctttgt gcagagacca         360
gcccacccct gtgccacca  tgaccctctt cctcatgctg aactgcattc cttccccaat         420
cacctttcct gttccagaaa aggggctggg atgtctccgt ctctgtctca aatttgtggt         480
ccactgagct ataacttact tctgtattaa aattagaatc tgagtataaa tttactttt          540 caaattattt ccaagagaga ttgatgggtt aattaaagga gaagattcct gaaatttgag         600
agacaaaata aatggaagac atgagaactt t                                        631
```

<210> SEQ ID NO 70
<211> LENGTH: 1057
<212> TYPE: DNA
<213> ORGANISM: Homo sapiens

<400> SEQUENCE: 70

```
gttctcacac cctccagtgg atgattggct gcgacctggg gtccgacgga cgcctcctcc          60
gcgggtatga acagtatgcc tacgatggca aggattacct cgccctgaac gaggacctgc         120
gctcctggac cgcagcggac actgcggctc agatctccaa gcgcaagtgt gaggcggcca         180
atgtggctga acaaaggaga gcctacctgg agggcacgtg cgtggagtgg ctccacagat         240
acctggagaa cgggaaggag atgctgcagc gcgcggaccc ccccaagaca cacgtgaccc         300
accaccctgt ctttgactat gaggccaccc tgaggtgctg ggccctgggc ttctaccctg         360
cggagatcat actgacctgg cagcgggatg gggaggacca gacccaggac gtggagctcg         420
tggagaccag gcctgcaggg gatggaacct tccagaagtg ggcagctgtg gtggtgcctt         480
ctggagagga gcagagatac acgtgccatg tgcagcatga ggggctgccg gagcccctca         540
tgctgagatg gaagcagtct tccctgccca ccatccccat catgggtatc gttgctggcc         600
tggttgtcct tgcagctgta gtcactggag ctgcggtcgc tgctgtgctg tggagaaaga         660
agagctcaga ttgaaaagga gggagctact ctcaggctgc aatgtgaaac agctgccctg         720
tgtgggactg agtggcaagt cccttttgtga cttcaagaac cctgactcct ctttgtgcag         780
agaccagccc acccctgtgc caccatgac  cctcttcctc atgctgaact gcattccttc         840
cccaatcacc tttcctgttc cagaaaaggg gctgggatgt ctccgtctct gtctcaaatt         900
tgtggtccac tgagctataa cttacttctg tattaaaatt agaatctgag tataaattta         960 cttttttcaaa ttatttccaa gagagattga tgggttaatt aaaggagaag attcctgaaa        1020
tttgagagac aaaataaatg aagacatga  gaacttt                                 1057
```

<210> SEQ ID NO 71
<211> LENGTH: 907
<212> TYPE: DNA
<213> ORGANISM: Homo sapiens

<400> SEQUENCE: 71

```
gttctcacac cctccagtgg atgattggct gcgacctggg gtccgacgga cgcctcctcc      60
gcgggtatga acagtatgcc tacgatggca aggattacct cgccctgaac gaggacctgc     120
gctcctggac cgcagcggac actgcggctc agatctccaa gcgcaagtgt gaggcggcca     180
atgtggctga acaaaggaga gcctacctgg agggcacgtg cgtggagtgg ctccacagat     240
acctggagaa cgggaaggag atgctgcagc gcgcggaccc cccaagaca cacgtgaccc      300
accaccctgt ctttgactat gaggccaccc tgaggtgctg ggccctgggc ttctaccctg     360
cggagatcat actgacctgg cagcgggatg gggaggacca gacccaggac gtggagctcg     420
tggagaccag gcctgcaggg gatggaacct tccagaagtg ggcagctgtg gtggtgcctt     480
ctggagagga gcagagatac acgtgccatg tgcagcatga ggggctgccg agcccctca      540
tgctgagatg gatgtgaaac agctgccctg tgtgggactg agtggcaagt cccttttgtga    600
cttcaagaac cctgactcct ctttgtgcag agaccagccc accctgtgc ccaccatgac      660
cctcttcctc atgctgaact gcattccttc cccaatcacc tttcctgttc cagaaaggg     720
gctgggatgt ctccgtctct gtctcaaatt tgtggtccac tgagctataa cttacttctg     780
tattaaaatt agaatctgag tataaattta cttttcaaa ttatttccaa gagagattga     840
tgggttaatt aaaggagaag attcctgaaa tttgagagac aaaataaatg aagacatga     900
gaacttt                                                                907
```

<210> SEQ ID NO 72
<211> LENGTH: 806
<212> TYPE: DNA
<213> ORGANISM: Homo sapiens

<400> SEQUENCE: 72

```
gggaaggaga tgctgcagcg cgcggacccc cccaagacac acgtgaccca ccaccctgtc      60
tttgactatg aggccaccct gaggtgctgg ccctgggct tctaccctgc ggagatcata     120
ctgacctggc agcgggatgg ggaggaccag acccaggacg tggagctcgt ggagaccagg     180
cctgcagggg atggaacctt ccagaagtgg gcagctgtgg tggtgccttc tggagaggag     240
cagagataca cgtgccatgt gcagcatgag gggctgccgg agcccctcat gctgagatgg     300
aagcagtctt ccctgcccac catccccatc atgggtatcg ttgctggcct ggttgtcctt     360
gcagctgtag tcactggagc tgcggtcgct gctgtgctgt ggagaaagaa gagctcagat     420
tgaaaaggag ggagctactc tcaggctgca atgtgaaaca gctgccctgt gtgggactga     480
gtggcaagtc cctttgtgac ttcaagaacc ctgactcctc tttgtgcaga gaccagccca     540
cccctgtgcc caccatgacc ctcttcctca tgctgaactg cattccttcc ccaatcacct     600
ttcctgttcc agaaaagggg ctgggatgtc tccgtctctg tctcaaattt gtggtccact     660
gagctataac ttacttctgt attaaaatta gaatctgagt ataaatttac tttttcaaat     720
tatttccaag agagattgat gggttaatta aaggagaaga ttcctgaaat ttgagagaca     780
aaataaatgg aagacatgag aacttt                                          806
```

<210> SEQ ID NO 73

```
<211> LENGTH: 781
<212> TYPE: DNA
<213> ORGANISM: Homo sapiens

<400> SEQUENCE: 73
acccccccaa gacacacgtg acccaccacc ctgtctttga ctatgaggcc accctgaggt     60
gctgggccct gggcttctac cctgcggaga tcatactgac ctggcagcgg gatggggagg    120
accagaccca ggacgtggag ctcgtggaga ccaggcctgc aggggatgga accttccaga    180
agtgggcagc tgtggtggtg ccttctggag aggagcagag atacacgtgc catgtgcagc    240
atgaggggct gccggagccc ctcatgctga gatggaagca gtcttccctg cccaccatcc    300
ccatcatggg tatcgttgct ggcctggttg tccttgcagc tgtagtcact ggagctgcgg    360
tcgctgctgt gctgtggaga aagaagagct cagattgaaa aggagggagc tactctcagg    420
ctgcaatgtg aaacagctgc cctgtgtggg actgagtggc aagtccccttt gtgacttcaa    480
gaaccctgac tcctctttgt gcagagacca gccaccccct gtgccaccca tgaccctctt    540
cctcatgctg aactgcattc cttccccaat cacctttcct gttccagaaa aggggctggg    600
atgtctccgt ctctgtctca aatttgtggt ccactgagct ataacttact tctgtattaa    660
aattagaatc tgagtataaa tttacttttt caaattattt ccaagagaga ttgatgggtt    720
aattaaagga gaagattcct gaaatttgag agacaaaata aatggaagac atgagaactt    780
t                                                                    781

<210> SEQ ID NO 74
<211> LENGTH: 656
<212> TYPE: DNA
<213> ORGANISM: Homo sapiens

<400> SEQUENCE: 74
gggaaggaga tgctgcagcg cgcggacccc cccaagacac acgtgaccca ccaccctgtc     60
tttgactatg aggccaccct gaggtgctgg gccctgggct tctaccctgc ggagatcata    120
ctgacctggc agcgggatgg ggaggaccag acccaggacg tggagctcgt ggagaccagg    180
cctgcagggg atgaaccttt ccagaagtgg cagctgtgg tggtgccttc tggagaggag    240
cagagataca cgtgccatgt gcagcatgag gggctgccgg agcccctcat gctgagatgg    300
atgtgaaaca gctgccctgt gtgggactga gtggcaagtc cctttgtgac ttcaagaacc    360
ctgactcctc tttgtgcaga gaccagccca ccctgtgcc accatgacc ctcttcctca    420
tgctgaactg cattccttcc ccaatcacct ttcctgttcc agaaaagggg ctgggatgtc    480
tccgtctctg tctcaaattt gtggtccact gagctataac ttacttctgt attaaaatta    540
gaatctgagt ataaatttac tttttcaaat tatttccaag agagattgat gggttaatta    600
aaggagaaga ttcctgaaat ttgagagaca aataaatgg aagacatgag aacttt        656

<210> SEQ ID NO 75
<211> LENGTH: 16
<212> TYPE: DNA
<213> ORGANISM: Artificial
<220> FEATURE:
<223> OTHER INFORMATION: primer

<400> SEQUENCE: 75
ccactgcccc tggtac                                                     16

<210> SEQ ID NO 76
<211> LENGTH: 20
```

```
<212> TYPE: DNA
<213> ORGANISM: Artificial
<220> FEATURE:
<223> OTHER INFORMATION: primer

<400> SEQUENCE: 76
cctggactca cacggaaact                                        20

<210> SEQ ID NO 77
<211> LENGTH: 21
<212> TYPE: DNA
<213> ORGANISM: Artificial
<220> FEATURE:
<223> OTHER INFORMATION: primer

<400> SEQUENCE: 77
gtaacatagt gtggtacttt g                                      21

<210> SEQ ID NO 78
<211> LENGTH: 20
<212> TYPE: DNA
<213> ORGANISM: Artificial
<220> FEATURE:
<223> OTHER INFORMATION: primer

<400> SEQUENCE: 78
cccaaggcgc ctttaccaaa                                        20

<210> SEQ ID NO 79
<211> LENGTH: 17
<212> TYPE: DNA
<213> ORGANISM: Artificial
<220> FEATURE:
<223> OTHER INFORMATION: primer

<400> SEQUENCE: 79
agccctcacc accgacc                                           17

<210> SEQ ID NO 80
<211> LENGTH: 20
<212> TYPE: DNA
<213> ORGANISM: Artificial
<220> FEATURE:
<223> OTHER INFORMATION: primer

<400> SEQUENCE: 80
cctttgttca gccacattgg                                        20

<210> SEQ ID NO 81
<211> LENGTH: 20
<212> TYPE: DNA
<213> ORGANISM: Artificial
<220> FEATURE:
<223> OTHER INFORMATION: primer

<400> SEQUENCE: 81
ggactcattc tccccagacg                                        20

<210> SEQ ID NO 82
<211> LENGTH: 20
<212> TYPE: DNA
<213> ORGANISM: Artificial
<220> FEATURE:
<223> OTHER INFORMATION: primer

<400> SEQUENCE: 82
```

-continued ggaagaggag acacggaaca                                                20

<210> SEQ ID NO 83
<211> LENGTH: 20
<212> TYPE: DNA
<213> ORGANISM: Artificial
<220> FEATURE:
<223> OTHER INFORMATION: primer

<400> SEQUENCE: 83
tgttccgtgt ctcctcttcc                                                20

<210> SEQ ID NO 84
<211> LENGTH: 20
<212> TYPE: DNA
<213> ORGANISM: Artificial
<220> FEATURE:
<223> OTHER INFORMATION: primer

<400> SEQUENCE: 84
ccaatgtggc tgaacaaagg                                                20

<210> SEQ ID NO 85
<211> LENGTH: 20
<212> TYPE: DNA
<213> ORGANISM: Artificial
<220> FEATURE:
<223> OTHER INFORMATION: primer

<400> SEQUENCE: 85
cctttgttca gccacattgg                                                20

<210> SEQ ID NO 86
<211> LENGTH: 20
<212> TYPE: DNA
<213> ORGANISM: Artificial
<220> FEATURE:
<223> OTHER INFORMATION: primer

<400> SEQUENCE: 86
gcagctccag tgactacagc                                                20

<210> SEQ ID NO 87
<211> LENGTH: 21
<212> TYPE: DNA
<213> ORGANISM: Artificial
<220> FEATURE:
<223> OTHER INFORMATION: primer

<400> SEQUENCE: 87
tcctgtggca tccacgaaac t                                              21

<210> SEQ ID NO 88
<211> LENGTH: 21
<212> TYPE: DNA
<213> ORGANISM: Artificial
<220> FEATURE:
<223> OTHER INFORMATION: primer

<400> SEQUENCE: 88
gaagcatttg cggtggacga t                                              21

<210> SEQ ID NO 89
<211> LENGTH: 20
<212> TYPE: DNA
<213> ORGANISM: Artificial

<220> FEATURE:
<223> OTHER INFORMATION: primer

<400> SEQUENCE: 89
ggcctcaagc gtggctctca                                               20

<210> SEQ ID NO 90
<211> LENGTH: 319
<212> TYPE: PRT
<213> ORGANISM: Homo sapiens

<400> SEQUENCE: 90

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Ser Lys Glu Gly Asp Gly
    290                 295                 300

Gly Ile Met Ser Val Arg Glu Ser Arg Ser Leu Ser Glu Asp Leu
305                 310                 315

<210> SEQ ID NO 91
<211> LENGTH: 227
<212> TYPE: PRT

<213> ORGANISM: Homo sapiens

<400> SEQUENCE: 91

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
                100                 105                 110

Glu Ala Asn Pro Pro Lys Thr His Val Thr His Pro Val Phe Asp
            115                 120                 125

Tyr Glu Ala Thr Leu Arg Cys Trp Ala Leu Gly Phe Tyr Pro Ala Glu
        130                 135                 140

Ile Ile Leu Thr Trp Gln Arg Asp Gly Glu Asp Gln Thr Gln Asp Val
145                 150                 155                 160

Glu Leu Val Glu Thr Arg Pro Ala Gly Asp Gly Thr Phe Gln Lys Trp
                165                 170                 175

Ala Ala Val Val Val Pro Ser Gly Glu Glu Gln Arg Tyr Thr Cys His
                180                 185                 190

Val Gln His Glu Gly Leu Pro Glu Pro Leu Met Leu Arg Trp Ser Lys
                195                 200                 205

Glu Gly Asp Gly Gly Ile Met Ser Val Arg Glu Ser Arg Ser Leu Ser
            210                 215                 220

Glu Asp Leu
225

<210> SEQ ID NO 92
<211> LENGTH: 116
<212> TYPE: PRT
<213> ORGANISM: Homo sapiens

<400> SEQUENCE: 92

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
                100                 105                 110

Glu Ala Ser Glu

```
<210> SEQ ID NO 93
<211> LENGTH: 13
<212> TYPE: DNA
<213> ORGANISM: homo sapiens

<400> SEQUENCE: 93
agtgtggtac ttt                                                        13

<210> SEQ ID NO 94
<211> LENGTH: 22
<212> TYPE: DNA
<213> ORGANISM: Homo sapiens

<400> SEQUENCE: 94
tggaagacat gagaactttc ca                                              22

<210> SEQ ID NO 95
<211> LENGTH: 17
<212> TYPE: DNA
<213> ORGANISM: Homo sapiens

<400> SEQUENCE: 95
atatagtaac atagtgt                                                    17
```